(12) United States Patent
White et al.

(10) Patent No.: US 6,890,716 B1
(45) Date of Patent: May 10, 2005

(54) RECOMBINANT CELL LINE AND SCREENING METHOD FOR IDENTIFYING AGENTS WHICH REGULATE APOPTOSIS AND TUMOR SUPPRESSION

(75) Inventors: Eileen White, Princeton, NJ (US); Anju Thomas, Warren, NJ (US); Gary Kasof, Shrewsbury, MA (US); Lakshmi Goyal, Needham, MA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 0 days.

(21) Appl. No.: 09/674,876

(22) PCT Filed: May 6, 1999

(86) PCT No.: PCT/US99/09793

§ 371 (c)(1),
(2), (4) Date: Dec. 12, 2001

(87) PCT Pub. No.: WO99/57535

PCT Pub. Date: Nov. 11, 1999

Related U.S. Application Data

(60) Provisional application No. 60/107,689, filed on Nov. 9, 1998, provisional application No. 60/092,871, filed on Jul. 15, 1998, provisional application No. 60/091,391, filed on Jul. 1, 1998, and provisional application No. 60/084,664, filed on May 7, 1998.

(51) Int. Cl.$^7$ .............................. C12Q 1/68; C12N 5/00
(52) U.S. Cl. ........................... 435/6; 435/325; 435/455; 435/465; 536/24.1
(58) Field of Search .................... 536/24.1; 435/465, 435/4, 6, 7.1, 7.21, 8, 440, 455, 325

(56) References Cited

U.S. PATENT DOCUMENTS 5,607,967 A * 3/1997 Friedman et al. ........... 514/461

OTHER PUBLICATIONS

Lill et al (Jun. 19, 1997, Nature vol. 387, pp. 823–827).*
Gu et al (Jun. 19, 1997, Nature vol. 387, pp. 819–823).*
Gurtu et al (1996, Biochemical and Biophysical Research Communications vol. 229, pp. 295–298).*

* cited by examiner

*Primary Examiner*—Larry R. Helms
*Assistant Examiner*—Misook Yu
(74) *Attorney, Agent, or Firm*—Dann Dorfman Herrell & Skillman, P.C.

(57) ABSTRACT

This invention provides recombinant cell lines and screening methods useful for identifying agents that induce apoptosis in target cells and therefore may be used to advantage in the treatment of neoplastic disorders.

3 Claims, 31 Drawing Sheets

Figure 21

```
MGRANSRSHSSRSKSRSQSSSRSRSRSHSRKKRYRSRSRTYSRSRSRDRM      50
YSRDYRRDYRNNRGMRRPYGYRGRGRGYYQGGGGRYHRGGYRPVWNRRHS     100
RSPRRGRSRSRSPKRRSVSSQRSRSRSRRSYRSSRSPRSSSSRSSSPYSK     150
SPVSKRRGSQEKQTKKAEGEPQEESPLKSKSQEEPKDTFEHDPSESIDEF     200
NKSSATSGDIWPGLSAYDNSPRSPHSPSPIATPPSQSSSCSDAPMLSTVH     250
SAKNTPSQHSHSIQHSPERSGSGSVGNGSSRYSPSQNSPIHHIPSRRSPA     300
KTIAPQNAPRDESRGRSSFYPDGGDQETAKTGKFLKRFTDEESRVFLLDR     350
GNTRDKEASKEKGSEKGRAEGEWEDQEALDYFSDKESGKQKFNDSEGDDT     400
EETEDYRQFRKSVLADQGKSFATASHRNTEEEGLKYKSKVSLKGNRESDG     450
FREEKNYKLKETGYVVERPSTTKDKHKEEDKNSERITVKKETQSPEQVKS     500
EKLKDLFDYSPPLHKNLDAREKSTFREESPLRIKMIASDSHRPEVKLKMA     550
PVPLDDSNRPASLTKDRLLASTLVHSVKKEQEFRSIFDHIKLPQASKSTS     600
ESFIQHIVSLVHHVKEQYFKSAAMTLNERFTSYQKATEEHSTRQKSPEIH     650
RRIDISPSTLRKHTRLAGEERVFKEENQKGDKKLRCDSADLRHDIDRRRK     700
ERSKERGDSKGSRESSGSRKQEKTPKDYKEYKSYKDDSKHKREQDHSRSS     750
SSSASPSSPSSREEKESKKEREEEFKTHHEMKEYSGFAGVSRPRGTFFRI     800
RGRGRARGVFAGTNTGPNNSNTTFQKRPKEEEWDPEYTPKSKKYFLHDDR     850
DDGVDYWAKRGRGRGTFQRGRGRFNFKKSGSSPKWTHDKYQGDGIVEDEE     900
ETMENNEEKKDRRKEEKE                                    918
```

Figure 25
pcDNA3
anti-Myc
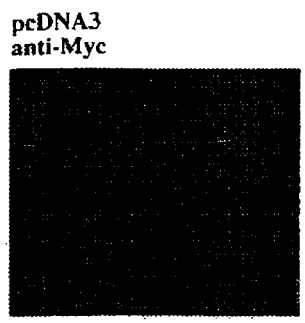
Btf$_S$
anti-Myc
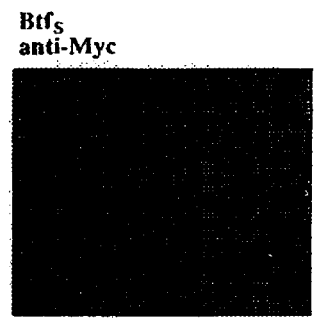
Btf$_S$ + E1B 19K
anti-Myc
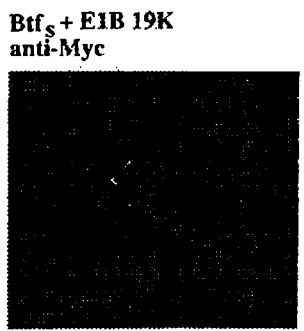
Btf$_S$ + E1B 19K
anti-E1B 19K
Btf$_S$ + Bcl-2
anti-Myc
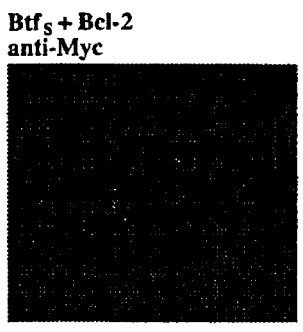
Btf$_S$ + Bcl-2
anti-Bcl-2
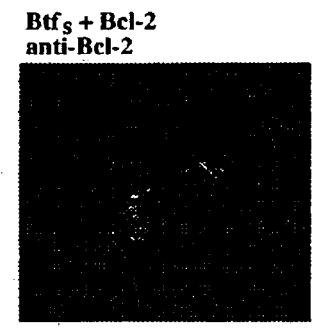

SEQUENCE LISTING

<160> NUMBER OF SEQ ID NOS: 2

<210> SEQ ID NO 1
<211> LENGTH: 2610
<212> TYPE: DNA
<213> ORGANISM: Homo Sapiens

<400> SEQUENCE: 1

```
atgggtcgtg ccaattctag atcacattct tcaaggtcaa agtctagatc acagtctagt      60
tctcgatcaa gatcaagatc tcattctaga aagaagcgat acaggtctcg ttccagaaca     120
tattcaaggt ctcgtagtag agatcgtatg tattctagag attatcgtcg cgattacaga     180
aataatagag gaatgagacg accttatggg tacagaggaa ggggtagagg gtattatcaa     240
```

```
ggaggaggag gtagatatca tcgaggtggt tatagacctg tctggaatag aaggcactct    300
aggagtccta gacgaggtcg ttcacgttcc aggagtccaa aaagaagatc cgtttcttct    360
caaagatcca gaagcagatc tcgccggtca tatagatctt ctaggtctcc aagatcatcc    420
tcttctcgtt cttcatcccc atatagcaaa tctcctgttt ctaaaagacg agggtctcag    480
gaaaaacaaa ccaaaaaagc tgaaggggaa ccccaagaag agagtccgtt gaaaagtaaa    540
tcacaggagg aaccgaaaga tacatttgaa catgacccat ctgagtctat cgatgaattt    600
aataagtcat cagccacatc cggtgatatt tggcctggcc tttcagctta tgataatagt    660
cctagatcac cccatagtcc ttcacctatt gctacaccac ctagtcagag ttcatcttgc    720
tctgatgctc ccatgctcag tacagttcac tctgcaaaaa atactccttc tcagcattca    780
cattccattc agcatagtcc tgaaaggtct gggtctggtt ctgttggaaa tggatctagt    840
cgatacagtc cttctcagaa tagtccaatt catcacatcc cttacgaag aagtcctgca    900 aagacaatcg caccacagaa tgctccaaga gatgagtcta ggggccgttc ctcgttttat    960
cctgatggtg gagatcagga aactgcaaag actgggaagt tcttaaaaag gttcacagat   1020
gaagagtcta gagtattcct gcttgatagg ggtaatacca gggataaaga ggcttcaaaa   1080
gagaaaggat cagagaaagg gagggcagag ggagaatggg aagatcagga agctctagat   1140
tacttcagtg ataaagagtc tggaaaacaa aagtttaatg attcagaagg ggatgacaca   1200
gaggagacag aggattatag acagttcagg aagtcagtcc tcgcagatca gggtaaaagt   1260
tttgctactg catctcaccg gaatactgag gaggaaggac tcaagtacaa gtccaaagtt   1320
tcactgaaag gcaatagaga aagtgatgga tttagagaag aaaaaaatta taaacttaaa   1380
gagactggat atgtagtgga aaggcctagc actacaaaag ataagcacaa agaagaagac   1440
aaaaattctg aaagaataac agtaaagaaa gaaactcagt cacctgagca ggtaaagtct   1500
gaaaagctca agaccctctt tgattacagt cccctctac acaagaatct ggatgcacga   1560
gaaaagtcta ccttcagaga ggaaagccca cttaggatca aaatgatagc gagtgattct   1620
caccgtcctg aagtcaaact caaaatggca cctgttcctc ttgatgattc taacagacct   1680
gcttccttga ctaaagacag gctgcttgct agtacacttg tccattctgt caagaaggag   1740
caagaattcc gatccatctt tgaccacatt aagttgccac aggccagcaa aagcacttca   1800 gagtcatttta ttcaacacat tgtgtccttg gttcatcatg ttaaagagca atacttcaag   1860
tcagctgcaa tgaccctaaa cgagcggttc acttcgtatc agaaagccac tgaagaacat   1920
agtactcggc aaaagagccc tgaaatacac aggagaattg acatctcacc aagtaccctg   1980
aggaagcata cccgtttagc aggggaagag agagttttta agaagaaaaa tcaaaaggga   2040
gataaaaaat taaggtgtga ctctgctgac cttcggcatg acattgatcg ccgtagaaaa   2100
gaaagaagta agaacggggg agattccaag ggctccaggg aatccagtgg atcaagaaag   2160
caggaaaaaa ctccaaaaga ttacaaggaa tacaaatctt acaaagatga cagtaaacat   2220
aaaagagagc aagatcattc tcgatcttca tcctcttcag catcaccttc ttctcccagt   2280
tctcgagaag aaaaggagag taagaaggaa agagaagaag aatttaaaac tcaccatgaa   2340
atgaaagaat actcaggctt tgcaggagtt agccgaccac gaggaaccct tcatgacgac   2400
agagatgatg gtgtggatta ttgggccaaa agaggaagag gtcgtggtac ttttcaacgt   2460
ggcagagggc gctttaactt caaaaaatca ggtagcagtc ctaaatggac tcatgacaaa   2520
taccaagggg atgggattgt tgaagatgaa gaagagacca tggaaaataa tgaagaaaag   2580
```
aaggacagac gcaaggaaga aaaggaataa 2610

<210> SEQ ID NO 2
<211> LENGTH: 917
<212> TYPE: PRT
<213> ORGANISM: Homo sapiens

<400> SEQUENCE: 2

```
Met Gly Arg Ala Asn Ser Arg Ser His Ser Ser Arg Ser Lys Ser Arg
  1               5                  10                  15

Ser Gln Ser Ser Arg Ser Arg Ser Arg Ser His Ser Arg Lys Lys
             20                  25                  30

Arg Tyr Arg Ser Arg Ser Arg Thr Tyr Ser Arg Ser Arg Ser Arg Asp
             35                  40                  45

Arg Met Tyr Ser Arg Asp Tyr Arg Arg Asp Tyr Arg Asn Asn Arg Gly
 50                  55                  60

Met Arg Arg Pro Tyr Gly Tyr Arg Gly Arg Gly Arg Gly Tyr Tyr Gln
 65                  70                  75                  80

Gly Gly Gly Gly Arg Tyr His Arg Gly Gly Tyr Arg Pro Val Trp Asn
                 85                  90                  95

Arg Arg His Ser Arg Ser Pro Arg Arg Gly Arg Ser Arg Ser Arg Ser
                100                 105                 110

Pro Lys Arg Arg Ser Val Ser Ser Arg Ser Arg Ser Ser Arg Ser Arg
            115                 120                 125

Ser Tyr Arg Ser Ser Arg Ser Pro Arg Ser Ser Ser Arg Ser Ser
            130                 135                 140

Ser Pro Tyr Ser Lys Ser Pro Val Ser Lys Arg Arg Gly Ser Gln Glu
145                 150                 155                 160

Lys Gln Thr Lys Lys Ala Glu Gly Glu Pro Gln Glu Glu Ser Pro Leu
                165                 170                 175

Lys Ser Lys Ser Gln Glu Glu Pro Lys Asp Thr Phe Glu His Asp Pro
                180                 185                 190

Ser Glu Ser Ile Asp Glu Phe Asn Lys Ser Ser Ala Thr Ser Gly Asp
            195                 200                 205

Ile Trp Pro Gly Leu Ser Ala Tyr Asp Asn Ser Pro Arg Ser Pro His
210                 215                 220

Ser Pro Ser Pro Ile Ala Thr Pro Pro Ser Gln Ser Ser Ser Cys Ser
225                 230                 235                 240

Asp Ala Pro Met Leu Ser Thr Val His Ser Ala Lys Asn Thr Pro Ser
                245                 250                 255

Gln His Ser His Ser Ile Gln His Ser Pro Glu Arg Ser Gly Ser Gly
            260                 265                 270

Ser Val Gly Asn Gly Ser Ser Arg Tyr Ser Pro Ser Gln Asn Ser Pro
        275                 280                 285

Ile His His Ile Pro Ser Arg Arg Ser Pro Ala Lys Thr Ile Ala Pro
    290                 295                 300

Gln Asn Ala Pro Arg Asp Glu Ser Arg Gly Arg Ser Ser Phe Tyr Pro
305                 310                 315                 320

Asp Gly Gly Asp Gln Glu Thr Ala Lys Thr Gly Lys Phe Leu Lys Arg
                325                 330                 335

Phe Thr Asp Glu Glu Ser Arg Val Phe Leu Leu Asp Arg Gly Asn Thr
                340                 345                 350

Arg Asp Lys Glu Ala Ser Lys Glu Lys Gly Ser Glu Lys Gly Arg Ala
            355                 360                 365
```

-continued

```
Glu Gly Glu Trp Glu Asp Gln Glu Ala Leu Asp Tyr Phe Ser Asp Lys
    370                 375                 380
Glu Ser Gly Lys Gln Lys Phe Asn Asp Ser Glu Gly Asp Asp Thr Glu
385                 390                 395                 400
Glu Thr Glu Asp Tyr Arg Gln Phe Arg Lys Ser Val Leu Ala Asp Gln
                405                 410                 415
Gly Lys Ser Phe Ala Thr Ala Ser His Arg Asn Thr Glu Glu Glu Gly
                420                 425                 430
Leu Lys Tyr Lys Ser Lys Val Ser Leu Lys Gly Asn Arg Glu Ser Asp
            435                 440                 445
Gly Phe Arg Glu Lys Asn Tyr Lys Leu Lys Glu Thr Gly Tyr Val
    450                 455                 460
Val Glu Arg Pro Ser Thr Thr Lys Asp Lys His Lys Glu Glu Asp Lys
465                 470                 475                 480
Asn Ser Glu Arg Ile Thr Val Lys Lys Glu Thr Gln Ser Pro Glu Gln
                485                 490                 495
Val Lys Ser Glu Lys Leu Lys Asp Leu Phe Asp Tyr Ser Pro Pro Leu
                500                 505                 510
His Lys Asn Leu Asp Ala Arg Glu Lys Ser Thr Phe Arg Glu Glu Ser
            515                 520                 525
Pro Leu Arg Ile Lys Met Ile Ala Ser Asp Ser His Arg Pro Glu Val
    530                 535                 540
Lys Leu Lys Met Ala Pro Val Pro Leu Asp Asp Ser Asn Arg Pro Ala
545                 550                 555                 560
Ser Leu Thr Lys Asp Arg Leu Leu Ala Ser Thr Leu Val His Ser Val
                565                 570                 575
Lys Lys Glu Gln Glu Phe Arg Ser Ile Phe Asp His Ile Lys Leu Pro
                580                 585                 590
Gln Ala Ser Lys Ser Thr Ser Glu Ser Phe Ile Gln His Ile Val Ser
            595                 600                 605
Leu Val His His Val Lys Glu Gln Tyr Phe Lys Ser Ala Ala Met Thr
    610                 615                 620
Leu Asn Glu Arg Phe Thr Ser Tyr Gln Lys Ala Thr Glu Glu His Ser
625                 630                 635                 640
Thr Arg Gln Lys Ser Pro Glu Ile His Arg Arg Ile Asp Ile Ser Pro
                645                 650                 655
Ser Thr Leu Arg Lys His Thr Arg Leu Ala Gly Glu Glu Arg Val Phe
                660                 665                 670
Lys Glu Glu Asn Gln Lys Gly Asp Lys Lys Leu Arg Cys Asp Ser Ala
            675                 680                 685
Asp Leu Arg His Asp Ile Asp Arg Arg Lys Glu Arg Ser Lys Glu
    690                 695                 700
Arg Gly Asp Ser Lys Gly Ser Arg Glu Ser Ser Gly Ser Arg Lys Gln
705                 710                 715                 720
Glu Lys Thr Pro Lys Asp Tyr Lys Glu Tyr Lys Ser Tyr Lys Asp Asp
                725                 730                 735
Ser Lys His Lys Arg Glu Gln Asp His Ser Arg Ser Ser Ser Ser Ser
                740                 745                 750
Ala Ser Pro Ser Ser Pro Ser Arg Glu Glu Lys Glu Ser Lys Lys
            755                 760                 765
Glu Arg Glu Glu Glu Phe Lys Thr His His Glu Met Lys Glu Tyr Ser
    770                 775                 780
Gly Phe Ala Gly Val Ser Arg Pro Arg Gly Thr Phe Phe Arg Ile Arg
```

-continued

```
             785                 790                 795                 800
Gly Arg Gly Arg Ala Arg Gly Val Phe Ala Gly Thr Asn Thr Gly Pro
                    805                 810                 815

Asn Asn Ser Asn Thr Thr Phe Gln Lys Arg Pro Lys Glu Glu Glu Trp
                820                 825                 830

Asp Pro Glu Tyr Thr Pro Lys Ser Lys Lys Tyr Phe Leu His Asp Asp
            835                 840                 845

Arg Asp Asp Gly Val Asp Tyr Trp Ala Lys Arg Gly Arg Gly Arg Gly
        850                 855                 860

Thr Phe Gln Arg Gly Arg Gly Arg Phe Asn Phe Lys Lys Ser Gly Ser
865                 870                 875                 880

Ser Pro Lys Trp Thr His Asp Lys Tyr Gln Gly Asp Gly Ile Val Glu
                885                 890                 895

Asp Glu Glu Glu Thr Met Glu Asn Asn Glu Glu Lys Lys Asp Arg Arg
                900                 905                 910

Lys Glu Glu Lys Glu
            915
```

RECOMBINANT CELL LINE AND SCREENING METHOD FOR IDENTIFYING AGENTS WHICH REGULATE APOPTOSIS AND TUMOR SUPPRESSION

CROSS-REFERENCE TO RELATED APPLICATIONS

This application is a 371 of PCT/US99/09793 filed May 6, 1999, claims priority under 35 U.S.C 119(e) from U.S. Provisional Application No. 60/084,664 filed May 7, 1998, 60/091,391, filed Jul. 1, 1998, 60/092,871 filed Jul. 15, 1998 and 60/107,689 filed Nov. 9, 1998, the disclosure of each being incorporated by reference herein.

Pursuant to 35 U.S.C. §202(c) it is acknowledged that the U.S. Government has certain rights in the invention described herein, which was made in part with funds from the National Institutes of Health, Grant Number CA-60088.

FIELD OF THE INVENTION

The present invention relates to the identification of anti-neoplastic agents. Specifically, the invention provides novel cell-based assays and reagents for screening compounds involved in the regulation of apoptosis and tumor suppression.

BACKGROUND OF THE INVENTION

Several publications are referenced in this application by author name and year of publication in parentheses in order to more fully describe the state of the art to which this invention pertains. Full citations for these references are found at the end of the specification. The disclosure of each of these publications is incorporated by reference herein.

Apoptosis is a genetically controlled pathway of programmed cell death. The hallmarks of apoptosis are cytoplasmic boiling, chromatin condensation, and DNA fragmentation. Apoptosis plays a major role in development and disease. Regulation of cell death is essential for normal development and is an important defense against viral infection and the emergence of cancer. Excessive cell death can lead to impaired development and degenerative diseases, whereas too little cell death can lead to cancer and persistent and sustained viral infection.

Tumor suppressor genes are a class of genes involved in different aspects of normal control of cellular growth and division. Inactivation of tumor suppressor genes, usually by genetic means, contributes to tumor development. The first evidence for the existence of such genes came from the observation that fusion of normal cells with tumor cells resulted in hybrids which were nontumorigenic. However, with the loss of chromosomes, which occurs naturally when hybrid cells are grown in culture, the tumorigenic phenotype was sometimes restored. Furthermore, the introduction of normal chromosomes into tumorigenic hybrids can cause reversal to the nontumorigenic phenotype. Thus expression of genes from the normal parent suppresses tumorigenicity.

As the normal functioning of tumor suppressor genes suppresses tumorigenicity, regions of chromosomes which are lost in tumors are likely to carry tumor suppressor genes. Karyotype analysis of a wide variety of tumor types has shown that certain chromosomal deletions occur with a high frequency and in a tumor specific manner, thus implicating the chromosomal region as a likely location of tumor suppressor genes.

Apoptosis is controlled through the expression of an increasing number of genes conserved in nematodes through mammals and viruses. Some gene products are activators of apoptosis, whereas others are inhibitors. Tumor suppressor genes are also widely conserved. The characterization of the function of these gene products will facilitate elucidation of the molecular mechanisms which regulate cell growth at the biochemical level. This knowledge in turn, facilitates the identification and characterization of agents suitable for regulating apoptotic cell death and tumor suppression which may be used to advantage in the treatment of malignancy and other disorders characterized by aberrant cell growth.

SUMMARY OF THE INVENTION

In accordance with the present invention, it has been discovered that inhibition of the transcriptional coactivator p300 induces p53 accumulation resulting apoptotic cell death. p300 is required to transactivate the p53 inhibitor mdm2. Failure of p300 to transactivate mdm2 results in accumulation of p53 to high levels causing apoptosis, a desirable characteristic of anti-cancer therapeutics. The present invention is directed to the identification of p300 transactivating inhibitors which act to induce p53 accumulation through the failure to coactivate mdm2. Such agents should be effective to induce apoptotic cell death for the treatment of proliferative disorders associated aberrant cell growth.

The present invention provides novel cell lines and methods for identifying agents that regulate apoptosis. According to one aspect of the invention a recombinant cell line is provided for identifying and characterizing p300 inhibitors which regulate apoptosis. An exemplary cell line of the invention comprises a) a first plasmid expressing a p300 responsive promoter operably linked to a first reporter gene; b) a second plasmid expressing a non p300 responsive promoter operably linked to a second reporter gene; and c) a third plasmid expressing a selectable marker gene. The cell line may optionally include a plasmid encoding wild-type p300 to augment endogenously expressed p300 protein levels.

In another embodiment of the invention, a screening method is provided using the cell line of the invention to identify therapeutic agents that regulate apoptosis. The screening method entails determining whether a potential therapeutic reagent inhibits p300 activity thereby inducing apoptosis. One such method is performed by contacting the recombinant cells of the invention with the therapeutic agent. The recombinant cells include a first plasmid expressing a p300 responsive promoter operably linked to a first reporter gene, a second plasmid expressing a non p300 responsive promoter operably linked to a second reporter gene; and a third plasmid expressing a selectable marker gene. Following administration of the reagent repression of the p300 responsive reporter and repression of the non-p300 responsive reporter gene by the therapeutic reagent would be assessed via the levels of reporter gene activity. Repression or the p300 responsive reporter gene and not the non-responsive p300 reporter gene indicates that the compound inhibits p300 transactivation and thereby may be efficacious in inducing apoptosis in target cells. In an alternative embodiment, plasmids may be constructed which contain a plurality of the above described gene constructs.

In yet another embodiment of the invention, a Bcl-2 associated transcription factor (referred to herein as BP-1 and btf) having the sequence of SEQ ID NO: 1 has been identified which interacts with E1B: 19K as well as with anti-apoptotic family members, Bcl-2 and Bcl-$_{XL,}$ but not the proapoptotic protein, Bax. Btf protein has a sequence of SEQ ID NO:2, binds DNA in vitro and represses transcription in reporter assays. The Btf gene has been localized to chromosome 6 (6q22–23), a region that is deleted in certain cancers providing support for Btf's role as a tumor suppressor. Btf is also active in a unique pathway by which Bcl-2 regulates apoptosis.

The availability of the DNA sequence encoding btf facilitates the production of large amounts of btf protein in suitable expression systems. The Btf protein so generated may be used to advantage in the production of antibodies or antibody fragments that may be used to detect Btf protein in clinical samples.

Elucidation of the interaction between Bcl-2 and Btf facilitates the identification and characterization of novel therapeutic agents that specifically disrupt the binding the Bcl-2 and Btf, while not affecting Bcl-2 binding to other proteins. Agents that disrupt binding between Bcl-2 and Btf may be assessed in cell lines which co-express the two proteins. Such agents may comprise peptides or other small molecule inhibitors which act competitively to inhibit the binding between Bcl-2 and Btf, there by effectuating cell death in a variety of tumors.

In accordance with the present invention, methods are provided for screening tumor samples for deletion of the Btf gene and/or protein. Such methods may be either immunological and employ Btf specific antibodies to detect the presence or absence of btf protein expression. Alternatively, the methods may be genetically based. Btf specific oligonucleotides may be employed to assess the sample for the presence or absence of btf encoding nucleic acids. In patients having a btf deletion, the Btf gene may be reintroduced via genetic engineering methods.

The cell lines and screening methods of the present invention provide a unique and advantageous testing system for evaluating reagents that regulate apoptosis. Such agents may then be used to advantage to treat pathological conditions related to aberrant cell growth, including cancer.

BRIEF DESCRIPTION OF THE DRAWINGS

FIG. 5A, autoradiograph of blot; FIG. 5A ethidium stained gel showing loading and integrity of RNA.

FIG. 19B shows growth profiles which reveal the minimal regions of E1B 19K required for interaction with BP-1 were mapped using a series of deletion mutants.

FIG. 21 depicts the amino acid sequence of Btf. $Btf_L$, identified in the GenBank database (accession # D79986) is predicted to encode a 918 amino acid protein shown here. $Btf_S$, which was obtained in the λ-screen, contains the complete $Btf_L$ sequence except that it is missing 49 amino acids between residues 797 and 846 (bold) present in $Btf_L$ and BP-1. The underlined regions represent the positions of nuclear localization sequences.

FIG. 25 is a series of micrographs showing that the nuclear subcellular localization of $Btf_S$ is altered by E1B 19K, Bcl-2 and Bcl-$x_L$. HeLa cells were transfected with expression plasmids pcDNA3-Myc-$Btf_S$ alone and with pCMV E1B 19K or pcDNA3-Bcl-2 as indicated. Cells were fixed 24 hours post-transfection and double stained against Myc and E1B 19K or Bcl-2. All cells were photographed with an original magnification of 1000×.

DETAILED DESCRIPTION OF THE INVENTION

Figure 1B:
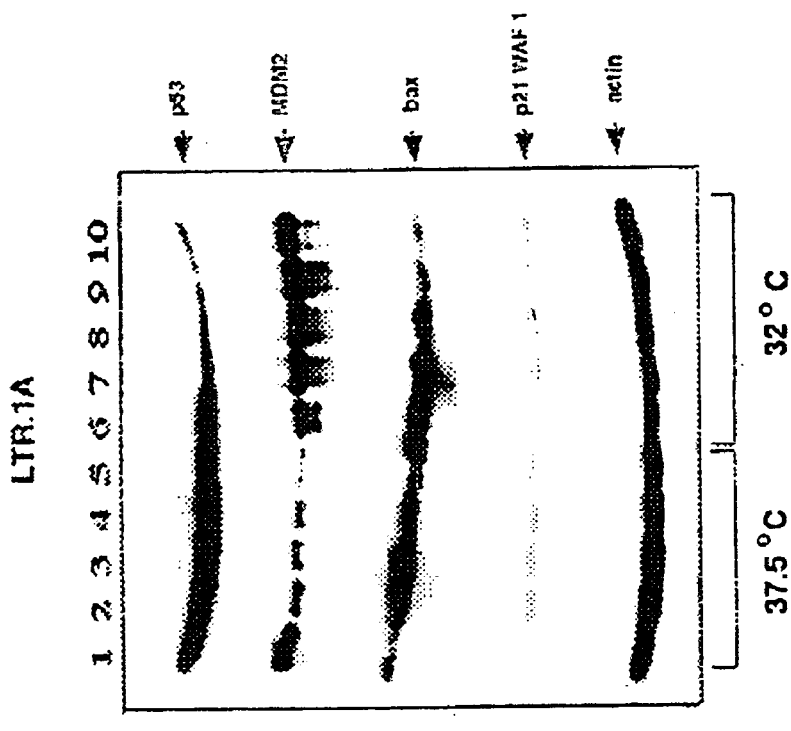
FIGS. 1A and 1B show the results of Western blot analysis of p53, mdm2, Bax, and p21$^{WAF1\ in\ P}$53A and LTR.1A cells after incubation at the nonpermissive (37.5° C.) and permissive (32° C.) temperature at day 0 (lanes 1 and 6), day 1 (lanes 2 and 7), day 2 (lanes 3 and 8), day 3 (lanes 4 and 9) and day 5 (lanes 5 and 10).

The present invention provides cell lines and screening assays and reagents for identifying and characterizing compounds which regulate apoptosis.

The tumor suppressor p53 gene product is a negative regulator of cellular growth and transformation (Ko and Prives 1996; Levine 1997; Vogelstein and Kinzler 1992; White 1996). Many studies have demonstrated that p53 functions as a transcriptional regulator by sequence-specific DNA binding (El-Deiry et al. 1992; Funk et al. 1992; Pietenpol et al. 1994). The p53 gene product regulates transcription by activation or repression (Ko and Prives 1996). DNA damage increases p53 levels which promotes cell cycle arrest allowing DNA repair to occur. Alternatively DNA damage can induce apoptosis presumably when such damage is beyond repair (Ko and Prives 1996; Levine 1997; White 1996). The growth arrest function of p53 is predominantly implemented by transactivation of the cyclin dependent kinase inhibitor p21/WAF1/CIP1 (El-Deiry et al. 1993). p53 can also induce apoptosis by up-regulating the death-promoting bax gene (Miyashita and Reed 1995). Other transcriptional targets for p53 include GADD45 (Kastan et al. 1992), mdm2 (Barak et al. 1993; Wu et al. 1993), cyclin G (Okamoto and Beach 1994), and IGF-BP3 (Buckbinder et al. 1995). The DNA binding ability of p53 plays a major role in regulating cell growth. The most frequently occurring p53 mutations in human tumors are found in this DNA binding domain (Hollstein et al. 1991; Ko and Prives 1996). Accordingly, intact p53 transcriptional functions are important to maintain genomic integrity.

The mdm2 gene was originally cloned because of its amplification in a spontaneously transformed murine BALB/c cell line (Fakharzadeh et al. 1991). The human homologue of mdm2 protein is a negative regulator of p53. Mdm2 protein inhibits p53-mediated functions of $G_1$ arrest and apoptosis (Chen et al. 1996), most likely by binding to the N-terminal transactivation domain of p53 (Momand et al. 1992; Oliner et al. 1993). Furthermore, Mdm2 appears to direct p53 degradation via the ubiquitin pathway (Haupt et al. 1997; Kubbutat et al. 1997). The mdm2 promoter contains p53 binding consensus sequences where p53 binds and positively regulates its expression, creating a negative feedback loop for regulating the activity and levels of p53 (Barak et al. 1993; Haupt et al. 1996; Wu et al. 1993). The functional interdependence of mdm2 and p53 was exemplified in studies with knock-out mice. Loss of mdm2 resulted in early embryonic lethality which was rescued by deletion of p53 (Donehower et al. 1992; Montes de Oca Luna et al. 1995). Thus, mdm2 is required in vivo for down-modulation of p53 function and perturbation of this regulation can be deleterious to embryonic development.

The CBP/p300 family members regulate transcription by functioning as transcriptional coactivators. Although the precise mechanism of how transcriptional adaptors function is not known, CBP/p300 and an interacting protein, P/CAF, have been shown to have histone acetyltransferase activity (Bannister and implicating a role for histone acetylation in transcriptional regulation. These proteins also interact with several transcription factors such as the TAFs (Thut et al. 1995), TBP (Abraham et al. 1993), CREB (Chrivia et al. 1993; Kwok et al. 1994), c-Jun/v-Jun (Bannister and Kouzarides 1995), c-Myb/v-Myb (Dai et al. 1996), c-Fos (Bannister and Kouzarides 1995) and others, which may determine the specificity of the regulation. The p300 family of proteins has been recently shown to bind to p53 and function as coactivators of p53-inducible genes (Avantaggiati et al. 1997; Gu et al. 1997; Lill et al. 1997; Scolnick et al. 1997) The N-terminal activation domain of p53 directly interacts with the carboxy-terminal of p300 (Gu and Roeder 1997). It has also been shown that p300 can acetylate the C-terminal domain of p53 and that this modification increases the sequence-specific DNA binding ability of p53 (Gu and Roeder 1997). Thus, acetylation of specific transcription factors may reflect one level of p300 transcriptional regulation.

The adenoviral early region 1 (E1) genes encode for proteins that aid in cellular transformation by activating proliferation and suppressing apoptosis (White 1993; White and Gooding 1994). Expression of the adenoviral E1A gene stimulates cell cycle progression by interacting with and subverting the function of cellular proteins required for normal cell cycle and transcription regulation. E1A interacts with the retinoblastoma (Rb) gene product as well as it's family members, p107 and p130 (Dyson and Harlow 1992; Moran 1993; Whyte et al. 1988). E1A also binds to and sequesters p300 (Eckner et al. 1994; Moran 1993; Yang et al. 1996). E1A interactions with these cellular proteins are important for transformation as suggested by the observation that E1A mutants that fail to interact with these proteins are incapable of promoting transformation. Expression of E1A alone, however, is insufficient to transform primary baby rat kidney (BRK) cells because cell cycle deregulation by E1A also stimulates p53-dependent apoptosis. Binding of p300 to E1A cosegregates with induction of p53 and stabilization (Chiou and White 1997; Querido et al. 1997; Sanchez-Prieto et al. 1995). Transcriptional activation of p53 target genes, such as bax (Han et al. 1996; Sabbatini et al. 1995), followed by induction of caspase activation implements cell death (Rao and White 1997; Sabbatini et al. 1997). Transcriptional activation of the p53 target gene $p21^{WAF1}$ is also induced, which contributes to implementation of cell cycle arrest by p53, which is not apparent due to cell death (Han et al. 1996; Sabbatini et al. 1995).

E1A-induced cellular transformation is sustained by coexpression of the Bcl-2 adenoviral homologue, E1B 19K or Bcl-2 itself, which inhibit E1A-induced, p53-mediated apoptosis. E1B 19K and Bcl-2 inhibit apoptosis in part by binding to the death promoting Bax protein (Han et al. 1996). Thus E1B 19K or Bcl-2 expression inhibits p53-mediated apoptosis but not growth arrest (Chiou et al. 1994; Debbas and White 1993; Han et al. 1996; Sabbatini et al. 1995). These cooperative functions between early adenoviral genes stimulating cell cycle progression and inhibiting apoptosis ensures efficient transformation.

In accordance with the present invention it has been discovered that p300 is specifically required for transactivation of the mdm2 gene by p53 and also for regulating p53-mediated apoptosis. Cells expressing E1A were unable to up-regulate mdm2, causing p53 to be induced to high levels which resulted in p53-dependent apoptosis. In contrast, BRK cells expressing c-Myc instead of E1A, upregulated mdm2, causing p53 down-regulation and inhibition of p53-dependent apoptosis. Thus, the inability to down-regulate p53 is associated with apoptosis and provides an explanation for the differences between the p53-dependent apoptotic response of E1A versus Myc transformed cells.

The adenovirus E1B 19K protein is a potent inhibitor of apoptosis and cooperates with E1A to transform primary rodent cells. E1B 19K shows sequence and functional homology to the mammalian anti-apoptotic gene product, Bcl-2. Like Bcl-2, the biochemical mechanism of E1B 19K function includes binding to and antagonizing cellular pro-apoptotic proteins, such as Bax, Bak, and Nbk/Bik. In addition, there is evidence that E1B 19K can affect gene expression, but whether this contributes to the anti-apoptotic function of 19K has not been determined. In an effort to further understand the functions of E1B 19K, we screened for 19K-associated proteins using the yeast two-hybrid system. A novel protein Btf (Bcl-2-associated transcription factor) was identified that interacts with E1B 19K, as well as with anti-apoptotic family members, Bcl-2 and Bcl-xL, but not the pro-apoptotic protein Bax. btf is a widely expressed gene that encodes a protein with homology to the basic zipper (bZip)—and Myb-DNA binding domains. Btf binds DNA in vitro and represses transcription in reporter assays. E1B 19K, Bcl-2, and Bcl-xL sequester Btf in the cytoplasm and block its transcriptional repression activity. Expression of Btf also inhibited transformation by E1A with either E1B 19K or mutant p53, suggesting a role in either promoting apoptosis or cell cycle arrest. Indeed, the sustained overexpression of Btf in HeLa cells induced apoptosis which was inhibited by E1B 19K. Furthermore, the chromosomal localization of btf (6q22-23) maps to a region that is deleted in some cancers, consistent with a role for Btf in tumor suppression. Thus, btf may represent a novel tumor suppressor gene, residing in a unique pathway by which the Bcl-2 family can regulate apoptosis.

These observations have facilitated the design of recombinant cell lines that may be used to advantage to screen therapeutic agents that regulate apoptosis.

The nucleic acids of the invention are sometimes referred to herein as "isolated nucleic acids". This term, when applied to DNA, is intended to signify a DNA molecule that is separated from sequences with which it is immediately contiguous (in the 5' to 3' directions) in the naturally occurring genome of the organism from which it was derived. For example, the "isolated nucleic acids" of the invention may comprise a DNA molecule inserted into a vector, such as a plasmid or a virus vector, or integrated into the genomic DNA of a procaryote or eucaryote. With respect to RNA molecules of the invention, the term "isolated nucleic acids" primarily refers to RNA molecules encoded by isolated DNA molecules as defined above, or produced by synthetic methods.

The term "transcription control (or regulatory) element" as used herein, refers to an isolated DNA segment that, under specified conditions, possesses a transcription-regulating activity with respect to the expression of a transcription unit (i.e., a gene, as defined below).

The term "enhancer" is used herein to refer to a type of transcription control element. Enhancers generally activate the expression of a cis-linked gene.

The terms "transcription control element," "transcription regulatory element" and "enhancer" are used interchangeably herein when referring to the isolated nucleic acid molecules of the present invention.

The term "transcription factor" refers to protein factors that interact with DNA to enhance or repress transcription.

The term "repressor" refers to a transcription factor that inhibits gene expression upon interaction with DNA.

The term "transcription unit" refers to a nucleic acid molecule comprising one or more sequences which encode a gene product (usually a protein) and which is operably linked to a promoter or other regulatory sequences (enhancers etc.) necessary for expression of the coding sequence. The term "gene" is often used interchangeably with the term "transcription unit".

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "reporter gene" refers to a gene whose expression may be assayed; such genes include, without limitation, lacZ, amino acid biosynthetic genes, e.g., the yeast LEU2, HIS3, LYS2, or URA3 genes, nucleic acid biosynthetic genes, the mammalian chloramphenicol transacetylase (CAT) gene, the luciferase gene, the green fluorescent protein (GFP) or any surface antigen gene for which specific antibodies are available.

A "promoter" is a DNA sequence located proximal to the start of transcription at the 5' end of an operably linked transcribed sequence. The promoter may contain one or more regulatory elements or modules which interact in modulating transcription of the operably linked gene.

The term "tumor suppressor", as used herein, relates to any protein/polypeptide inhibiting growth of tumor cells in-vitro and/or in-vivo. Growth inhibition involves mechanisms such as control of apoptosis and/or of cell cycle progression as well as mechanisms unidentified so far. "Tumor suppressors" are proteins displaying biological activities identical to or similar to those of p53, Rb (retinoblastoma gene product), WT (Wilms tumor suppressor gene), VHL (von Hippel-Lindau tumor suppressor gene), BRCA1 (breast cancer susceptibility gene) and p16 (cyclin-dependent kinase inhibitor).

I. Methods for Constructing Plasmids and Producing the Cell Lines of the Invention The cell lines of the invention may be prepared according to the general methods set forth below for plasmid construction, transformation of cultured cells, and maintenance of cell lines.

A. Plasmids

The plasmids of the invention may be constructed using conventional cloning methods. A variety of different plasmid vectors are commercially available. Protocols for constructing such plasmids are provided in Current Protocols in Molecular Biology, Ausubel et al. (editors), John Wiley & Sons, Inc. 1987-1997. Detailed protocols for constructing the plasmids of the invention are provided hereinbelow.

B. Cell Lines To achieve stable gene transfer, plasmid DNA must first be introduced into host cells. This may be accomplished according to numerous methods known in the art, including but not limited to 1) calcium phosphate precipitation; 2) electroporation; and 3) liposome-mediated transfection. For general protocols, see, e.g., Chapter 9 in Current Protocols in Molecular Biology, Ausubel et al. (editors), John Wiley & Sons, Inc. 1987-1997.

In accordance with the present invention, cell lines can be generated by co-transfection of a plurality of plasmids. Alternatively, a sequential transfection can be performed, whereby a first cell line is generated that has stably incorporated a plasmid containing a p300 regulated promoter, such as the mdm2 promoter, operably linked to a reporter gene such as CAT. This cell line can then be transfected in turn with a plasmid encoding wild type p300 to augment endogenous p300 levels.

Stable transfectants are selected by the ability of an individual cell colony to grow in the presence of a selected antibiotic, by virtue of a resistance-encoding gene carried on the transfecting plasmid DNA and incorporated into the genome of the cell. In a preferred embodiment of the invention, both of the plasmids used would contain a selectable marker gene for double selection of stable transfectants by antibiotic resistance.

II. Uses of Cell Lines for Screening Agents That Regulate Apoptosis

The recombinant cell lines of the invention may be used to identify and characterize therapeutic compounds that act as p300 inhibitors and thereby induce apoptosis.

For example, cells may be transfected with a plasmid containing a reporter gene operably linked to a promoter which is transactivated by p300. An exemplary promoter is the mdm2 promoter. The cells would also be co-transfected with a control plasmid containing a second reporter gene operably linked to a non-p-300 responsive promoter. The cell line may optionally be stably transfected with a cDNA encoding p300 to augment endogenous p300 levels. Such cell lines may be used in reporter assays for compounds that inhibit p300-dependent transcription. These cells lines can be screened for repression of the mdm-2 linked reporter by compounds that do not alter expression of the non-p300 responsive reporter gene.

Another strategy entails assaying p300 directly For molecules that bind to the E1A binding site on p300. Since binding of E1A to p300 inhibits p300 function, any molecule or compound that mimicked E1A, should be a potential p300 inhibitor. An E1A mutant that fails to bind p300 may be used as a control in such an assay.

Additionally, matched cell lines derived from the LTR 1A (myc+tsp53[val135]) cell line, exemplified herein, can be used in an in vivo cell-based screen for p300 inhibitors which, like E1A, promote p53 stabilization by inhibiting mdm-2 transcription and cause apoptosis. LTR 1A cells have intact p300 function and the ts p53 at the permissive temperature retains the capacity to activate the endogenous mdm-2 gene which is required for cell survival. Potentially therapeutic compounds that inhibit p300 function would cause apoptosis at the permissive temperature. This apoptotic phenotype can be used to advantage to identify agents of interest. LTR 1A cells that ectopically express Mdm-2 from a heterologous promoter would not be susceptible to p300 inhibition and are used as a control for p300 specificity.

The availability of the DNA sequences encoding Btf and Bcl-2 also facilitates the design of additional cell lines and screening methods to identify agents which regulate apoptosis via this pathway. Btf and Bcl-2 may be overexpressed and agents that disrupt Btf/Bcl-2 binding assessed. Disruption of Btf/Bcl-2 binding may be assess using co-immunoprecipitation for example. Agents so identified are expected to induce apoptosis in the targeted cell. Detailed methods for detecting apoptosis in cells are provided hereinbelow.

Antibodies specific for Btf are may be used to assess tumor samples for the presence or absence of Btf protein. Methods for generating antibodies and antibody fragments are well known to those of ordinary skill in the art. Screening methods employing such antibodies include but are not limited to Western blotting, immunofluorescence and affinity chromatography.

Oligonucleotide probes and primers may also be used to assess expression of Btf in tumor samples in the clinical setting. DNA would be isolated from the tumor sample in question and assessed for the presence or absence of btf encoding nucleic acids. In accordance with the present invention, nucleic acids having the appropriate level of sequence homology with Sequence I.D. No. 1 may be identified by using hybridization and washing conditions of appropriate stringency. For example, hybridizations may be performed, according to the method of Sambrook et al., (supra) using a hybridization solution comprising: 5×SSC, 5× Denhardt's reagent, 1.0% SDS, 100 μg/ml denatured, fragmented salmon sperm DNA, 0.05% sodium pyrophosphate and up to 50% formamide. Hybridization is carried out at 37–42 ° C. for at least six hours. Following hybridization, filters are washed as follows: (1) 5 minutes at room temperature in 2× SSC and: 1% SDS; (2) 15 minutes at room temperature in 2×SSC and 0.1% SDS; (3) 30 minutes–1 hour at 37° C. in 1×SSC and 1% SDS; (4) 2 hours at 42–65° in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_s = 81.5°\ \text{C.} + 16.6\ \text{Log}\ [Na+] + 0.41(\%\ G+C) - 0.63\ (\%\ \text{formamide}) - 600/\#bp\ \text{in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

If a tumor cell is found to contain a Btf deletion, the tumor cells may be genetically engineered to express the btf gene. Methods for delivering nucleic acids to target cells include retroviral targeting vectors and adenoviral vectors.

The following materials and methods are provided to facilitate the practice of the present invention.

Cells and Culture Conditions

Primary Fisher BRK cells were prepared from 6 day old baby rats and cultured in Dulbecco's modified eagle medium (DMEM) with 10% fetal bovine serum as described previously (White et al. 1991). Plasmids were transfected by electroporation, and cells were maintained in DMEM with 10% fetal bovine serum. The transformed BRK cell line, p53A, was derived from transfection of pCMVE1A and pLTRcGval135 plasmids (Debbas and White 1993). The 19K1 and 4B cell lines were derived from transfecting pCMV19K and pSVBcl-2, respectively, and a neomycin-resistance plasmid, pSVneo, by electroporation (Debbas and White 1993) (Chiou et al., 1994; Sabbatini et al., 1995). Control cell line, p53An1, was derived from p53A cells containing only the neomycin-resistance plasmid (Debbas and White 1993). The LTR.1A cells were generated by transfecting primary BRK cells with 10 μg of LTR H-myc, which expresses human c-Myc, and pLTRcGval135 as described previously (Sakamuro et al. 1995).

Antibodies

SMP14, a mouse monoclonal anti-Mdm2 antibody (Santa Cruz Biotechnology, Inc, Santa Cruz, Calif.) was used at 1:1000 (Western) or 1:100 (immunofluorescence) to detect Mdm2. Clone 248, a murine-specific anti-p53 mouse monoclonal antibody which was kindly provided by Dr. A. Levine was used at 1:5000 to detect p53. Mouse monoclonal anti-p21$^{WAF1}$ (Ab-4, Calbiochem, San Diego, Calif.) was used at 1:50 dilution to detect p21$^{WAF1}$. A rabbit polyclonal anti-Bax (P-19, Santa Cruz) was used at 1:100 to detect Bax and a mouse monoclonal anti-actin antibody (Amersham) was used at 1:1003 dilution to detect actin. Anti-HA mouse monoclonal antibody (Babco, Richmond, Calif.) at 1:1000 dilution was used to detect ectopically expressed p300. A mouse monoclonal anti-E1A antibody M73 (Calbiochem) was used at 1:1000 dilution to detect E1A. A polyclonal anti-E1B 19K antibody was used at 1:10,000 to detect transiently expressed E1B 19K.

Cell Viability and Morphology

Cell viability was measured by trypan blue staining. Cells were trypsinized, centrifuged, resuspended in PBS, and counted using a hemocytometer after diluting in trypan blue. Apoptotic morphology was assessed by scoring for cells that are positive by fluorescence microscopy and are rounded and non adherent. Cell morphology was also documented by photography at 100× magnification on a Nikon phase-contrast microscope and camera using Kodak film.

Western Blot Analysis

Cells were incubated at 37.5° C. and 32° C. for various time intervals prior to lysing in buffer containing 4% SDS and 5% β-mercaptoethanol. Equal amounts of protein (20–30 μg) were electrophoresed on 7.5–12% SDS-PAGE gels and transferred to PVDF membranes. Membranes were blocked for 15 minutes at room temperature in 5% nonfat Carnation dry milk in PBS containing 0.1% Tween-20 (PBST). Membranes were incubated with primary antibody followed by washes in PBST and then incubated with horseradish peroxidase (HRP)-conjugated sheep anti-mouse IgG or donkey anti-rabbit IgG monoclonal antibody at 1:2000 dilution. After several washes, blots were developed using the ECL chemiluminescence detection kit according to manufacturer's recommendations (Amersham LIFE SCIENCES, Arlington Heights, Ill.).

Indirect Immunofluorescence and Microscopy

Cells were fixed in cold methanol prior to incubation with primary antibodies. Subsequent to several washes in PBS, cells were incubated with rhodamine-conjugated goat anti-mouse antibody or fluorescein-conjugated goat anti-rabbit antibody. Cells were then washed, mounted and analyzed by fluorescence microscopy using a Nikon FXA epifluorescence microscope.

Northern Blot Analysis

Cytoplasmic RNA was extracted from p53A and 19K1 cells using the NP-40 lysis protocol as previously described (Muraoka et al. 1996). Northern blots were performed by loading 30 μg of cytoplasmic RNA on a formaldehyde gel and blotted as previously described (Muraoka et al. 1996) using Hybond-N membranes (Amersham) for transfer. The membrane was hybridized with a random-primed labeled murine mdm2-specific probe in ExpressHyb Hybridization solution (CloneTech, Palo Alto, Calif.) at 65° C. Blots were washed in 0.1×SSC and 0.1% SDS at 50° C. and exposed to film for 2 days.

Transient Transfections

The indicated amount of plasmid DNA was transfected by electroporation. After transfection, cells were incubated at 37.5° C. for 24 hours to recover, and were then shifted to 32° C. for 24 hours before analysis for viability by trypan blue staining and apoptotic morphology. For p300 transfections, p53A cells were electroporated with 12 or 24 μg of pCMVβ alone, pCMVβp300 or pCMVp300Δ30 mutant (deletion in E1A-interacting domain) (Arany et al. 1994). For transient expression of E1A proteins, LTR.1A cells were electroporated with 10 μg of pCMVβ alone, pCMV12SE1A, pCMV12S.RG2, or pCMV12S.YH47.928 (Wang et al. 1992). For mdm2 transient expression, p53A cells were electroporated with 5–10 μg of pCMVβ alone, pCMVβ-$X_2$ (wild-type mdm2), and pCMVβ-ΔXM (mutant mdm2 with deletion of the N-terminal p53-binding domain) (Haupt et al. 1997).

Stable Transfections

Cells were transfected by electroporation using 2 μg of pCMVβ alone or pCMVβ-X2 and 200 ng of pSVneo along with 10 μg of salmon sperm DNA. Cells were selected in complete media containing 0.5 mg/ml G418 (Sigma) for a week and then incubated at the permissive temperature to select for cells stably expressing mdm2. Two independent pools of p53A cells stably expressing wild-type mdm2 were analyzed.

Yeast Two-Hybrid System for Identifying E1B 19K Binding Proteins

Procedures for utilizing the two-hybrid system to identify E1B 19K binding proteins were described previously (Han et al., 1996). A HeLa cDNA library was constructed in the pGAD-GH vector and screened against pGBT9-E1B 19K. Plasmids were transformed into S. cerevisae YGH1 cells and positive clones were selected based on growth in the absence of histidine and production of β-galactosidase. False-positive clones were eliminated by testing for interactions with an irrelevant hydrophobic protein (Apc-2) and the empty pGBT9 vector. Missense and deletion mutants of E1B 19K tested for interaction with BP-1 were described previously (Han et al., 1996, supra). pGBT8-Bcl-2 (20) and pGBT9-Bax (26) were also described previously. pGBT8-Bcl-$x_L$ was kindly provided by Dr. G. Nuñez (Univ. of Michigan, Ann Arbor, Mich.).

The full length transcript, $btf_S$ was identified by screening a λ-cDNA library prepared from HeLa cells (Stratagene, La Jolla, Calif.) using conventional techniques. The cDNA sequence of bp-1 and the subsequent full length btf were analyzed using Sequenase 2.0 (US Biochemical, Cleveland, Ohio) according to the manufacturer's specifications and later confirmed by fluorescent terminator cycle sequencing using an automated 377 DNA sequencer (Perkin-Elmer, Applied Biosystems, Foster City, Calif.).

Plasmid Construction

A PCR product of $btf_S$ from the λ-screen was digested with XmaI and NotI (blunt) and ligated into both pGAD-GH cut with XmaI-XhoI (blunt) and pGBT9 cut with XmaI-SalI (blunt). To prepare pcDNA3-Myc-$Btf_S$ for mammalian expression and in vitro translation, oligonucleotides encoding a Myc epitope with flanking KpnI and XmaI sites were annealed with a PCR cloned fragment of $btf_S$ from bluescript digested with XmaI and NotI, and pcDNA3 (Invitrogen, San Diego, Calif.) digested with KpnI and NotI. The resulting plasmid encodes a Myc epitope at the N-terminal end of $Btf_S$. $Btf_S$ and two deletion mutants were fused in frame with the GAL-4 DNA-binding domain in the pm1 vector for use in transcriptional reporter assays (kindly provided by Dr. C. Abate-Shen, Center for Advanced Biotechnology and Medicine, Piscataway, N.J.) The full-length $btf_S$ construct was prepared by digesting pGBT9-$Btf_S$ with XmaI and PstI and ligating into the same sites in the pm1 vector. The N552 and C210 mutants were generated by digesting pGBT9-Btf $_S$ with EcoRI-PstI and XmaI-BamHI, respectively, and ligating into the same restriction sites within pm1. $btf_S$ was also cloned into pIRES-EGFP (Clontech, San Francisco, Calif.) for cell cycle analysis of Btf $_S$ expressing cells. The construct was prepared by digesting pcDNA3-Myc-Btf $_S$ with SmaI and NotI and ligating to pIRES-EGFP cut with EcoRV and NotI. The pcDNA3-Bcl-2 plasmid was prepared by ligating an EcoRI-XhoI fragment from pSFFV-Bcl-2 (Hockenberry et al., 1990) (provided by Dr. S. Korsmeyer, Washington University School of Medicine, Saint Louis, Mo.) into pcDNA3. The C-terminally V5/His tagged E1B 19K was prepared by TA cloning into pcDNA3.1/V5/His-TOPO (Invitrogen, San Diego, Calif.) according to manufacturer's specifications.

Cell Lines

The HeLa cells were maintained in culture in Dulbecco modified Eagle medium (D-MEM) with 10% fetal bovine serum (FBS) at 37° C./5% $CO_2$. Stable HeLa cell lines containing Bcl-$x_L$ were prepared by electroporating 1 μg of pcDNA3-Flag-Bcl-$x_L$ (Merino et al., 1995), provided by Dr. G. Nuñez (Univ. of Michigan, Ann Arbor, Mich.), into HeLa cells and selecting with 1.2 mg/ml geneticin. Expression of Bcl-$X_L$ was verified by immunofluorescence.

Northern Blot for btf Expression

Northern blot analyses were performed using commercially available blots of multiple tissues or cancer lines (Clontech, San Francisco, Calif.). Each lane contained 2 μg of the indicated poly $A^+$ RNA. The $btf_S$ probe was prepared by random priming using a purified XmaI-XhoI fragment from pGAD-GH-$Btf_S$. Human β-actin cDNA supplied with the blots were used as a control probe to confirm equal mRNA loading. Hybridization was performed using ExpressHyb solution (Clontech, San Fransisco, Calif.) according to manufacturer's specifications. Bands were visualized by autoradiography and using a PhosphorImager (Molecular Dynamics, Sunnyvale, Calif.).

In vitro Binding Assay

Binding reactions were performed by combining $^{35}$[S]-methionine-labeled in vitro translated Myc-Btf $_S$ or Myc- Bax (Han et al., 1996) with V5/His-E1B 19K, Bcl-2, Flag-Bcl-$X_L$, or luciferase (Promega Corp., Madison, Wis.) prepared using the TNT T7 reticolocyte lysate system (Progema Corp., Madison, Wis.) according to manufacturer's specifications. Samples were incubated with anti-Myc monoclonal antibody (Oncogene Research Products, Cambridge, Mass.) in 500 µl of NETN buffer [20 mM Tris (pH 8.0), 100 mM NaCl, 1 mM EDTA, and 0.2% NP-40] for 1.5 hrs at 4° C. followed by protein A-sepharose. All samples were then washed three times in NETN buffer, resuspended in 2×Laemmli buffer, boiled for 5 minutes, and analyzed by SDS-PAGE. Gels were fixed in 50% methanol, 10% acetic acid for 1 hour, dried and then visualized by autoradiography.

DNA Binding Assay $^{35}$[S]-Methionine labeled in vitro translated Myc-$Btf_S$ and E1B 19K were prepared from 1 µg of pcDNA3-Myc-$Btf_S$ and pcDNA3-E1B 19K (Han et al., 1996, supra) using the TNT T7 reticolocyte lysate system. The proteins were incubated with 200 µl of native DNA-cellulose (Pharmacia Biotech, Piscataway, N.J.) in 500 µl of NETN buffer for 2 hrs at 4° C. The relative levels of $Btf_S$ and E1B 19K production were determined by immunoprecipitation with anti-Myc (Oncogene Research Products, Cambridge, Mass.) or anti-E1B 19K (White and Cipriani, 1989) in NETN buffer followed by protein A-sepharose and then washed in NETN. Samples were resolved by SDS-PAGE and examined by autoradiography as described above.

Indirect Immunofluorescence

HeLa cells were electroporated with 15 µg of pcDNA3-Myc-$Btf_S$ along with 15 µg of either pCMV-E1B 19K (White and Cipriani, 1989, supra) or pcDNA3-Bcl-2. Total amount of DNA was kept constant using empty pcDNA3 vector. Cells grown on glass coverslips were stained 24 hours post-transfection as described previously (Perez and White, 1998). Briefly, the cells were fixed with 2% paraformaldehyde in Phosphate Buffered Saline (PBS), and then permeabilized with 0.5% Triton X-100 in PBS. The cells were double labeled with an anti-Myc mouse monoclonal antibody (Oncogene Research Products, Cambridge, Mass.) along with either an anti-E1B 19K rabbit polyclonal (White and Cipriani, 1989, supra) or an anti-Bcl-2 hamster monoclonal antibody (PharMingen, San Diego, Calif.). Antibody complexes were visualized with rhodamine-conjugated goat anti-mouse antibody along with the fluorescein-conjugated antibodies goat anti-rabbit or goat anti-hamster (Jackson ImmunoResearch Laboratories, Inc., West Grove, Pa.). Immunocytochemistry was also performed in HeLa-Bcl-$X_L$ cells electroporated with 15 µg of pcDNA3-Myc-$Btf_S$. These cells were stained for the Myc epitope as described above. Expression of Flag-tagged Bcl-$X_L$ was confirmed by staining separate coverslips with anti-Flag M5 monoclonal antibody (Scientific Imaging Systems, New Haven, Conn.) and rhodamine-conjugated goat anti-mouse. The cells were visualized by epifluorescence with a Nikon FXA microscope (Nikon Inc., Garden City, N.Y.).

Transcription Assays

Transcriptional reporter assays were performed as described previously (Catron, et al., 1995). HeLa cells were plated onto 60 mm tissue culture dishes and grown to 50–75% confluency. The cells were then transfected with 2.5 µg of a GAL-4 luciferase reporter construct (kindly provided by Dr. C. Abate-Shen, Center for Advanced Biotechnology and Medicine, Piscataway, N.J.) along with 2.5 µg of both a pm1 vector ($Btf_S$, $Btf_S$-N552 or $Btf_S$-C210) and a bcl-2 family gene (pCMV-E1B 19K, pcDNA3-Bcl-2, or pcDNA3-Flag-Bcl-$x_L$). DNA concentrations were kept constant using appropriate empty vectors, either pm1 or pcDNA3. The cells were transfected using SuperFect (Qiagen, Valencia, Calif.) according to the manufacturer's specifications and harvested 24 hours post-transfection. Expression of mutant and wild-type $Btf_S$ proteins were verified by immunofluorescence using an antibody against the GAL-4 DNA-binding domain (Clontech, San Fransisco, Calif.). Luciferase activity was determined using the Luciferase Assay System (Promega Corp., Madison, Wis.) measured in a scintillation counter, and then normalized for protein concentrations measured by a Bradford assay. Values were graphed as a percent of the negative control (empty pm1, empty pcDNA3, and GAL-4 luciferase).

Transformation Assay

Transformation assays of baby rat kidney (BRK) cells were performed as described previously (White et al., 1992). Briefly, BRK cells prepared from 6-day-old Fisher rats were electroporated with carrier DNA along with linerized test DNA (15 µg pCMV-E1A (White et al., 1991), 15 µg pCMV-E1B 19K or pCMV-p53DD (Shaulian, et al., 1992), and 45 µg pcDNA3-Myc-$Btf_S$). DNA concentrations were kept constant using appropriate empty vectors. The cells were cultured for 3 to 4 weeks at 38.5° C. in D-MEM supplemented with 5% FBS, and then stained with Giemsa. Foci were counted from four dishes per condition.

Cell Cycle Analysis

HeLa cells were electroporated with 20 µg pIRES-EGFP-$Btf_S$ or empty pIRES-EGFP vector in combinations with 10 µg pCMV-E1B 19K or empty pcDNA3 vector. Cells were harvested 48 and 72 hours post-transfection and fixed in 2% paraformaldehyde in PBS for 30 min at 4° C. The cells were washed and then stained with PBS containing 1 µg/ml propidium iodide, 250 µg/ml RNase A, and 0.1% Tween 20 for at least 30 min at room temperature. The fluorescent intensities for EGFP and propidium iodide were analyzed by FACS (EPICS PROFILE-II; Coulter, Miami, Fla.). In addition, the live transfected cells were stained with Hoechst dye to visualize the DNA and photographed with a Nikon FXA microscope (Nikon Inc., Garden City, N.Y.).

The following examples are provided to illustrate particular embodiments of the invention. They are not intended to limit the invention in any way.

EXAMPLE I mdm2 Expression Regulates p53-Dependent Apoptosis in BRK Cells

BRK cells were transformed by a temperature sensitive p53 (val135) mutant and either adenovirus E1A (p53A) or c-Myc (LTR.1A). As previously reported, both types of cell lines expressed the temperature sensitive p53 (val135) mutant in which p53 is in the wild-type conformation at the permissive temperature of 32° C. and in the mutant conformation at the nonpermissive temperature of 37.5° C. (Debbas and White 1993; Sakamuro et al. 1995). There are two striking differences between E1A+tsp53(val135) transformed (p53A) and myc+tsp53(val135) transformed (LTR.1A) cell lines. First, BRK cells expressing E1A undergo massive apoptosis at the permissive temperature (Chiou et al. 1994; Debbas and White 1993; Sabbatini et al. 1995) whereas the Myc expressing cells undergo a wave of apoptosis within the first 24 hours at the permissive temperature but are predominantly resistant to apoptosis (Sakamuro et al. 1995). Second, E1A expressing cells maintain high levels of p53, whereas the p53 levels are down-regulated at 32° C. in Myc expressing cells (Debbas and White 1993; Sakamuro et al. 1995). Thus, high levels of p53 correlate with augmentation of the apoptotic response in E1A expressing p53A cells. Since E1A stabilizes p53 (Chiou et al. 1994; Lowe and Ruley 1993) and this activity requires that E1A binds to p300 (Chiou and White 1997), this suggests a possible function for sequestration of p300 and induction of p53 levels. Furthermore, recent reports demonstrate the requirement for p300 in p53 transactivation (Gu et al. 1997; Lill et al. 1997; Scolnick et al. 1997), and a role for mdm2 in promoting p53 degradation (Haupt et al. 1997; Kubbutat et al. 1997). The possible role of p300 in the Mdm2-dependent negative-feedback loop and the control of p53-dependent apoptosis was further investigated.

Figure 1A:
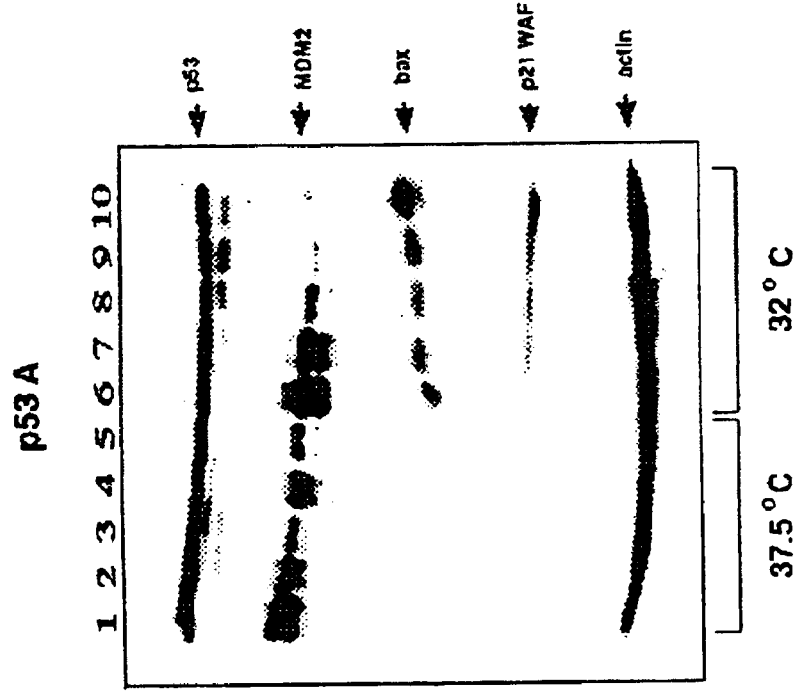
Figure 2:
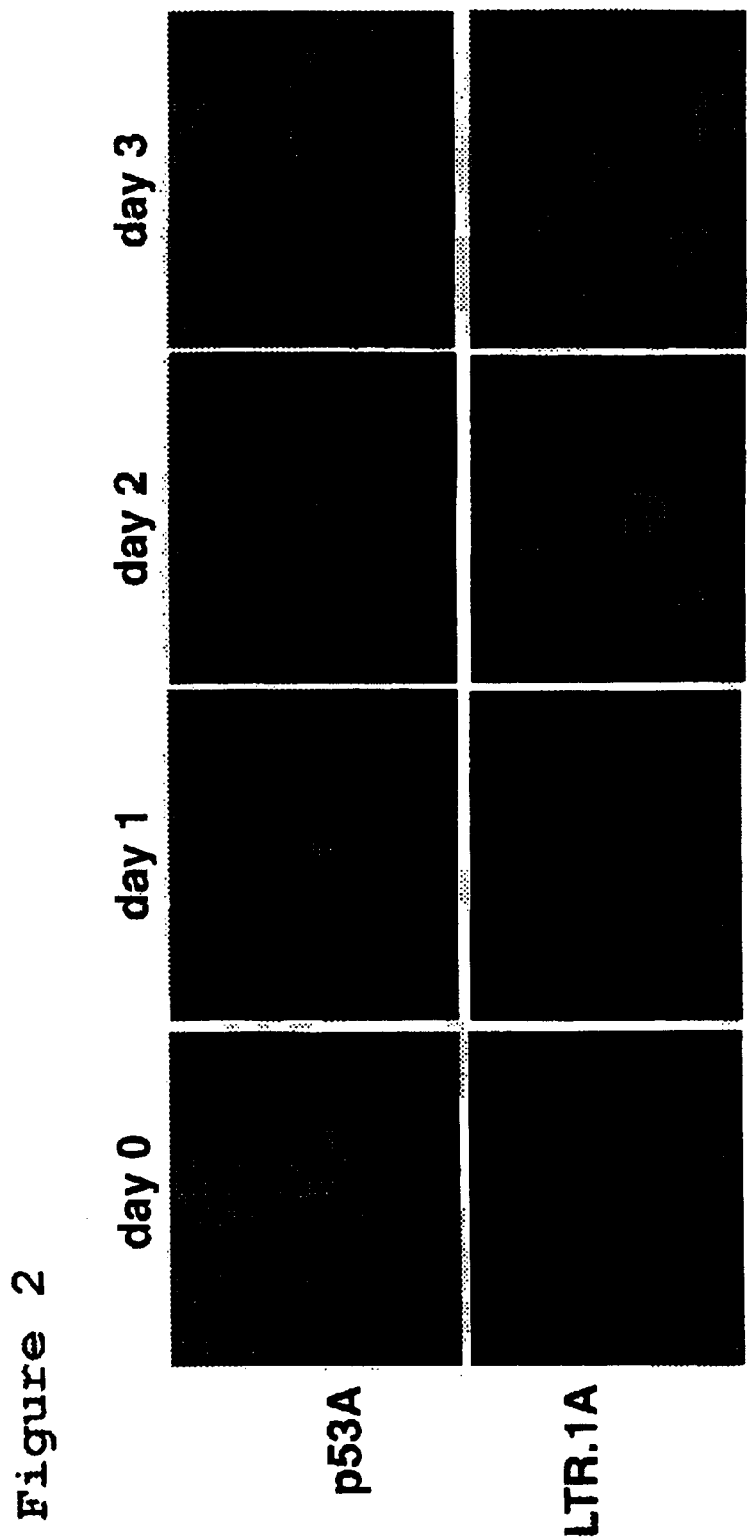
FIG. 2 shows the results obtained from indirect immunofluorescence of mdm2 in p53A (top panel) and LTR.1A (bottom panel) cells after incubation at 32° C. from day 0 to day 3.
Figure 3A:
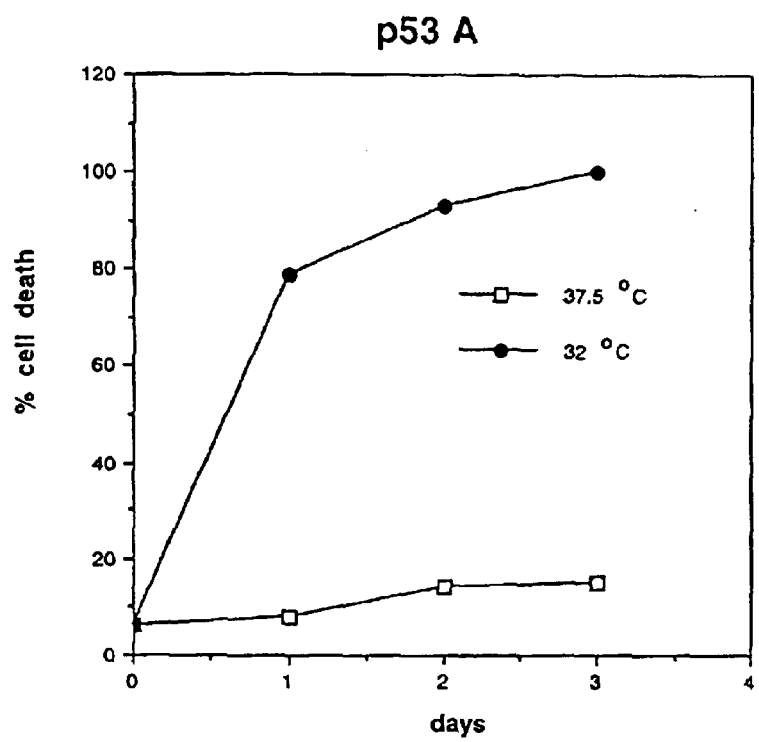
FIGS. 3A and 3B are a pair of graphs showing cell viability as demonstrated by trypan blue staining of p53A and LTR.1A cells at the nonpermissive (37.5° C.) and permissive (32° C.) temperature from day 0 to day 3.
Figure 4:
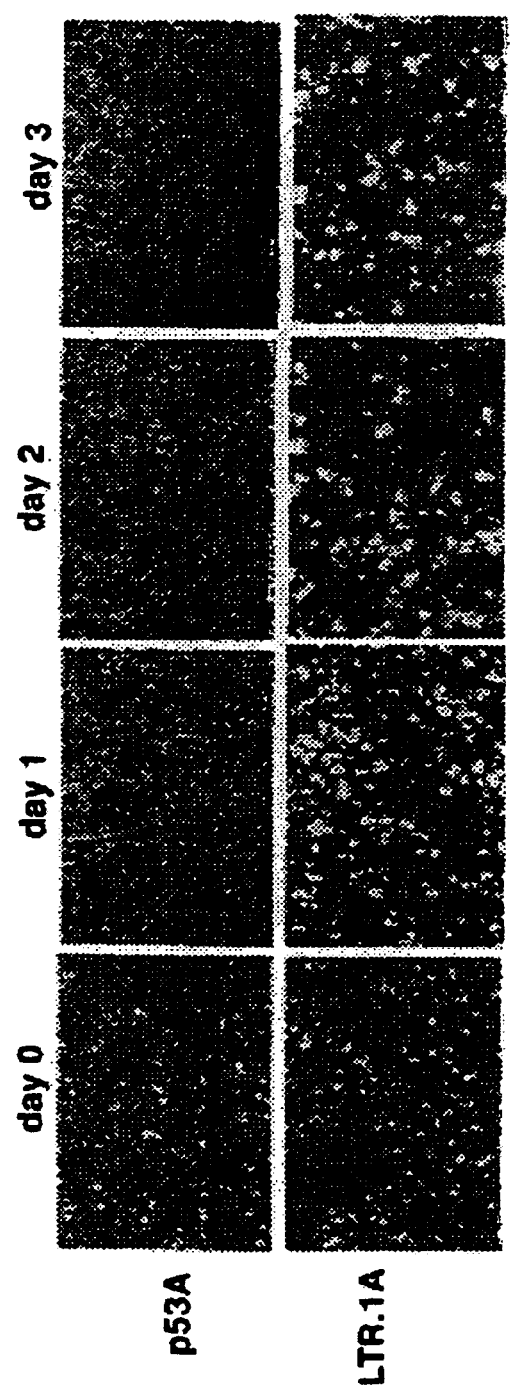
FIG. 4 depicts a series of micrographs showing light microscopy analysis of p53A and LTR.1A cells incubated at 32° C. from day 0 to day 3 to detect apoptotic cells.

In accordance with the present invention it was determined whether the levels of p53-inducible gene products mdm2, $p21^{WAF1}$ and Bax were affected by the p300-binding protein E1A. Western blot analysis shows that p53 levels were up-regulated in E1A transformed cells and down-regulated in Myc transformed cells at 32° C. (FIG. 1A) as previously reported (Debbas and White 1993; Sakamuro et al. 1995). A lower band which may represent a proteolytic cleavage product of p53 was also observed in p53A cells as apoptosis progressed at the permissive temperature. See FIG. 1A. High p53 levels correlated with apoptosis in p53A cells. See FIG. 3A and FIG. 4, top panel. Endogenous mdm2 protein was initially present but was down-regulated at 32° C. in p53A cells as shown by Western blot analysis (FIG. 1) and immunofluorescence (FIG. 2, upper panel). Western blot analysis of mdm2 in p53A cells at the permissive temperature showed a lower band around 50 kDa recognized specifically by the anti-Mdm2 monoclonal antibody (data not shown). This lower band may represent a cleavage product of mdm2. However, this band dissappeared as cells were incubated at the permissive temperature. Mdm2 down-regulation was surprising since mdm2 is a p53-regulated gene and suggested that p300 may be necessary for mdm2 transactivation by p53.

Figure 3B:
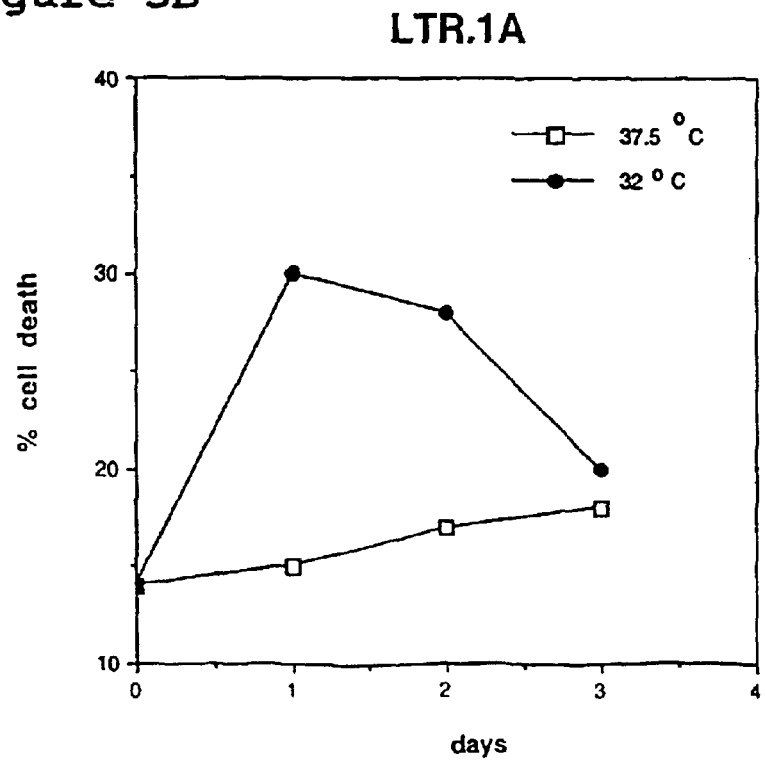

In c-Myc transformed LTR.1A cells, mdm2 was up-regulated and p53 levels were low at 32° C. See FIG. 1B and FIG. 2, lower panel). Therefore Myc, but not E1A expressing BRK cells demonstrate p53-dependent induction of mdm2. Furthermore, high levels of mdm2 in Myc transformed BRK cells may have promoted p53 degradation as shown in FIG. 1A. The LTR.1 A cells initially undergo apoptosis but rapidly become resistant to p53-mediated cell death at 32° C. (FIG. 3, bottom panel and FIG. 4, bottom panel) which correlated with the down-regulation of p53 and up-regulation of mdm2.

mdm2 is only one of many p53-inducible genes that collectively act to modulate the physiological response to p53 induction. Therefore, $p21^{WAF1}$ and Bax levels were also examined for transactivation in p53A and LTR. 1A cells. In p53A cells, Bax and $p21^{WAF1}$ levels were induced at 32° C. even in the presence of E1A and inhibition of p300 as shown in FIG. 1A and FIG. 1B (Han et al. 1996; Sabbatini et al. 1995). LTR.1A cells down-regulated Bax but up-regulated low levels of $p21^{WAF1}$ at 32° C. See FIG. 1. Similar results (data not shown) were obtained with independent E1A+ tsp53(val135) and c-Myc+tsp53(val135) transformed clones (Debbas and White 1993; Sakamuro et al. 1995). These results indicate that E1A and Myc differentially alter p53-dependent gene expression.

Figure 5A:
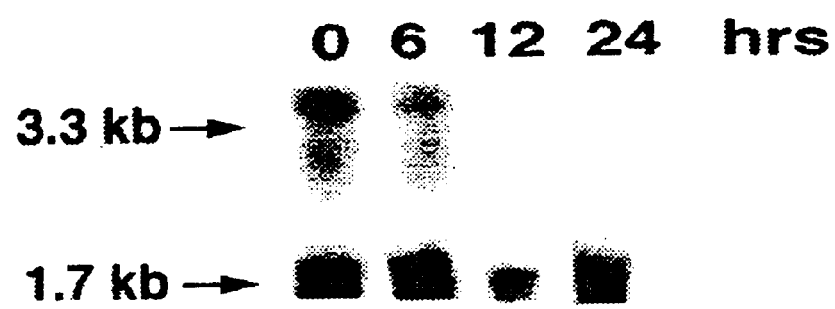
FIGS. 5A and 5B show the results of Northern blot analysis of mdm2 expression of p53A cells incubated at 32° C. for the indicated times.
Figure 5B:
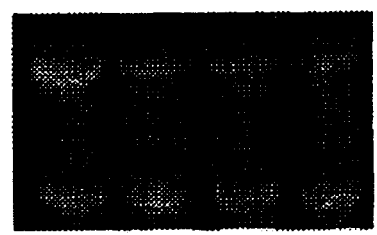
Figure 6:
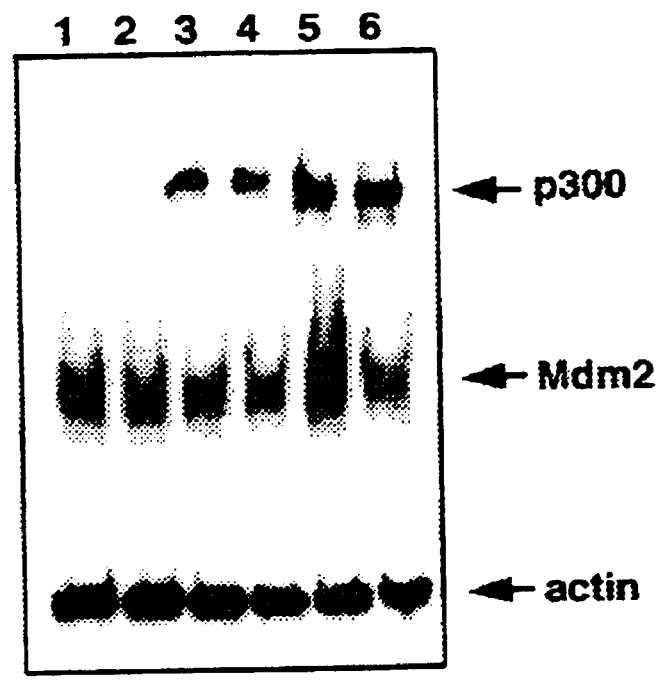
FIG. 6 is an autoradiograph showing the results of Western blot analysis of ectopically expressed HA-tagged p300, endogenous mdm2, and actin in p53A cells transiently transfected by electroporation with pCMVβ alone (lane 1–12 μg and lane 2—24 μg), pCMVβp300 (p300 wild-type) (lane 3—12 μg and lane 4–24 μg) or p300 Δ30 (p300 mutant) (lane 5—12 μg and lane 6—24 μg).
Figure 7:
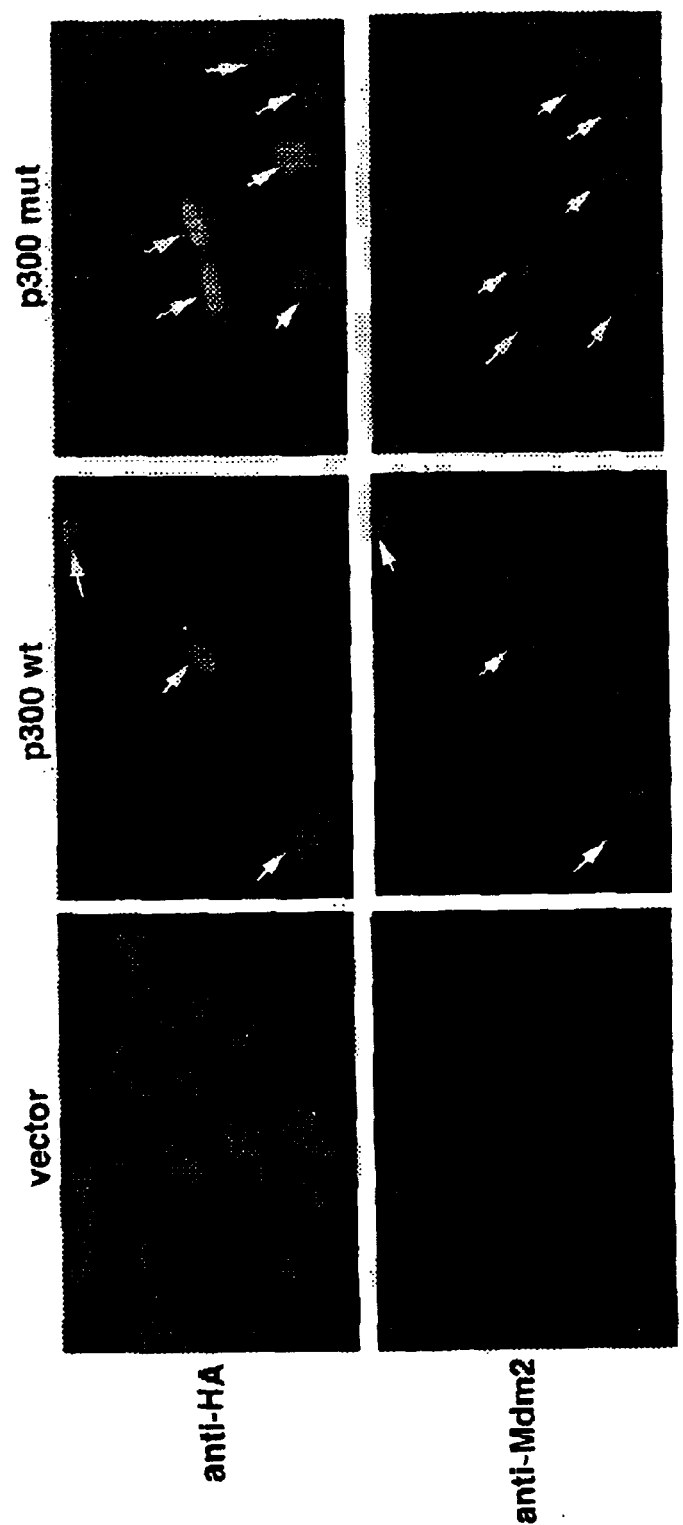
FIG. 7 shows the results of indirect immunofluorescence of HA-tagged p300 and endogenous mdm2 in p53A cells transiently transfected with 24 μg of vector alone, wild-type p300 and mutant p300 (arrows indicate cells with ectopic p300 expression and up-regulation of mdm2).
Figure 8:
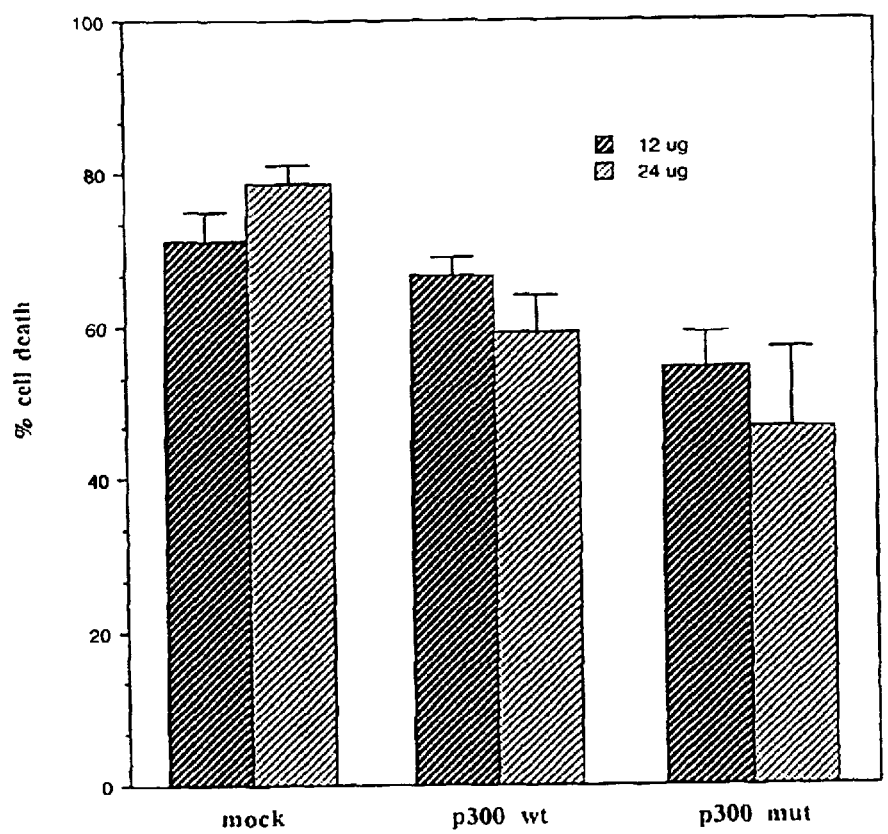
FIG. 8 is a bar graph showing cell viability, as measured by trypan blue staining, of p53A cells transiently transfected with vector alone, wild-type p300 or mutant p300.

In order to determine whether the absence of mdm2 protein in p53A cells reflected a transcriptional event, Northern blot analysis was performed using cytoplasmic RNA extracted from E1A transformed p53A cells incubated at the permissive temperature for the indicated time intervals. See FIG. 5. Two transcripts of 3.3 and 1.7 kb hybridized to a mdm2-specific probe. Both transcripts, particularly the 3.3 kb, were down-regulated to some extent as cells were incubated at 32° C. These results suggest that p300 may be required for mdm2 transactivation, but may be dispensable for Bax and $p21^{WAF1}$ regulation.

p300 is Required for the Up-Regulation of mdm2 by p53 and Inhibition of p53-Mediated Apoptosis We next attempted to rescue p53A cells from apoptosis at the permissive temperature by ectopically expressing p300. Vector alone, wild-type p300 and a functional but truncated form of p300 with a deletion of E1A binding domain (Arany et al. 1994), were transiently transfected in p53A cells. p53-dependent apoptosis was examined at the permissive temperature 48 hours post-transfection. p53A cells transiently expressed the exogenous wild-type p300 and the E1A binding mutant form of p300, neither of which were detected in mock transfected cells. See FIGS. 6 and 7. The up-regulation of mdm2 in p300 transfected cells was not detected by Western blot analysis above endogenous levels (FIG. 6) because the transfection efficiency was low in transient assays. However, the up-regulation of Mdm2 in both wild-type and E1A-binding mutant of p300 was easily observed in 90% of transfected cells by indirect immunofluorescence when individual transfected cells were examined as shown in FIG. 7, lower panel, arrows. Furthermore, ectopic expression of wild-type and mutant p300 rescued cells from apoptosis as cell viability was elevated as much as 20–40% above mock transfected cells. See FIG. 8. The mutant form of p300 which was unable to bind E1A, protected cells better than wild-type p300, presumably because it evades E1A sequestration.

Figure 9:
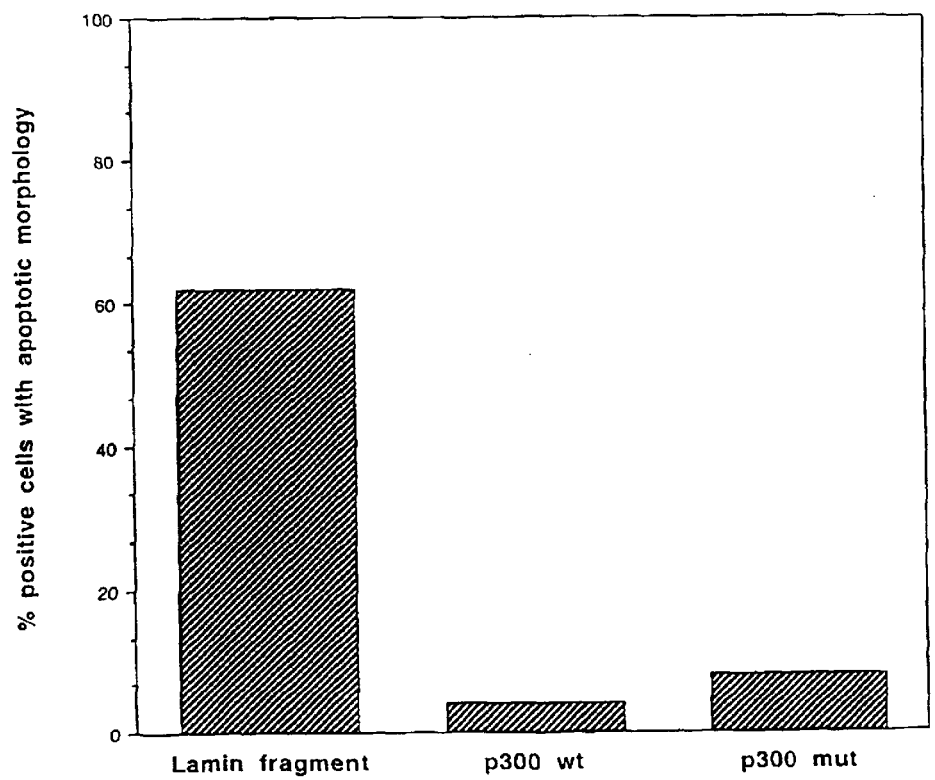
FIG. 9 is a graph showing the percentage of apoptotic cells that are positive for ectopic expression of a control lamin fragment, p300 wild-type and p300 mutant determined by cell morphology using indirect immunofluorescence in p53A cells transiently transfected with 24 μg of pCEP4-LA(1-406). pCMVβp300 or pCMVβp300Δ30 plasmid DNAs.

In addition, we determined the percentage of cells with apoptotic morphology that were ectopically expressing wild-type p300 ectopically or the E1A-binding mutant of p300 following transient transfection with 24 μg of plasmid DNA. Apoptotic morphology was determined by counting cells that were rounded in shape and detaching from the dish. The percentage of cells with apoptotic morphology transiently expressing a control protein, a fragment of the lamin A protein (Rao et al. 1996), compared to p300 and mutant p300 transfected p53A cells at the permissive temperature was determined by indirect immunofluorescence. See FIG. 9. Only 4–8% of the cells expressing wild-type p300 and mutant p300, respectively, have apoptotic morphology compared to 62% cells expressing the lamin fragment (FIG. 9). These results reaffirm that expression of wild-type p300 or the E1A-binding p300 mutant is sufficient to rescue cells from p53-mediated apoptosis.

Figure 10:
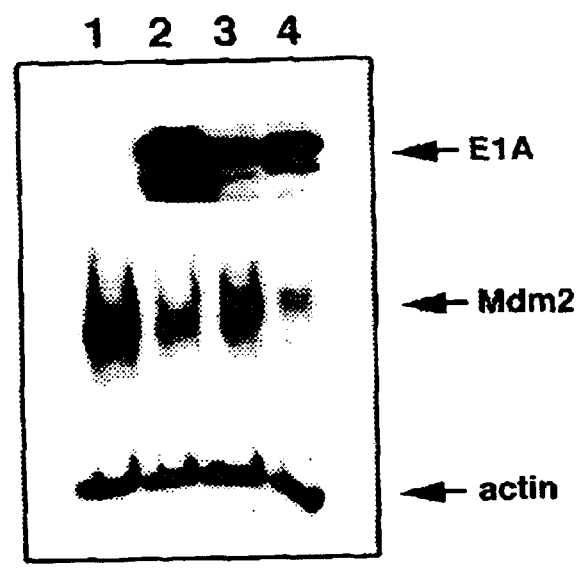
FIG. 10 shows the results of Western Blot analysis of EIA, mdm2 and actin in LTR.1A cells transiently transfected with 10 μg of vector alone (lane 1), 12S E1A (lane 2), 12SRG2 (lane 3), or 12S.YH47.928 (lane 4).
Figure 11:
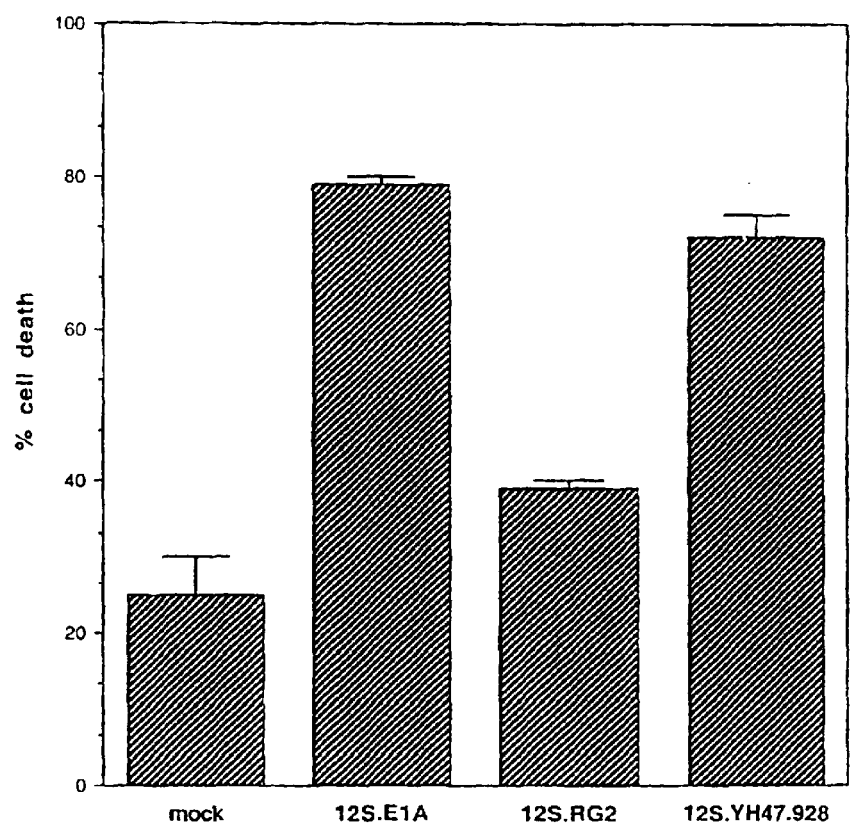
FIG. 11 shows cell viability, as measured by trypan blue exclusion, of LTR.1A cells transiently transfected with vector alone, 12S E1A, 12S.RG2 or 12S.YH47.928.
Figure 12:
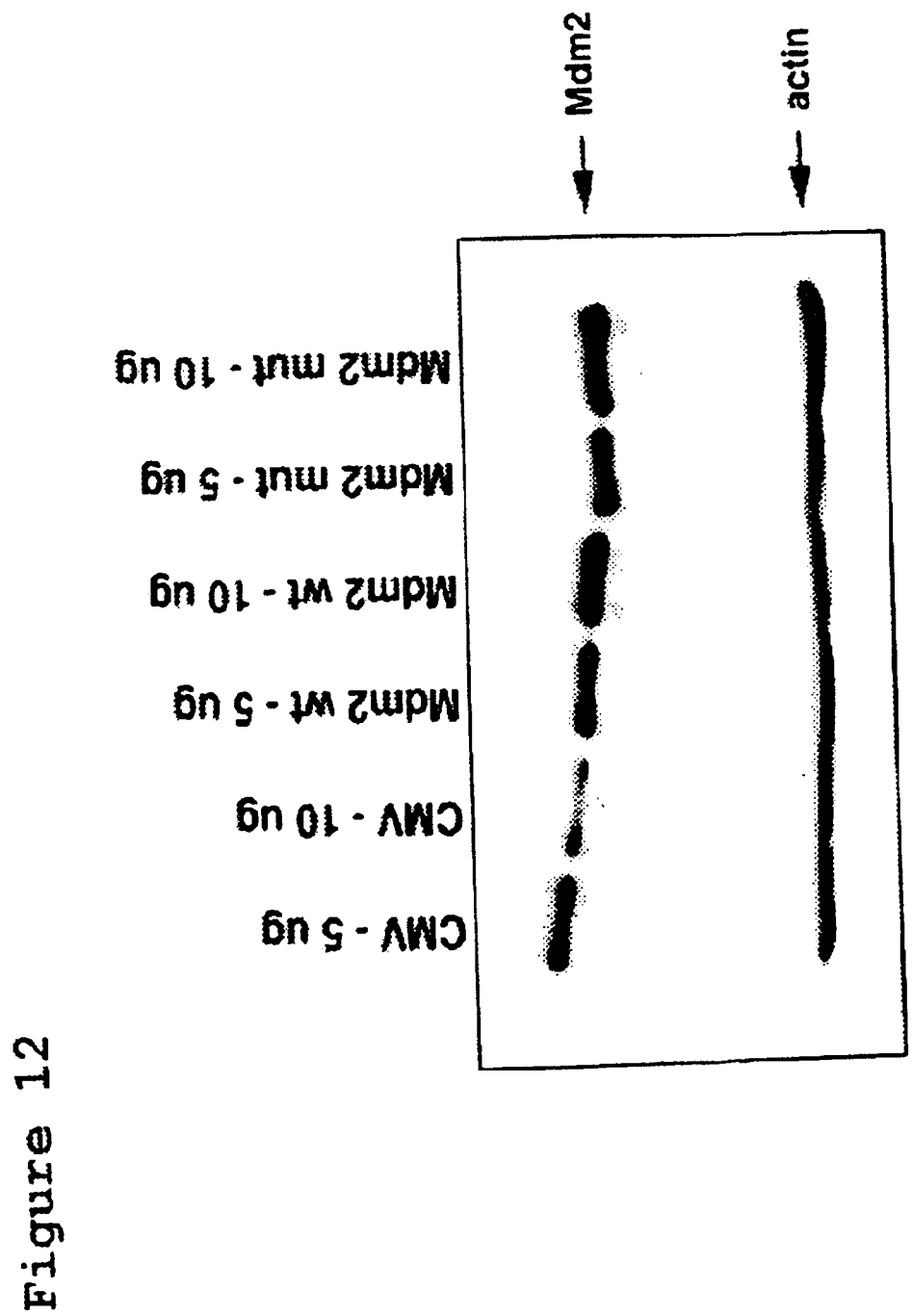
FIG. 12 shows Western blot analysis of p53A cells transiently transfected with 5 and 10 μg of pCMV vector alone, mdm2 wild-type (pCOC-X$_2$) or mdm2 mutant (pCOC-ΔXM) plasmid DNAs.
Figure 13:
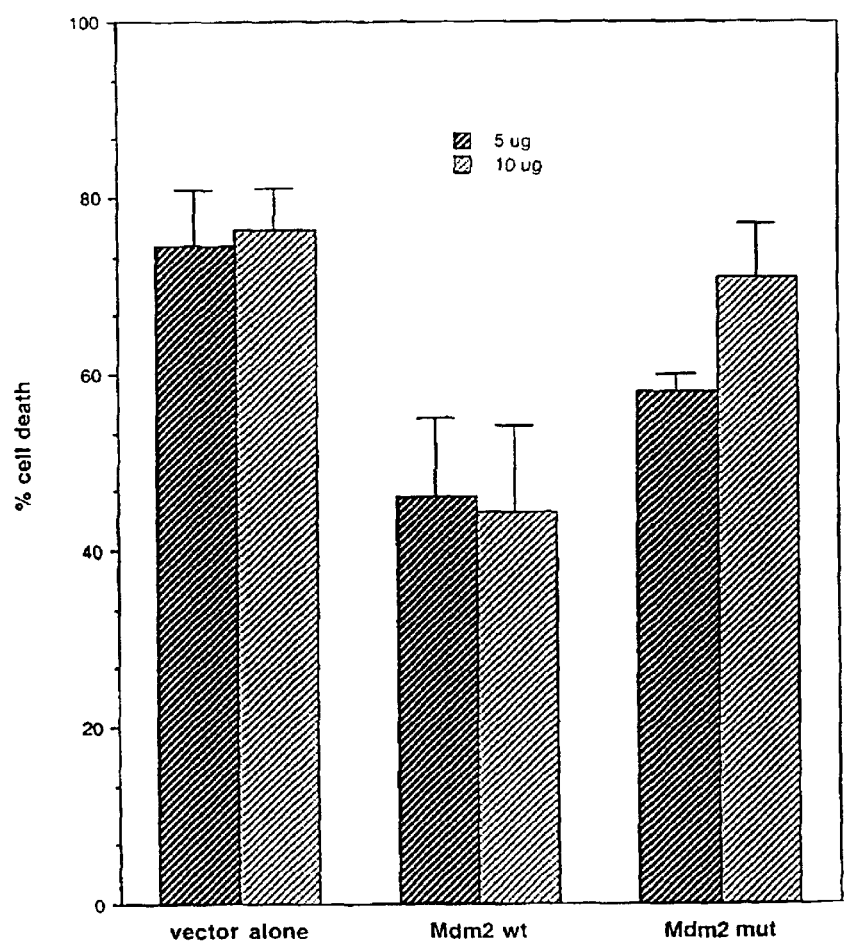
FIG. 13 is a graph showing cell viability as assessed by trypan blue staining of p53A cells transiently transfected with mdm2 expression plasmids incubated at 32°.
Figure 14:
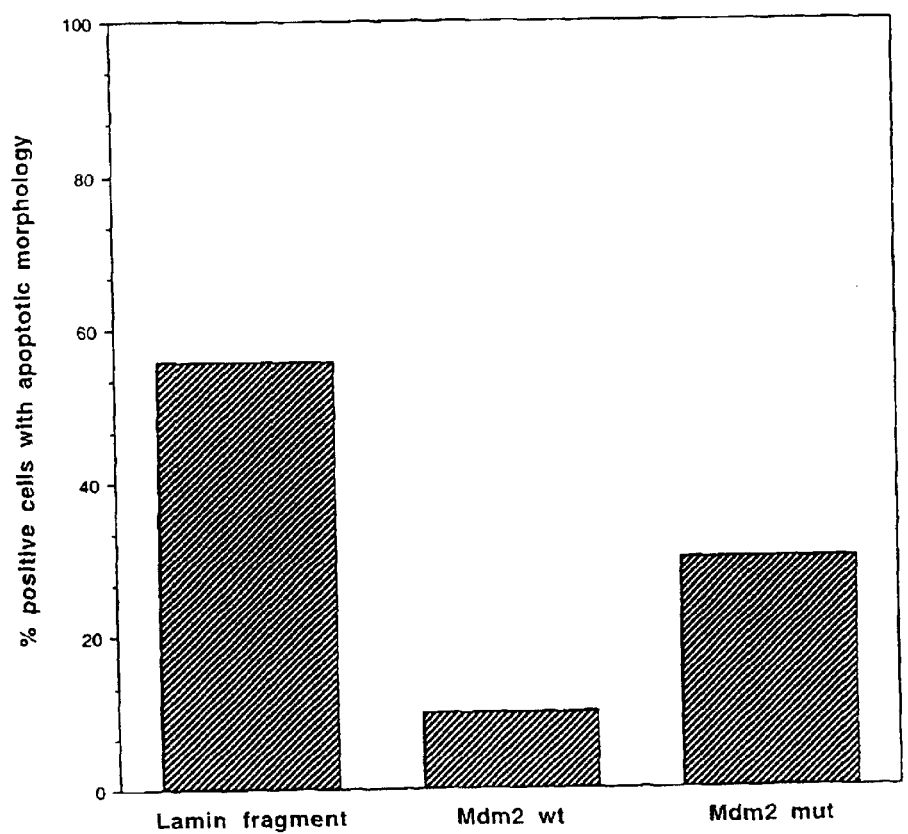
FIG. 14 is a graph showing the percentage of apoptotic cells that were positive for ectopic expression of a control lamin fragment, mdm2 wild-type, and mdm2 mutant determined by cell morphology using indirect immunofluorescence in p53A cells transiently transfected with 10 μg of pCEP4-LA(1-406), pCOC-X$_2$ (wild-type Mdm2) or pCOC-ΔXM (truncated mdm2) plasmid DNAs.

In order to determine whether LTR.1A cells can be made susceptible to p53-mediated death, wild-type E1A (12S E1A) was tranfected into these cells. Transient expression of 12S E1A in LTR.1A cells, see FIG. 10, promoted apoptosis at the permissive temperature as shown in FIG. 11. In addition, mdm2 levels were down-regulated in cells transfected with 12S E1A as detected by Western blot analysis (FIG. 10). Since E1A can also bind to Rb, we transiently transfected LTR.1A cells with 12S E1A mutant (12S.RG2') that is unable to bind to p300 but retains it ability to bind to Rb, and a 12S E1A mutant (12S.YH47.928) that binds to p300 but not to Rb (Wang et al. 1992), and examined p53-dependent apoptosis at the permissive temperature. Cells transfected with 12S.RG2 did not down-regulate mdm2 (FIG. 10) and were resistant to p53-dependent apoptosis (FIG. 11). In contrast, cells transfected with 12S.YH47.928 down-regulated Mdm2 (FIG. 10) and were susceptible to p53-dependent apoptosis at the permissive temperature (FIG. 11). These results suggest that the ability of E1A to bind to p300 and inhibit mdm2 induction correlates with E1A-mediated, p53-dependent apoptosis. Overexpression of mdm2 inhibits p53-mediated apoptosis To determine whether mdm2 expression can bypass the requirement for p300 cotransactivation and rescue p53A cells from p53-mediated death, p53A cells were transiently transfected with expression plasmids encoding wild-type mdm2 and a truncated form of mdm2 lacking the N-terminal p53-binding domain (Haupt et al. 1997). Transient overexpression of wild-type and mutant Mdm2 were detected by Western blot analysis in p53A cells (FIG. 12). Transient transfection of cells with 5 or 10 µg wild-type mdm2 rescued cells from p53-dependent apoptosis at the permissive temperature (FIG. 13). The truncated form of mdm2 rescued cells from apoptosis less efficiently than the wild-type protein (FIG. 13), presumably because it was not able to bind to p53 and promote its degradation. Furthermore, we examined the cell morphology of p53A cells expressing a wild-type and mutant mdm2 plasmid DNA as compared to the morphology of cells expressing a control lamin fragment incubated at the permissive temperature using indirect immunofluorescence (FIG. 14). The percentage of apoptotic cells expressing wild-type and mutant mdm2 was only 10% and 30%, respectively, as compared to 56% apoptosis in cells expressing the control lamin fragment (FIG. 14). The mdm2 mutant, however, possessed greater apoptotic suppressing activity than the control lamin fragment which may indicate that mdm2 can suppress apoptosis by a mechanism independent of p53 binding. These results demonstrate that overexpression of mdm2 can rescue E1A-expressing cells from p53-mediated apoptosis by either promoting p53 degradation or by inhibiting its activity by direct interaction.

E1B 19K or Bcl-2 Can Bypass E1A Inhibition of p300 and Restore mdm2 Transactivation.

Another mechanism for suppressing p53-dependent apoptosis is through expression of Bcl-2 or E1B 19K, which function in part by binding to Bax and inactivating its pro-apoptotic function. To test if Bcl-2 or E1B 19K could also function to suppress apoptosis by influencing p53 target gene expression, we examined p53-inducible gene products, mdm2, p21$^{MAP1}$ and Bax, in p53A cells stably expressing adenovirus E1B 19K (19K1) or its human homolog Bcl-2 (4B).

Figure 15:
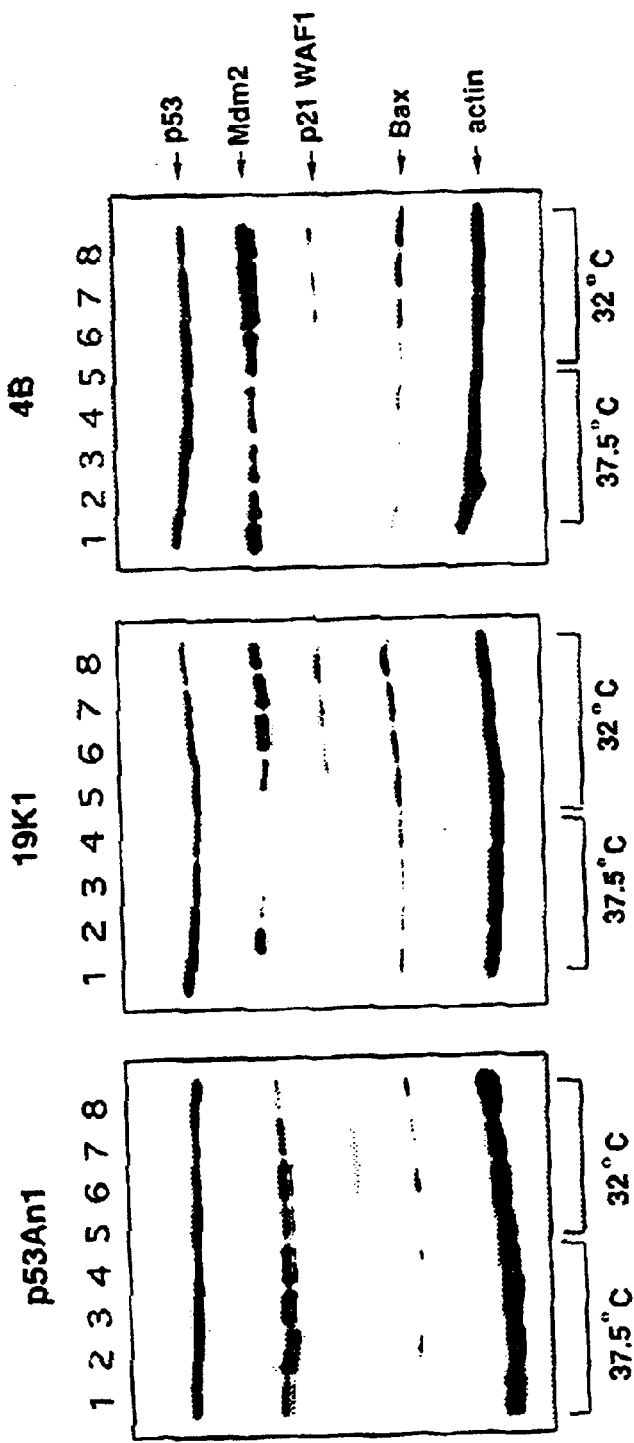
FIGS. 15A, 15B and 15C show the results of Western blot analysis of p53, mdm2, bax, and p21Waf1 in p53A cells stably expressing PSVneo (p53An1) E1B19K (19K1) or Bcl-2 (4B).

As reported previously, the expression of 19K or Bcl-2 abrogates p53 dependent apoptosis at 32° C. (Chiou et al., 1994a; Sabbatini et al., 1995a; Han et al., 1996). Western blot analysis indicated that p21$^{WAF1}$ and Bax levels increased at 32° C. regardless of whether or not 19K or Bcl-2 were expressed and the levels of p53 remained high. See FIGS. 15A, 15B and 15C. However, the presence of 19K or Bcl-2 dramatically up-regulated Mdm2 levels, whereas the control E1A+tsp53 (val135-transformed pS3A cells transfected with vector alone, (p53An1) down regulated mdm2 as expected (FIG. 15). This suggested that E1B 19K or Bcl-2 could restore p53 dependent mdm2 expression in p53A cells.

Figure 16:
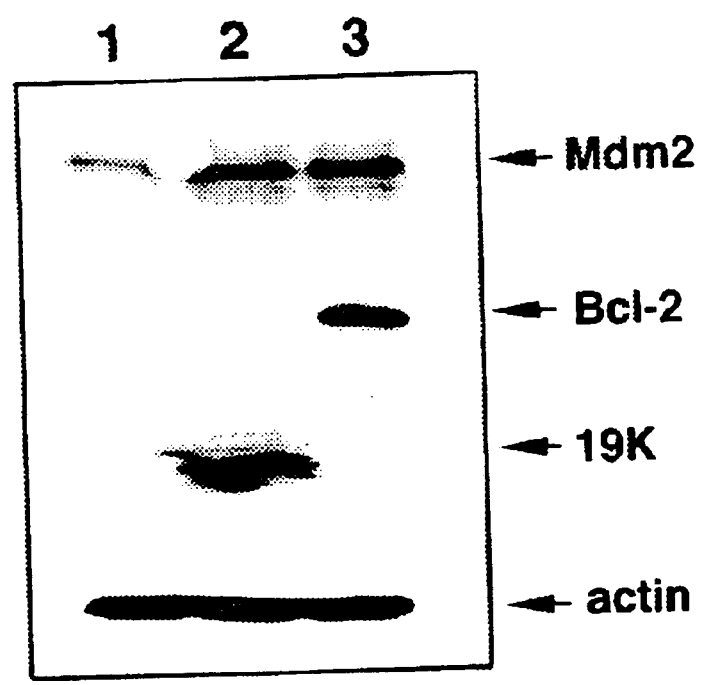
FIG. 16 shows Western blot analysis of mdm2, Bcl-2 E1B 19K and actin in p53An1 cells transfected transiently in pCNDA3 alone, (lane 1); pCMV19K (lane 2) and pCNA3myc-tagged bcl-2, (lane 3).

To determine whether the expression of E1B 19K or Bcl-2 was sufficient for up-regulation of mdm2 levels, we transiently transfected 19K or Bcl-2 in p53An1 cells and examined mdm2 levels at 32° C. Western blot analysis (FIG. 16), and indirect immunofluorescence indicated that mdm2 levels were up-regulated when either 19K or Bcl-2 was expressed transiently.

Figure 17A:
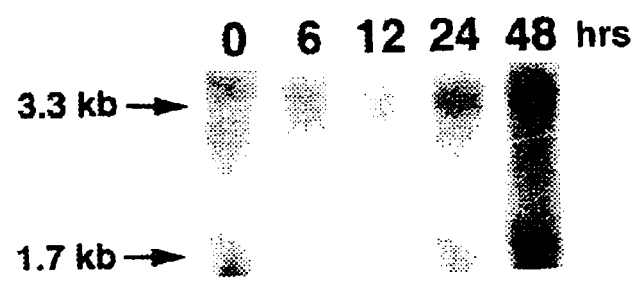
FIG. 17 shows the results of Northern blot analysis of mdm2 expression using 30 μg of cytoplasmic RNA of 19 K1 cells incubated at 32° C. for the indicated time intervals.
Figure 17B:
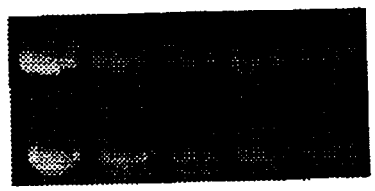

To determine whether expression of E1B 19K upregulates mdm2 at the transcriptional level, we performed Northern blot analysis using cytoplasmic RNA from cells expressing E1B 19K (19K1) incubated at 32° C. for the indicated time intervals (FIG. 17) As shown in FIG. 17, mdm2 mRNA expression was up-regulated after 48 hour incubation at the permissive temperature. This suggested that E1B 19K and Bcl-2 may restore mdm2 transactivation by p53, which would otherwise be inhibited by E1A binding to p300. In addition, previous studies have shown that Bax, and p21$^{MAP1}$ mRNA and protein were also up-regulated in 19K1 cells incubated at the permissive temperature. Therefore, the presence of 19K did not affect the expression of Bax or p21$^{WAF1}$, however, E1B 19K can directly bind to Bax and inhibit its function. E1B 19K and Bcl-2 have been shown to relieve transcriptional repression by E1A and p53, which may be responsible for inhibition of apoptosis and mdm2 may be a physiological target of this activity.

DISCUSSION

Figure 18:
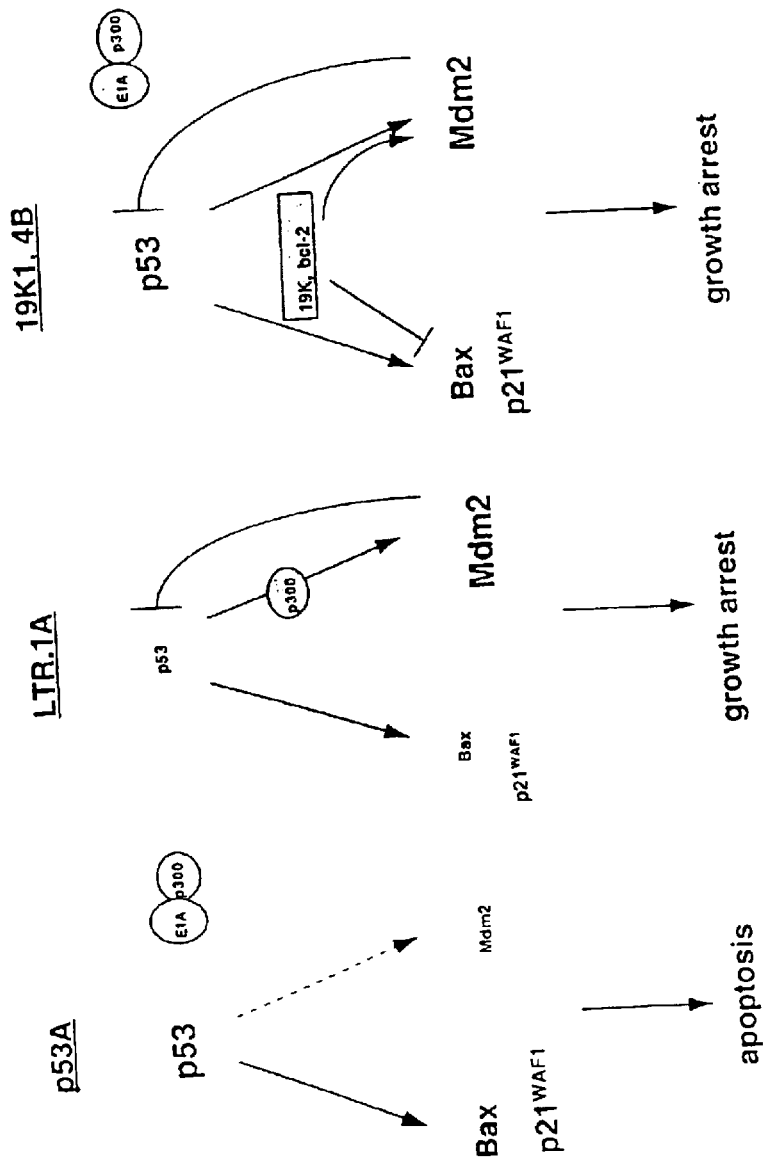
FIG. 18 is a schematic diagram illustrating the regulation of cell death in p53A, LTR.1A and 19K1/4B cells.

E1A+tsp53(val135) transformed p53A cells were unable to transactivate mdm2 as a result of E1A inhibition of p300, indicating that p53 requires p300 to transactivate mdm2. See FIG. 18. Furthermore, low Mdm2 levels in p53A cells relieve the negative-feedback regulation of p53 resulting in high p53 accumulation leading to apoptosis. In contrast, c-Myc+tsp53(val135) transformed LTR.1A cells transactivate Mdm2 in the absence of E1A inhibition of p300 (FIG. 18). Up-regulation of mdm2 inhibits p53 function and promotes p53 degradation (Haupt et al. 1997; Kubbutat et al. 1997), which in turn inhibits p53-mediated cell death resulting in growth arrest in LTR.1A cells. Cellular levels of p53 control the response of the cells such that lower levels of p53 induce growth arrest and higher levels induce apoptosis (Chen et al. 1996). Therefore, it may be concluded that p300 regulation of mdm2 levels determines whether the physiological response to p53 is growth arrest or apoptosis.

Interestingly, p300 cotransactivation is not required for the other p53-inducible genes Bax and p21$^{MAP1}$. It has previously been reported that E1A inhibits p53-mediated transactivation using promoter reporter assays (Steegenga et al. 1996). Our studies, however, demonstrate that E1A specifically inhibits endogenous mdm2 transactivation and not other p53-inducible genes such as bax and p21$^{WAF1}$. p300/CBP functions by interacting not only with p53, but also with other factors such as the TAFs (Thut et al. 1995), TBP (Abraham et al. 1993), CREB (Chrivia et al. 1993; Kwok et al. 1994), c-Jun/v-Jun (Bannister and Kouzarides 1995), c-Myb/v-Myb (Dai et al. 1996), c-Fos (Bannister and Kouzarides 1995) and others. p53-binding alone may not regulate the specificity of p300 cotransactivation, however, as numerous other cellular interactions may determine the specificity transactivation, which may explain differential regulation of p53-inducible genes by p300.

p300/CBP transcriptional coactivators have been shown to have histone acetyltransferase activity which can modify chromatin structure and enhance gene expression (Bannister and Kouzarides 1996; Ogryzko et al. 1996). Recently, p300 has been shown to acetylate p53 itself (Gu and Roeder 1997). The acetylation of p53 increases the binding activity of p53 to specific consensus sequences. In vivo, this activity may be required for facilitating p53 tetramer interactions with the DNA template, thereby promoting mdm2 transactivation.

Mutations that inactivate p300 have been described in colorectal and gastric carcinomas (Muraoka et al. 1996), which suggests that p300 functions as a negative regulator of cell growth. Missense mutations of p300 coupled with the deletion of the second allele of the gene were observed in these carcinomas. These observations suggest that inactivation of p300 may play a role in the development of cancer.

E1A inhibition of p300 transactivation may be one mechanism whereby this viral protein promotes cellular transformation. Moreover, p300 inactivation may render cells susceptible to agents that induce p53-mediated cell death such as UV and ionizing radiation. It is intriguing to speculate that acetyltransferase inhibitors specific for p300 may be used in cells that do not respond to chemotherapy regardless of having wild-type p53.

EXAMPLE II

As discussed previously, apoptosis is a genetically controlled process of cell suicide that plays a critical role in maintaining homeostasis and preventing disease. Disruption of apoptosis leads to impaired development, cancer, neurodegenerative and autoimmune diseases, and sustained viral infection. The regulation of apoptosis is a precarious balance between factors that promote survival and those responsible for initiating and executing cell death. One major advance toward the understanding of apoptosis regulation has been the characterization of the Bcl-2 family (White, E., 1996). This family consists of highly conserved proteins with opposing biological function. Anti-apoptotic Bcl-2 family members, such as Bcl-2 and Bcl-XL, inhibit apoptosis triggered by many circumstances, including TNF-$\alpha$, Fas, UV radiation, chemotherapeutic drugs, and growth factor/hormone withdrawal. In contrast, pro-apoptotic Bcl-2 family members, such as Bax, Bak, and Nbk/Bik, induce cell death in numerous model systems. The adenovirus E1B 19K protein cooperates with E1A in transformation assays and is a viral homologue of mammalian Bcl-2. Expression of E1B 19K, or Bcl-2, inhibits E1A-induced, p53-mediated apoptosis (Chiou et al, 1994; Han et al., 1996). Like Bcl-2, E1B 19K interacts with and antagonizes several pro-apoptotic family members, including Bax (Han et al., 1996), Nbk/Bik (Boyd, et al., 1995), and Bak. However, it is still unclear how these proteins affect cell survival or death and whether binding to proteins unrelated to the Bcl-2 family contribute to apoptosis or other cellular processes.

While there has been some debate concerning the biochemical function of E1B 19K and other Bcl-2 family members in the regulation of apoptosis, recent studies have revealed several possible mechanisms. Clearly, interactions between Bcl-2 family members play an integral part in the regulation of apoptosis and transformation. A common feature of the Bcl-2 family is the occurrence of protein-protein interactions between the anti- and pro-apoptotic proteins, the ratio of which controls the fate of the cell (Boise et al., 1993; Oltavai et al., 1993). Structural and biochemical studies of Bcl-2 family members point to a possibility that these proteins form ion channels (Antonsson et al., 1997). In addition, Bcl-2 family members bind to several unrelated proteins including R-ras, Nip-1-2-3, Ced-4-like proteins, Bag-1, Lamin A/C, and p28Bap31. Although the functional significance of some of these interactions are not yet known, these findings suggest that Bcl-2 regulates multiple signaling pathways that influence apoptosis.

There is growing evidence from several independent studies that Bcl-2-related proteins can trigger changes in gene expression which may or may not be related to their role in apoptosis regulation (Linette et al., 1996; Miyashita et al., 1997). Initial studies of E1B 19K mutant viruses raised the possibility that 19K functions to dampen transcriptional activation by E1A. Subsequently, it has been shown that E1B 19K and Bcl-2 alleviate the trans-repressive activity of E1A and p53. This derepression of transcription has been correlated with an up-regulation of one transcriptional target of p53, Mdm-2 as described in Example I. Since Mdm-2 inhibits p53 transcriptional activity and apoptosis, this model provides an alternative mechanism by which E1B 19K and Bcl-2 can regulate apoptosis. Furthermore, Bcl-2 family members may actually control several additional transcription factors including NF-κKB, NFAT (nuclear factor of activated T cells), c-Jun, and the glucocorticoid receptor, thus indicating that Bcl-2 and its related proteins can have multiple effects on gene expression that may contribute to apoptosis.

Compared to apoptosis regulation, relatively little is known concerning the gene regulatory function of the Bcl-2 family. In accordance with the present invention, a novel transcriptional repressor, Btf, which contributes to the modulation of transcription by Bcl-2 related proteins is provided. Btf was identified in a yeast-two hybrid screen against E1 B 19K and subsequently shown to also interact with Bcl-2 and Bcl-$X_L$. These Bcl-2 family members inhibit the translocation of Btf to the nucleus and abrogate its transcriptional activity. The data presented herein reveal that sustained over-expression of Btf induces apoptosis and suppresses transformation by E1A and E1B 19K or mutant p53. Thus, the interaction Btf provides yet another novel pathway by which the Bcl-2 family can regulate transcription and control apoptosis.

Yeast Two Hybrid Assay

Figure 19A:
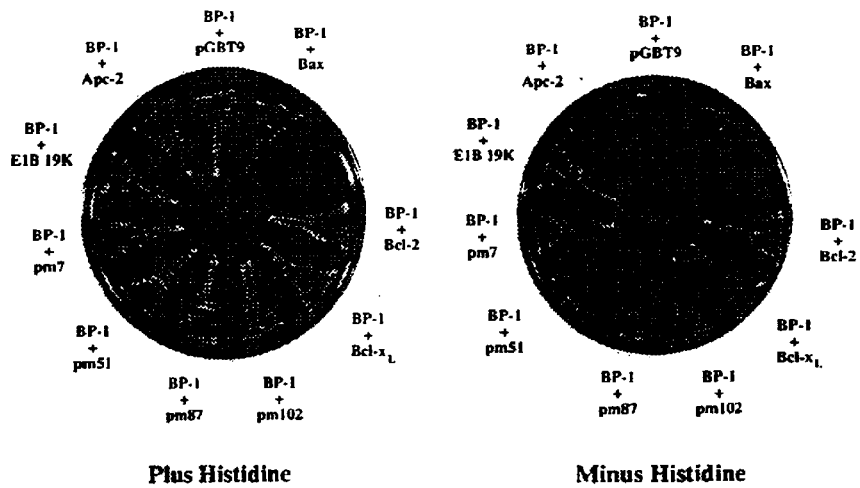
FIGS. 19A and 19B are growth profiles of transformed yeast cells demonstrating that BP-1 interacts with E1B 19K in yeast. The yeast two-hybrid assay was utilized to demonstrate binding between BP-1 and E1B 19K. Growth in the presence of histidine indicates that both plasmids can be expressed in yeast, and growth in the absence of histidine demonstrates an interaction between the two proteins. Apc-2 represents an irrelevant hydrophobic protein used as a negative control. The specificity of the interaction between BP-1 and E1B 19K was tested using related proteins (Bcl-2, Bcl-XL, and Bax) as well as missense mutants of E1B 19K (pm7, pm51, pm87, and pm102, FIG. 19A.

In order to identify novel cellular proteins that interact with E1B 19K, we screened a HeLa, cDNA library using the yeast two-hybrid assay. The library was constructed in the pGAD-GH plasmid in which the cDNA sequences were fused to the GAL-4 activation domain, and the bait gene, E1B 19K, was fused to the GAL-4 DNA-binding domain in the pGBT9 vector (Han et al., 1996). The plasmids were transformed into the YGH1 yeast strain and screened for GAL-4 inducible phenotypes, namely growth in the absence of histidine and production of β-galactosidase. Three million transformants were screened yielding seven clones (BP-1 to B.P-7) that specifically interacted with 19K and not with the pGBT9 vector alone or with an irrelevant protein, Apc-2. BP-2, -3, and -4 were previously reported as Lamin A/C, Bax, and Nbk/Bik, respectively. Here, we describe one of the novel E1B 19K associated proteins, BP-1. A 1.5 kB cDNA containing bp-1 was isolated seven times during the two-hybrid screen. Since Bcl-2 family members are highly homologous and frequently interact with the same cellular proteins, we tested BP-1 for interaction with Bcl-2-related apoptosis regulators. In addition to binding E1B 19K, BP-1 interacted with other related proteins, Bcl-2 and Bcl-XL, but not to the pro-apoptotic family member, Bax (FIG. 19A).

The interaction between anti- and pro-apoptotic Bcl-2 family members generally occurs via their conserved domains, designated Bcl-2 homologous regions 1, 2, 3, and 4 (BH1, BH2, BH3, and BH4). BH1-3 are in close proximity forming a hydrophobic cleft that is required for dimerization. To determine the regions of E1B 19K that are required for interaction with BP-1, we tested its ability to bind a series of E1B 19K missense and deletion mutants (See FIGS. 19A, B & C). These mutants have been characterized previously for binding to other E1B 19K binding proteins, including Bax, Nbk/Bik, Lamin A/C, and Ced-4. Thus, these experiments allow us to compare the binding requirements within the E1B 19K protein against other 19K-associated proteins.

Figure 19B:
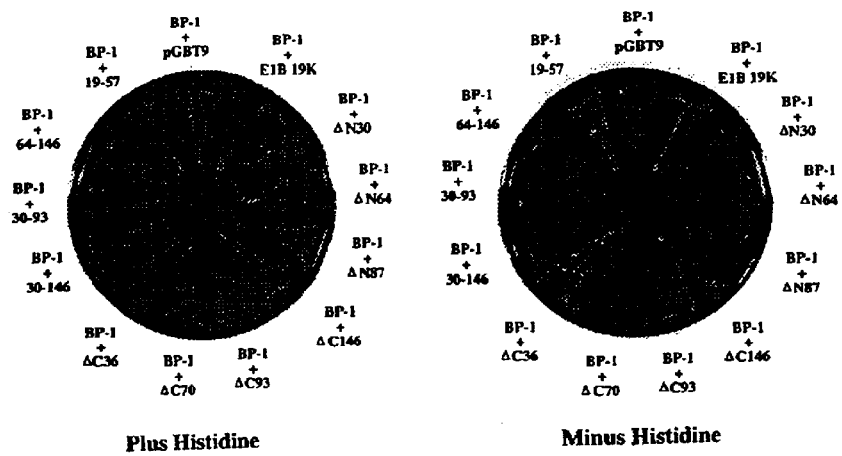
Figure 19C:
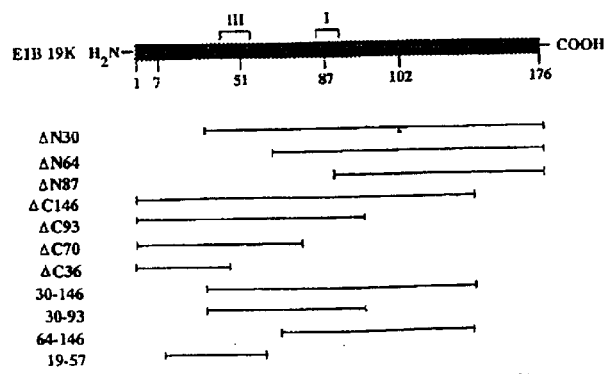
FIG. 19C is a schematic representation of E1B 19K showing the missense and deletion mutants tested in the two-hybrid assay. Regions I and III indicate the locations of the Bcl-2 homology domains, BH1 and BH3. E1B 19K does not contain recognizable BH2 or BH4 domains.

The E1B 19K protein may be divided into three regions: a moderately conserved N-terminus which includes BH3, a highly Conserved central region containing BH1, and a poorly conserved C-terminus. It is important to note that most of the deletion mutants tested ΔN30, ΔN64, ΔN87, ΔC93, ΔC70, 30–146, 30-93, and 64-136) failed to interact with BP-1 or with Bax, Nbk/Bik, and Lamin A/C, and that this may be due to abnormal protein folding or masking of the binding site(s) (FIG. 193). Like Bax, Nbk/Bik, and Lamin A/C, binding of BP-1 was retained in C146 which contains both BH1 and BH3. The small E1B 19K fragment 19-57 containing only BH3 was also able to bind BP-1 (FIG. 19B). This fragment is also sufficient for binding to Bax as well as Ced-4. Surprisingly, we found that another small region of E1B 19K, C36, also retained binding to BP-1 (FIG. 19B). This region did not bind to other E1B 19K-associated proteins, Bax, Nbk/Bik, Lamin A/C, or Ced-4. The binding of BP-1 with the E1B 19K mutants C36 and 19-57, suggests that the region of 19K immediately adjacent to BH3 (19–36) may be: sufficient for the interaction. This would represent a unique domain that contributes to protein-protein interactions and may correspond to the E1B 19K BH4, although homology is weak.

We further addressed the binding specifications for BP-1 using several point mutants (pm7, pm51, pm87, and pm102) that have previously been analyzed for interaction with E1B 19K-associated proteins as well as for their ability to inhibit apoptosis. While pm7 and pm102 retained ability to bind to BP-1, substitution of either phenylalanine for serine at position 51 (pm51) or glycine for alanine at position 87(pm87) resulted in a loss of binding (FIG. 19A). The lack of binding with pm51 is consistent with a role of BH3 in the interaction between E1B 19K and BP-1. Although the loss of binding with pm87 might suggest a role in BH1, it should be noted that the glycine residue at position 87 is absolutely conserved within the Bcl-2 family and is located in an integral region adjacent to the hydrophobic cleft which serves as the BH3 binding pocket. Therefore, the pm87 mutant may interfere with the BH3 region and/or result in a highly misfolded protein. Indeed, pm87 is generally defective in binding and at inhibiting apoptosis. Thus, taken together, the mutational analyses indicate that the BH3 and the adjacent N-terminal sequences (possibly BH4) may play a more critical role in the interaction with BP-1. This binding profile overlaps but is distinct from that for Bax and Nbk/Bik and corresponds to a region of E1B 19K that is required for inhibition of apoptosis.

Characterization of BP-1

Figure 20A:
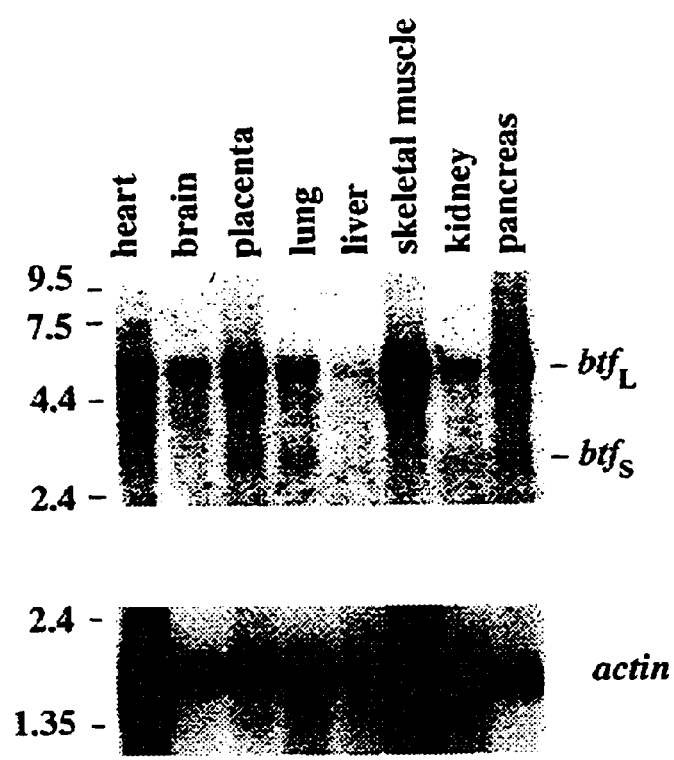
FIGS. 20A and 20B are autoradiographs showing the results of Northern blot analysis performed to determine btf expression in various tissues (FIG. 20A), and cancer cell lines (FIG. 20B). Two transcripts were observed at 5 kB ($btf_L$) and 3 kB ($btf_S$). These transcripts appeared to be ubiquitously expressed, except that btf was not detected in Raji cells derived from Burkitt's lymphoma. Lower panels depict β-actin expression to assess the quality of the RNA and to control for loading efficiency.

To determine the size and distribution of bp-1, we performed a Northern blot using poly A$^+$ RNA prepared from various tissues. Two transcripts were detected at 5 kB and 3 kB which appeared to be ubiquitously expressed, although only low levels were detected in the liver (FIG. 20A). The larger transcript appeared to be expressed more abundantly than the shorter form. Since the largest fragment of bp-1 obtained in the two-hybrid screen was only 1.5 kB, we sought to recover full-length cDNAs corresponding to bp-1. Using conventional library screening techniques along with database searches we were able to identify both full length transcripts which were named btf (Bcl-2-associated transcription factor). The 3 kB transcript, btf$_S$, was isolated by screening a HeLa λ-cDNA library. The 3'-end of btf$_S$ was identical to bp-1 except that it was missing 147 base pairs (bp) within the predicted coding sequence. While the 5 kB transcript, btf$_L$, could not be recovered from the λ screen, it was identified as a full-length expressed sequence tag (EST) within GenBank (accession # D79986) that was isolated from the human KG-1 cell line. Unlike btf$_S$, btf$_L$ did contain the 147 bp region present in bp-1. Based on sequence comparisons from GenBank with btf$_S$, we found that the remainder of the coding sequences between btf$_S$ and btf$_L$ were the same, and the large size difference between the transcripts results from different 3'-untranslated regions (UTRs).

The EST encoding Btf$_L$ was utilized to identify the sub-chromosomal location of btf. However, it remains to be determined whether btf$_L$ and btf$_S$ are formed from separate genes or whether they are generated by alternative splicing of the same gene. Using the UniGene collection assessed through National Center for Biotechnology Information (NCBI), we found a 137 bp PCR fragment within the 3'-UTR of the EST (dbSTS entry G20483) that mapped to chromosome 6 between markers D6S292 and D6S1699. These markers correspond to 6q22-23, a locus with a high frequency of deletions in tumors, particularly lymphomas and leukemias (Mitelman, 1995). Thus, the locus of btf correlates with a chromosomal region that may contain a tumor suppressor gene.

Figure 20B:
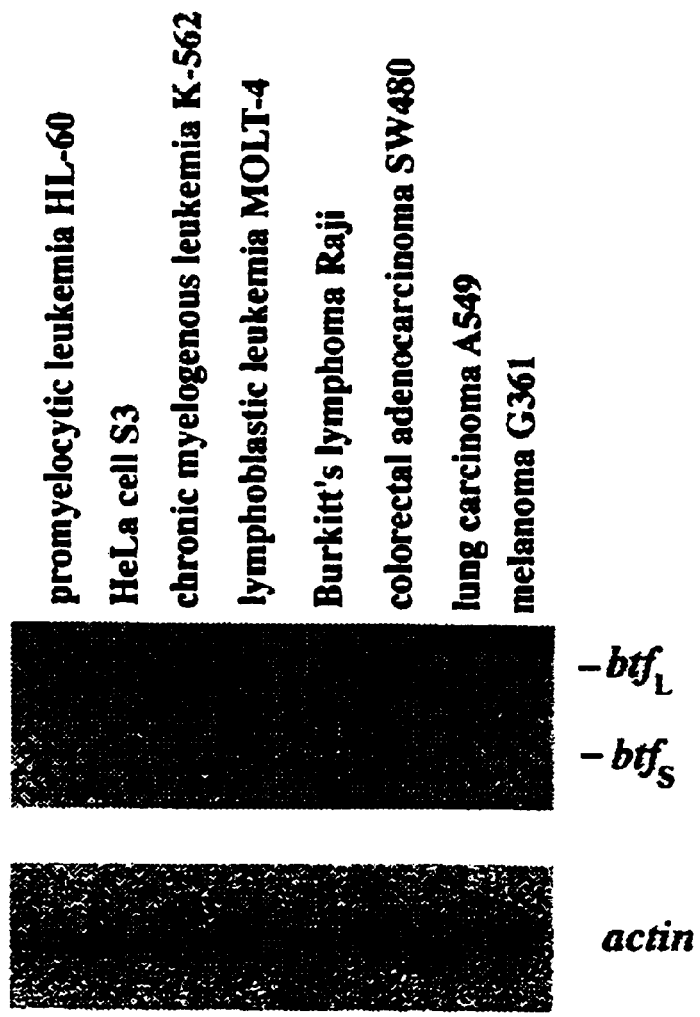

To test whether btf is actually deleted in tumors, we performed a Northern blot using mRNA prepared from several human cancer cell lines. While both transcripts of btf were observed in most cell lines tested, they appeared to be less abundant than normal cells and btf was not detected in Raji cells which were derived from Burkitt's lymphoma (FIG. 20B). Indeed, Raji cells were the one cell line tested with known 6q deletions. The Northern blot data was therefore consistent with the chromosomal mapping of the gene. Thus, loss of btf may actually contribute to tumor formation in these cells.

Figure 22:
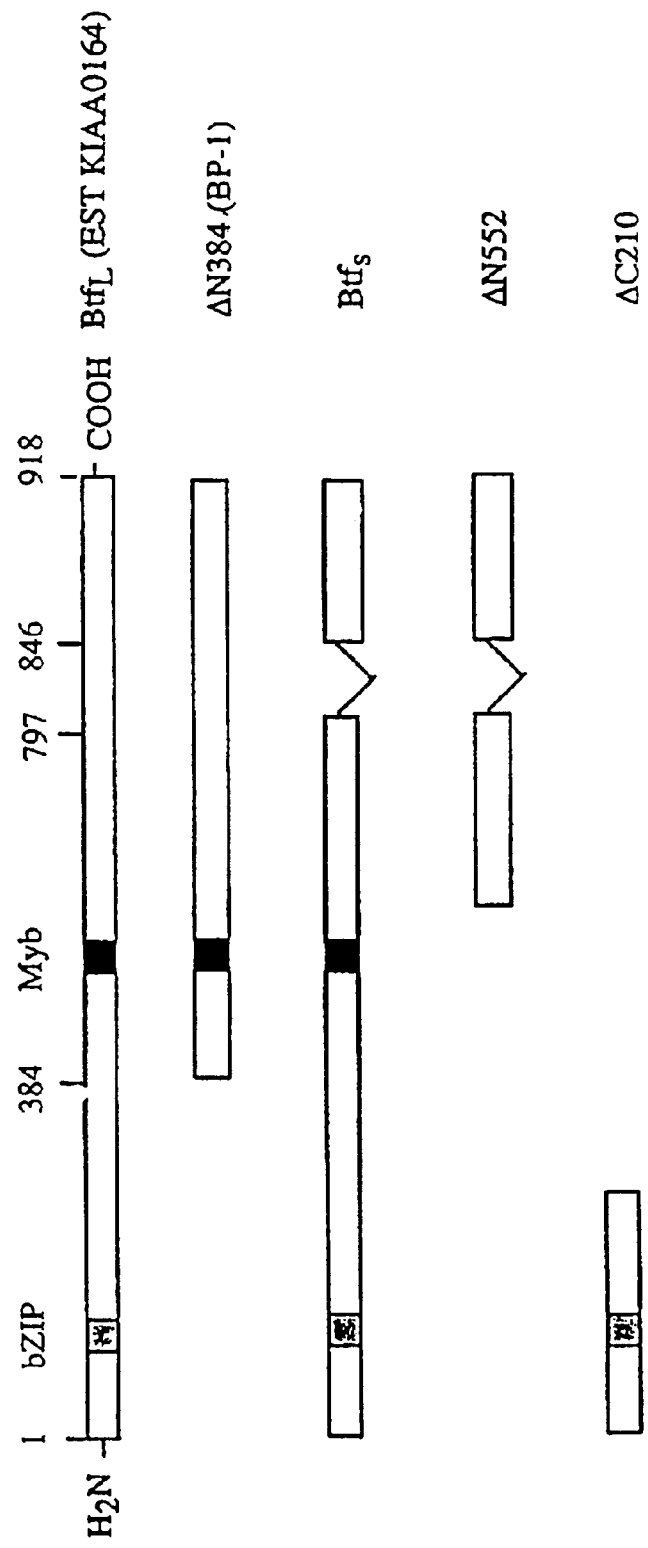
FIG. 22 is a schematic representation of the Btf variants and deletion mutants used to characterize Btf function. The gray and black boxes represent the locations of putative bZIP and Myb-DNA binding domains, respectively. BP-1 (N384), identified in the yeast two-hybrid screen for E1B 19K binding proteins, contains residues 384–918 of $Btf_L$. Deletion mutants of $Btf_S$, N552 and C210 were used in transcriptional reporter assays to determine the regions of $Btf_S$ that contribute to transcriptional repression.

The primary amino acid sequence encoded by the long and short forms of btf are compared in FIG. 21. Btf$_L$ is 918 amino acids and has a predicted molecular mass of 106 kDa, whereas Btf$_S$ is missing 49 amino acids near the carboxyl terminus (amino acids 797–846 of Btf$_L$) and has a predicted size of 101 kDa. See FIGS. 21 and 22. The original bp-1 clone encodes for amino acids 384–918 of Btf$_L$ (Btf ΔN384) which is slightly more than half of the full-length protein (FIG. 22). In general, the 49 amino acid region specific to Btf$_L$ and ΔN384 contains highly charged residues (48%), but the significance of this region is not known. Both Btf$_S$ and Btf$_L$ were able to bind E1B 19K in the yeast two-hybrid assay (data not shown) While the overall protein sequence of Btf is not significantly homologous to other known proteins, searches for conserved motifs using the PROSITE database revealed two nuclear localization sequences (NLS) (FIG. 21) as well as putative DNA-binding domains (FIG. 22). There was 88% homology to the basic zipper (bZIP) DNA-binding domain between amino acids 110 and 126, and 80% homology to the Myb DNA-binding domain within amino acids 522 and 531 of Btf (FIG. 22).

Figure 23:
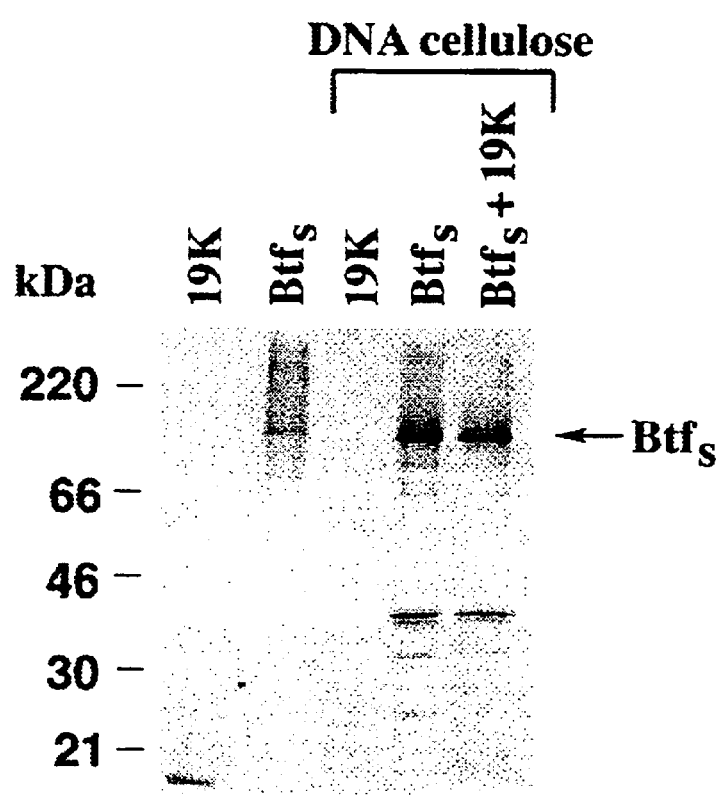
FIG. 23 is an autoradiograph showing $^{35}$[S]-methione labeled in vitro translated Myc-$Btf_S$, and E1B 19K prepared using the TNT T7 reticolocyte lysate system and incubated with native DNA-cellulose in NETN buffer for 2 hrs. The data show that $Btf_S$ binds to DNA-cellulose in vitro. Samples were washed five times in NETN and the proteins were resolved by 17% SDS-PAGE. Immunoprecipitated proteins (lanes 1 and 2) were analyzed to confirm the presence of the in vitro translated products.

Btf$_S$ is a Nuclear DNA-Binding Protein That is Sequestered by the Bcl-2 Family Since btf$_S$, but not btf$_L$, was isolated from the HeLa library, we concentrated our functional assays using the shorter variant. Btf$_S$ was cloned into the pcDNA3 vector with a Myc epitope for min vitro translation and mammalian expression. The protein sequence of Btf$_S$ suggested that it may bind to DNA. To test this hypothesis $^{35}$[S]-labeled in vitro translated Myc-Btf$_S$ was incubated with native DNA-cellulose. DNA-binding was detected with Btf$_S$ but not with E1B 19K used as a negative control (FIG. 23). The strength of the interaction was comparable to a known transcription factor, Msx-1, and was not competed by RNA (data not shown). In vitro translated E1B 19K and Bcl-2 (data not shown) did not inhibit the ability of Btf$_S$ to bind to DNA suggesting that the binding sites for DNA and E1B 19K/Bcl-2 are in distinct domains within Btf$_S$. Indeed, comparison of the putative DNA-binding domains and the BP-1 (Btf ΔN384) protein which is sufficient for binding to the Bcl-2 family members is consistent with there being two separate domains.

Figure 24:
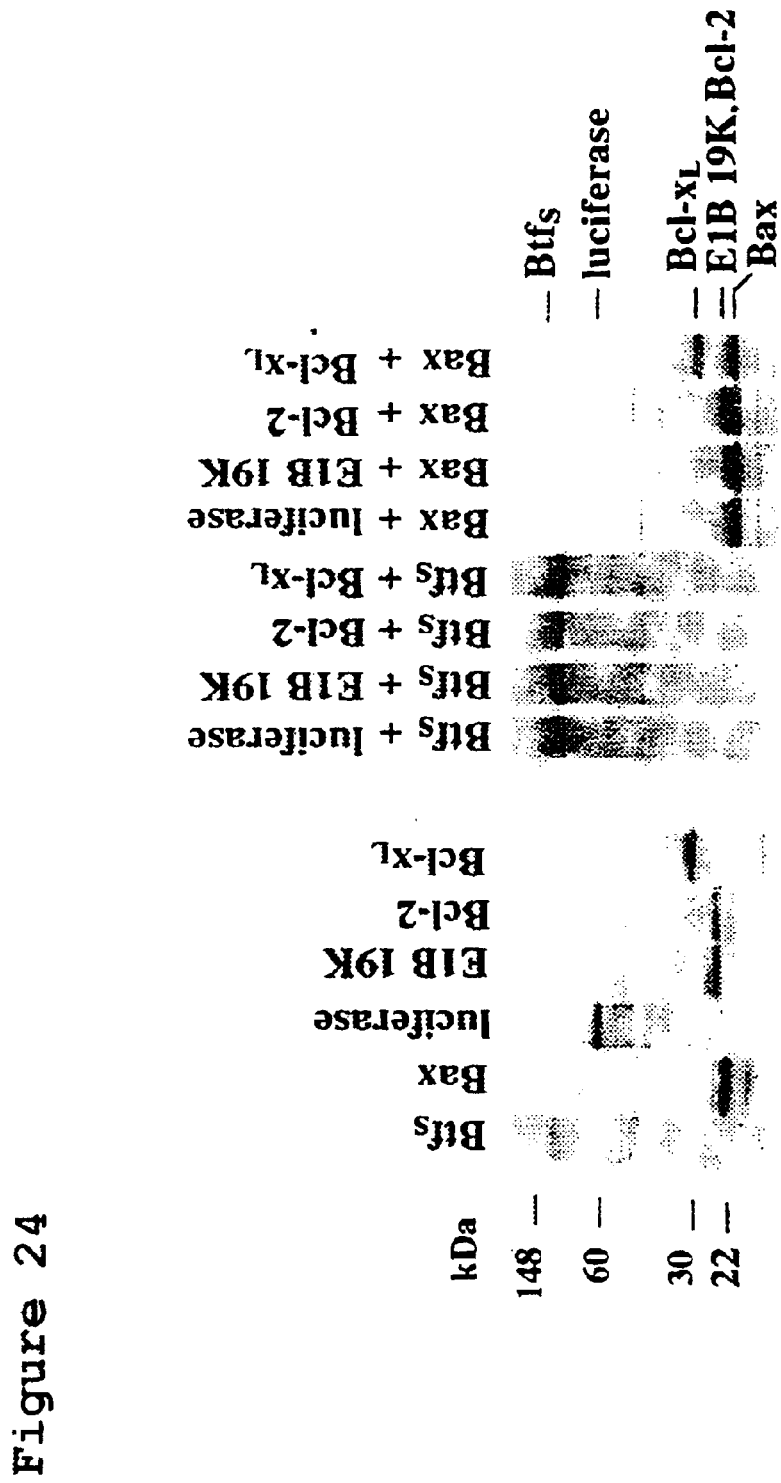
FIG. 24 is an autoradiograph showing in vitro interactions between $Btf_S$ and anti-apoptotic Bcl-2 family members. $^{35}$[S]-labeled in vitro translated Myc-$Btf_S$ or Myc-Bax was combined with V5/His-E1B 19K, Bcl-2, Flag-Bcl-$x_L$, or luciferase prepared using the TNT T7 reticolocyte lysate system. The proteins were immunoprecipitated with anti-Myc monoclonal antibody in NETN buffer for 1.5 hrs followed by protein A-sepharose for 0.5 hr. Samples were washed in NETN buffer, resolved by 14% SDS-PAGE and visualized by autoradiography. In addition, 1 μl of each of translation reaction was analyzed to verify that equal amounts of proteins were used in the binding assay.

To confirm the association between Btf$_S$ and Bcl-2 family members we performed an in vitro binding assay. $^{35}$[S]-labeled in vitro translated Myc-Btf$_S$ or Myc-Bax, used as a positive control, was combined with E1B 19K, Bcl-2, and Bcl-XL. Immunoprecipitation with an antibody against Myc revealed that Btf$_S$ bound to all three of the anti-apoptotic Bcl-2 family members, but not to luciferase used a negative control (FIG. 24). However, the strength of these associations were weaker than those with Bax (FIG. 24). These results support the data obtained from the yeast two-hybrid assay.

Figure 26:
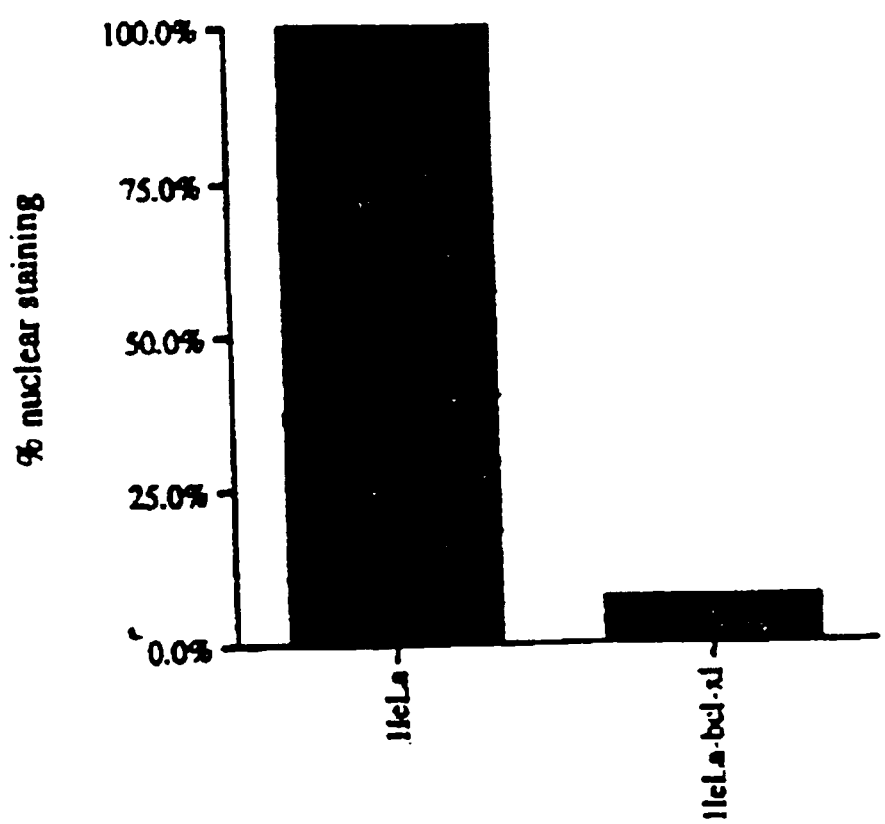
FIG. 26 is a graph showing the percent of nuclear $Btf_S$ expression ($Btf_S$/total $Btf_S$) in HeLa cells expressing Bcl-$X_L$ transfected with pcDNA3-Myc-$Btf_S$ and stained 24 hours post-transfection against Myc.

To examine the biological of Btf$_S$ in vivo, we attempted to express the tagged protein in HeLa cells. While were unable to obtain stable expression of Btf$_s$ even using an inducible promoter, transient transfection did produce low levels of Btf$_S$. Although the levels of Btf$_S$ were not high enough to detect by Western blot analysis of whole cell extracts (data not shown) which would allow us to examine whether Btf$_S$ could co-immunoprecipitate with Bcl-2 family members, we were able to visualize Btf$_S$ by immunofluorescence. Its expression was confined to the nucleus and was present in roughly 4% of the cells (FIG. 25). This was consistent with the DNA-binding activity, but not with the established localization of Bcl-2-like proteins which are generally found associated with membrane structures, particularly the mitochondria, endoplasmic reticulum, and nuclear envelope. Unlike other Bcl-2 family members, E1 B 19K is not normally present in the mitochondria, but rather predominantly localized to the nuclear envelope. However, since the Bcl-2 family can act by sequestering proteins we checked whether E1B 19K, Bcl-2, and Bcl-X$_L$ could alter the subcellular localization of Btf$_S$. First, E1B 19K and Bcl-2 were co-transfected with Myc-Btf$_S$. The cells were fixed 24 hours post-transfection and then double stained for the Myc epitope present on Btf$_s$ (rhodamine) and either E1B 19K or Bcl-2 (fluorescein). While the percent of Btf$_S$-positive cells was similar to that when it was transfected by itself, the subcellular localization was altered. Btf$_S$ co-localized with E1B 19K and Bcl-2 within the cytoplasm and nuclear periphery in almost all co-expressing cells (FIG. 25) Subsequent experiments were performed to determine if Bcl-x$_L$ could also sequester Btf$_S$ since these proteins also bound in the yeast two-hybrid assay and in vitro. We could not co-stain for Btf$_S$ and Bcl-X$_L$ with available antibodies, so we developed a stable HeLa cell line expressing Bcl-x$_L$ and stained for Btf$_S$ using the antibody against the Myc epitope. While control HeLa cells contained 100% nuclear Btf$_S$ expression, only 7% of the Btf$_S$-positive cells in the HeLa-Bcl-x$_L$ cell line displayed nuclear Btf$_s$ staining and almost all of the Btf$_S$ staining was in the cytoplasm in a pattern similar to Bcl-x$_L$ (FIG. 26). The few cells expressing nuclear Btf$_L$ may be accounted for by the variable levels of Bcl-X$_L$ observed in this cell line and/or an incomplete ability of Bcl-X$_L$ to sequester Btf$_S$. Nevertheless, it is in clear contrast to the parental HeLa cells where the expression of Btf$_S$ was completely nuclear. These results suggest that E1B 19K, Bcl-2, and BCl-XL can alter the localization, and therefore apparently, the function, of Btf$_S$.

Btf$_S$ Represses Transcription Which is Inhibited by the Bcl-2 Family

Since Btf$_S$ was shown to bind DNA, we checked whether it could modulate transcription. We first performed a one-hybrid assay in yeast by generating a fusion protein of Btf$_S$ with the GAL-4 DNA-binding domain in the pGBT9 vector. If Btf$_S$ contained a trans-activation domain one would expect that the adjacent activation and DNA-binding domains would lead to GAL-4-inducible phenotypes in yeast. Growth was not detected in the absence of histidine suggesting that Btf$_S$ does not contain a transcriptional activation domain (data not shown). However, it remains possible that Btf$_S$ requires mammalian co-factors in order to activate transcription or that Btf$_S$ represses, rather than activates, transcription.

Figure 27:
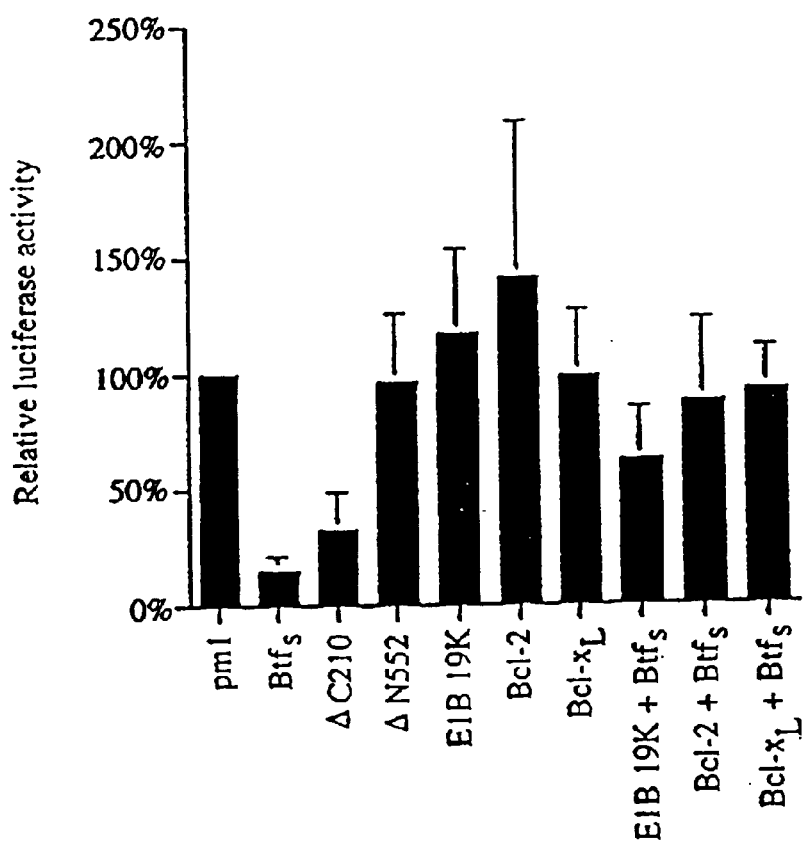
FIG. 27 is a graph showing the results of a reporter assay demonstrating that $Btf_S$ is a transcription repressor and is inhibited by Bcl-2-like proteins. HeLa cells were transfected with 2.5 μg of the reporter construct (luciferase construct containing GAL-4 DNA-binding sites within its promoter), 2.5 μg of GAL-4 DNA-binding domain fusion genes (pm1-$Btf_S$, Δ-N552, and Δ-C210 or empty pm1 vector control), and 2.5 μg of bcl-2 family gene (pCMV-E1B 19K, pcDNA3-Bcl-2, or pcDNA3-Flag-Bcl-$x_L$, or empty pcDNA3 vector control). Cells were harvested 24 hours post-transfection and the luciferase activity was measured in a scintillation counter using the luciferase substrate, luciferin. Values were normalized for protein concentrations measured by a Bradford assay and graphed as a percent of the negative control (empty pm1 vector). The experiment was repeated six times and the high and low values for each sample were dropped. Bars indicate standard deviation, n=4.

To address these issues, Btf$_S$ was cloned into a mammalian expression vector (pm1) containing the GAL-4 DNA binding domain. Transcriptional activity was monitored using a reporter construct containing GAL-4 promoter sites. Transient expression of pm1-Btf$_S$ with the luciferase reporter led to nearly a 10-fold decrease in transcription compared to an empty pm1 vector control (FIG. 27). This effect is comparable to the trans-repressive activity of other proteins, such as p53 and Msx-1. Two deletion mutants of Btf$_S$, ΔN522 (amino acids 522–918 without residues 797–846 and ΔC210 (amino acids 1–210) were also cloned into pm1 to determine the general regions that may contribute to transcriptional repression (FIG. 22). Both deletion mutants of Btf$_S$ were detectably expressed in HeLa cells to levels comparable with wild-type Btf$_S$ (data not shown). While Btf-$_S$ ΔN552 was not able to repress transcription, the ΔC210 mutant was sufficient for repression and nearly as potent as full-length Btf$_S$ (FIG. 27). Interestingly, this fragment which contains the bZIP homology segment is also rich in serine and glycine residues, a feature that is present in other transcriptional repressors.

Since the Bcl-2-like proteins were capable of sequestering Btf$_S$ in the cytoplasm, we hypothesized that they may also block the ability of Btf$_S$ to repress transcription. To test this possibility we co-transfected E1B 19K, Bcl-2, and Bcl-X$_L$ with pm1-Btf$_S$ and the luciferase reporter construct. In the control samples, none of the Bcl-2 family of proteins had a significant effect on transcription of the luciferase reporter (FIG. 27). However, transfection of any of the three Bcl-2 family members (E1B 19K, Bcl-2, and Bcl-X$_L$), but not the empty pcDNA3 vector, abrogated Btf$_S$-mediated transcriptional repression. These data suggest that E1B 19K, Bcl-2, and Bcl-X$_L$ inhibit Btf$_S$ trans-repression, probably by binding to and sequestering Btf$_S$ in the cytoplasm.

Sustained Expression of Btf$_S$ Inhibits Transformation

Figure 28A:
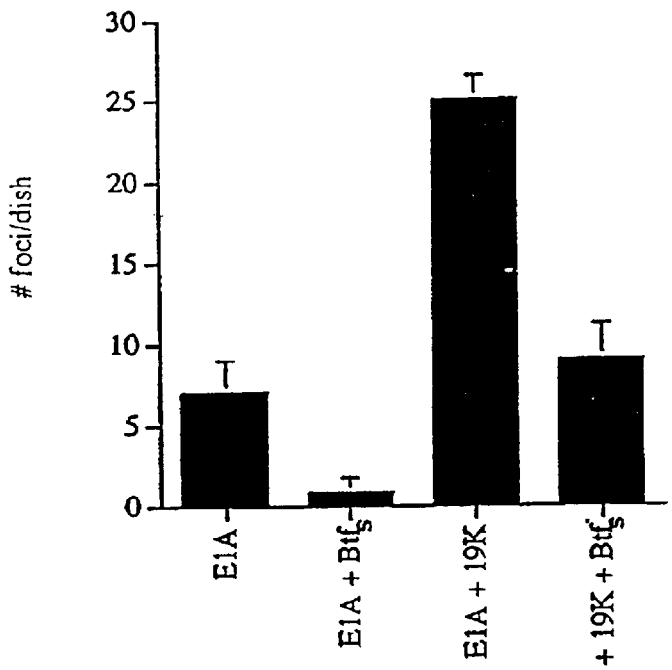
FIGS. 28A and 28B are a pair of graphs showing that $Btf_S$ inhibits transformation by E1A and E1B 19K (FIG. 28A) or p53DD (FIG. 28B). Primary baby rat kidney (BRK) cells were transfected with carrier DNA along with linearized test DNA (15 μg pCMV-E1A, 15 μg pCMV-E1B 19K or pCMV-p53DD, and 45 μg pcDNA3-Myc-$Btf_S$). DNA concentrations were kept constant using appropriate empty vectors. The cells were cultured for 3 to 4 weeks and then stained with Giemsa. Foci were counted from four dishes per condition. Bars indicate standard deviation, n=4.
Figure 28B:
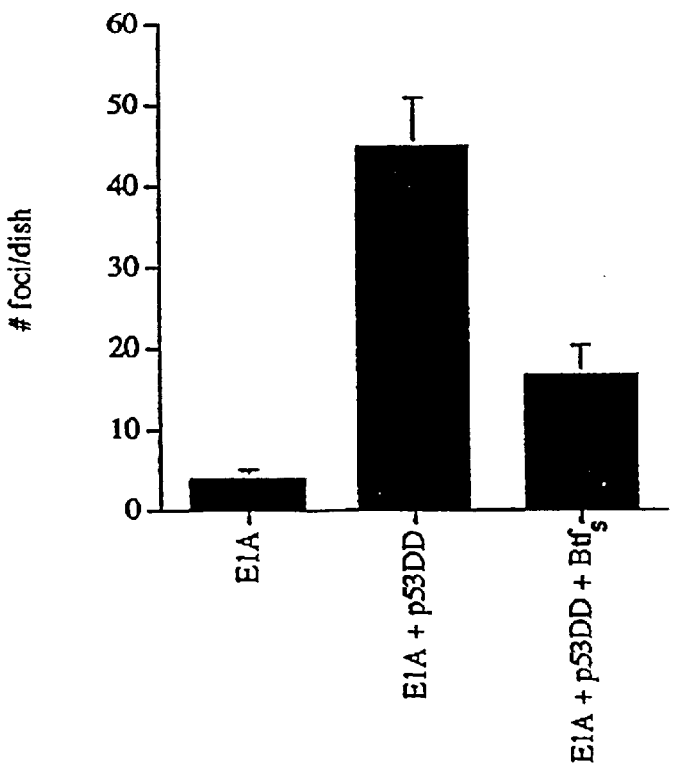

Transfection of the adenovirus E1A gene along with E1B 19K or bcl-2 in primary BRK cells induces transformation as a consequence of dual proliferative and anti-apoptotic signaling. Expression of E1B 19K/Bcl-2 binding proteins, such as Bax and Nbk/Bik, antagonizes the anti-apoptotic signal and causes a reduction in foci formation. To determine if Btf$_S$ could also antagonize the ability of E1B 19K to transform primary cells, we transfected E1A and E1B 19K, with and without Myc-Btf$_S$, into primary BRK cells. Btf$_S$ caused a 64% reduction in foci formation mediated by E1A and E1B 19K (FIG. 28A). This suggests that interaction between Btf$_S$ and E1B 19K inhibits 19K function in vivo and/or Btf$_S$ is capable of suppressing transformation independent of 19K. The reduction in foci formation by Btf$_S$ and E1A compared to E1A alone suggested the later is possible (FIG. 28A). However, we tested whether Btf$_S$ could inhibit another transforming signal, E1A with p53DD. pS3DD is a p53 deletion mutant that contains the C-terminal oligomerization domain and functions in a dominant-negative fashion to inhibit p53-mediated apoptosis and growth arrest. Since p53DD blocks both of these processes, it produces a very potent transforming signal. Here we show that expression of Btf$_S$ was capable of repressing foci formation by E1A and p53DD by about 60%, suggesting that btf$_S$ may act as a general suppressor of transformation (FIG. 28B).

Btf$_S$ Functions to Induce Apoptosis

To further characterize the transformation suppressing activity of Btf$_S$ we tested the effect of its expression on apoptosis and cell cycle progression. Attempts to generate stable BRK or HeLa cell lines expressing Btf$_S$ failed, indicating that sustained Btf$_S$ expression is incompatible with either cell proliferation or viability. To monitor Btf$_S$ expression in transient assays, the cDNA was cloned into the pIRES-EGFP vector which provides co-expression of Btf$_S$ and the enhanced green fluorescent protein (EGFP) marker. HeLa cells were transiently transfected and the cells were harvested 48 and 72 hours post-transfection. The cell cycle kinetics were analyzed following propidium iodide staining by FACS analysis. Since EGFP staining with Btf$_S$ was not detectable until 48 hours post-transfection, we were unable to characterize the cell cycle characteristics at the earlier time points. The levels of EGFP expression and the cell cycle kinetics at 48 and 72 hours are shown in Table 1. At 48 hours post-transfection there were only 19.5% EGFP-positive cells in the presence of Btf$_S$, whereas there were 61.2% positive cells in the control pIRES-EGFP empty vector. The FACS analysis demonstrated that Btf$_S$ led to an increase in percent of subG$_{0/1}$ cells from 3.4% to 15.8% indicating an increase in cell death. No other obvious changes in cell cycle parameters were observed at this time point.

Figure 29:
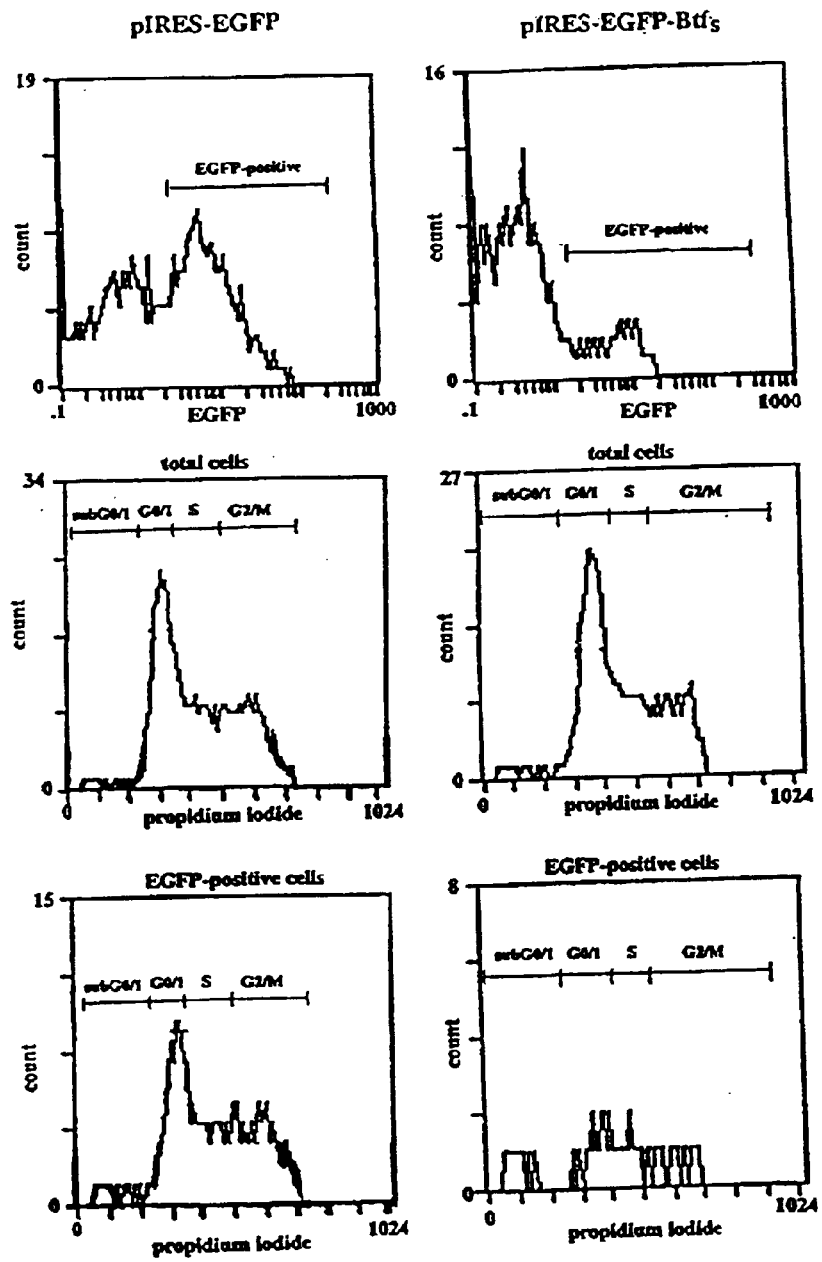
FIG. 29 shows a representative FACS scan from Table 1 at 72 hours post-transfection of pIRES-EGFP-$Btf_S$ and the empty pIRES-EGFP vector into HeLa cells The data reveal that $Btf_S$-mediated cell death occurs by apoptosis. Cell cycle kinetics from propidium iodide staining are shown for the total cell population as well as the EGFP-positive cells.

To test whether E1B 19K could inhibit this cell death, we co-transfected pIRES-EGFP-Btf$_S$ with pCMV-E1B 19K. E1B 19K inhibited Btf$_S$-mediated cell death at 48 hours as indicated by an increase in the number of EGFP expressing cells from 19.5% to 34.3% and fewer subG$_{0/1}$ cells (15.8% to 10.1%) (Table 1). Thus, E1B 19K expression abrogated cell death induced by Btf$_S$. At 72 post-transfection the amount of cell death triggered by Btf$_S$ increased and could no longer be inhibited by E1B 19K. In the presence of Btf$_S$ there were only 13.2% EGFP positive-cells, 29.1% of which were represented in the subG$_{0/1}$ peak (FIG. 29). The 72 hour time point also revealed a decrease in the G$_2$/M peak with Btf$_S$ (16.7%) compared to the control vector (40.6%). The change in G$_2$/M by Btf$_S$ may be an indication that cells are exiting from these phases of the cell cycle to go into apoptosis.

Interestingly, we also observed a decrease in the G$_2$/M peak with E1B 19K in the absence of Btf$_S$. At 72 hours post-transfection there was a change in the number of cells in G$_2$/M from 40.6% with the control vector to 14.8% in E1B 19K transfected cells. Changes in cell cycle progression by the anti-apoptotic Bcl-2 family members have been observed previously, such that generally they produce a decrease in cell cycle progression. While others have shown that Bcl-2 causes an increase in G$_{0/1}$, here we show that E1B 19K causes an decrease in G$_2$/M. Thus, these results may reflect a difference in the mechanism between the cell cycle regulation by E1B 19K and other related proteins.

Figure 30:
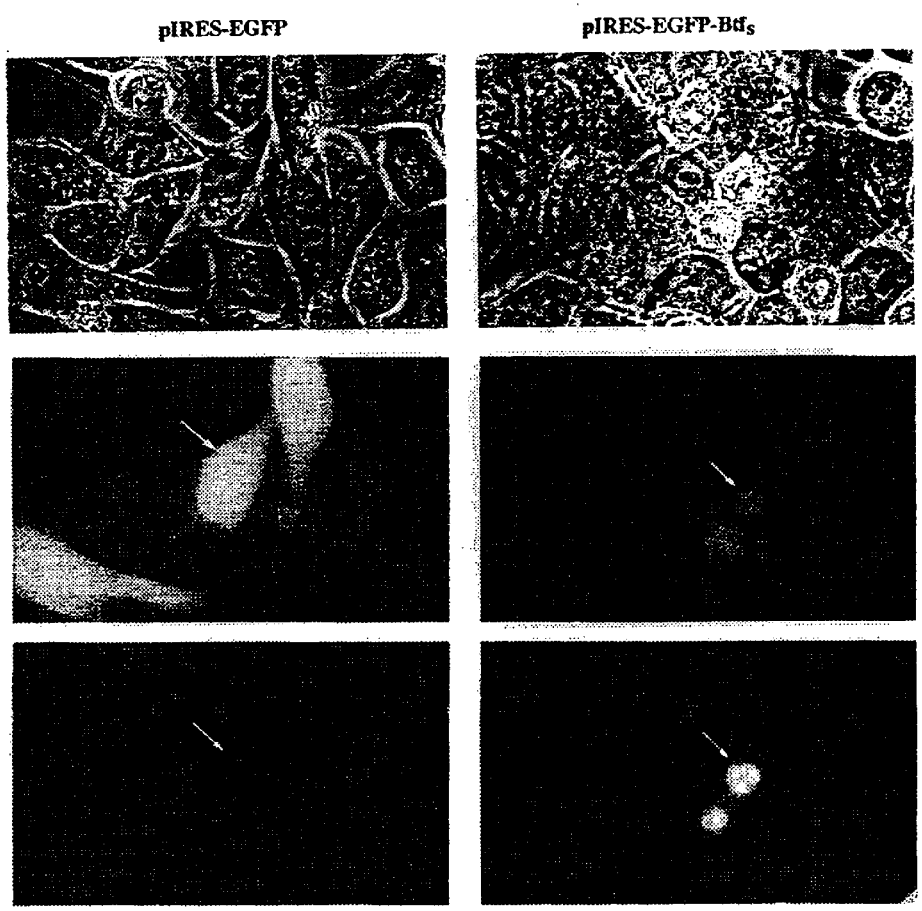
FIG. 30 is a series of micrographs showing transfected cells incubated with Hoechst dye 72 hours post-transfection to visualize the DNA. Cells transfected with pIRES-EGFP-$Btf_S$ (right side) were compared to control pIRES-EGFP (left side). Arrows for each set correspond to the same cell visualized with brightfield (top), EGFP (green; middle), and Hoechst dye (blue; bottom). The presence of condensed chromatin in the presence of $Btf_S$ indicates cell death by apoptosis. The cells were photographed with an original magnification of 1000×.

Cell death has been classified as either necrosis or apoptosis, where necrosis is considered a passive process of cell death associated with trauma, and apoptosis is a genetically programmed active response leading to cell suicide. Unlike necrosis, apoptosis involves morphological changes such as chromatin condensation, DNA fragmentation, and cytoplasmic blebbing. To test whether the increase in subG$_{0/1}$ cells by Btf$_S$ was due to apoptosis, we examined the nuclei of EGFP-positive cells with Hoechst dye 72 hours post-transfection. Chromatin condensation observed by this approach would be one indication of apoptosis. HeLa cells transfected with the empty pIRES-EGFP vector showed EGFP stained cells with normal nuclei. However, in cells transfected with pIRES-EGFP-Btf$_S$, the EGFP-positive cells had condensed chromatin staining, indicating that they were dying by apoptosis (FIG. 30 Taken together, these results suggest that Btf$_S$ can function to promote apoptosis which may account for its ability to suppress transformation. E1B 19K can inhibit Btf$_S$-induced apoptosis, albeit incompletely in some assays. None the less, this suggests that the Bcl-2 family affects apoptosis through modulation of transcription.

DISCUSSION

The Bcl-2 family regulates apoptosis through multiple mechanisms. For example, these proteins can function at the mitochondria by possibly forming channels that regulate mitochondrial membrane potential and cytochrome C release. Alternatively, the Bcl-2 family may directly regulate caspase activation through interactions with Ced-4-like proteins. We describe a novel E1B 19K-interacting protein, Btf, isolated through a two-hybrid screen that regulates an alternative pathway to control apoptosis. Two transcripts corresponding to btf were identified, btf$_S$ and btf$_L$. Both appeared to be widely expressed, but were deleted in some tumors. Here, we described the function and biological significance of the protein product generated from the shorter form, Btf$_S$ which differs from BtfL in just a 49 amino acids in the C-terminal region.

Double staining experiments were able to show the co-localization of Btf$_S$, with E1B 19K, Bcl-2 and Bcl-X$_L$, thereby supporting the interactions observed in the yeast two-hybrid assay as well as by in vitro

TABLE 1

Overexpression of Btf$_S$ induces cell death[a]

| | 48 h posttransfection | | | | | 72 h posttransfection | | | | |
|---|---|---|---|---|---|---|---|---|---|---|
| Vector | % EGFP positive | % sub-G$_{0/1}$ | % G$_{0/1}$ | % S | % G$_2$/M | % EGFP positive | % sub-G$_{0/1}$ | % G$_{0/1}$ | % S | % G$_2$/M |
| pIRES-EGFP + pcDNA3 | 61.2 | 3.4 | 42.3 | 20.0 | 33.7 | 45.7 | 5.6 | 32.5 | 20.9 | 40.6 |
| pIRES-EGFP + pCMV-E1B 19K | 72.0 | 1.5 | 54.2 | 21.0 | 23.6 | 59.0 | 8.8 | 55.4 | 20.8 | 14.8 |
| pIRES-EGFP-Btf$_s$ + pcDNA3 | 19.5 | 15.8 | 36.7 | 21.7 | 25.6 | 13.2 | 29.1 | 33.2 | 20.6 | 16.7 |
| pIRES-EGFP-Btf$_s$ + pCMV-E1B 19K | 34.3 | 10.1 | 41.8 | 17.8 | 30.0 | 15.4 | 36.9 | 36.0 | 13.3 | 13.6 |

[a]HeLa cells were electroporated with 20 μg of pIRES-EGFP-Btf$_s$ or empty vector in combination with 10 μg of pCMV-E1B 19K or empty pcDNA3 vector. The cells were harvested 48 and 72 h posttransfection, fixed in 2% paraformaldehye, and stained with PBS containing 1 μg of propidium iodide per ml. 250 μg of RASE A per ml. and 0.1% Tween 20. The cells were incubated for at least 30 min at room temperature and then analyzed by FACS. The results show the percentage of EGFP-positive cells and the cell cycle kinetics for the EGFP-positive population.

co-immunoprecipitation. While transiently expressed Btf$_S$ was nuclear and could be sequestered into the cytoplasm by the anti-apoptotic Bcl-2 family members, the localization of endogenous Btf$_S$ remains to be determined. It is entirely possible that in normal, non-apoptotic cells Btf$_S$ is predominantly expressed in the cytoplasm. In contrast, in dying cells, where there is a higher percentage of pro-apoptotic versus anti-apoptotic Bcl-2 family members, Btf$_s$ may translocate to the nucleus and potentiate apoptosis.

Btf$_S$ was able to bind DNA in vitro, and in reporter assays Btf$_S$ repressed transcription. The trans-repressive activity was inhibited by E1B 19K, Bcl-2 and Bcl-X$_L$ correlating with their cytoplasmic sequestration potentials. While it remains possible that part of this phenomenon is a result of Btf$_S$-induced apoptosis, the amount of cell death observed at 24 hours would not account for the 10-fold reduction in transcriptional activity. The evidence that Btf$_S$ is a transcription repressor was further supported by the identification of the ΔC210 deletion mutant that was sufficient for repressing transcription. The N-terminal fragment of Btf$_S$ is rich in glycine and serine, a feature that is common to transcriptional repressors. Taken together, these data provide evidence for a novel trans-repressive protein that triggers apoptosis which is sequestered and inhibited by Bcl-2 family members.

One of the features of the Bcl-2 family exemplified by the Btf$_S$ interaction is their ability to sequester other cellular proteins from their normal subcellular localization. This process enables E1B 19K and Bcl-2 to inhibit apoptosis using more than one cellular pathway. The best characterized example concerns the association between pro-apoptotic and anti-apoptotic Bcl-2 family members. While these interactions have been known for several years, recent studies of E1B 19K and Bax have demonstrated that these family members can alter each other's sub-cellular localization. Bax is normally stimulated to go to the mitochondria during apoptosis and causes a loss in mitochondrial membrane potential. However, over-expression of E1B 19K causes Bax to be sequestered to the nuclear periphery where E1B 19K is localized. This process most likely blocks the ability of Bax to disrupt mitochondrial function. The Bcl-2 family also associates with several unrelated proteins that may contribute to apoptosis regulation. For example, Bcl-2 associates with and targets the serine/threonine kinase Raf-1 to the mitochondria. Over-expression of Bcl-2 and Raf-1 cooperate to inhibit apoptosis. Another example that is now emerging is the association between the anti-apoptotic Bcl-2 family members with *C. elegans*, Ced-4, and with its mammalian homologue Apaf-1. These interactions directly block the activation of downstream caspases. Thus far, the *C. elegans* Bcl-2 homologue, Ced-9, as well as Bcl-x$_L$ and E1B 19K have been shown to bind to Ced-4, and at least Ced-9 and E1 B 19K can redistribute Ced-4 from the cytosol to cytoplasmic membranes. Bcl-x$_L$ also interacts with Apaf-1 and therefore it will be interesting to determine whether Bcl-X$_L$ can alter the localization of Apaf-1. In perhaps an analogous scenario, E1B 19K also sequesters the death-promoting protein FADD, an upstream component of Fas- and TNF-α-mediated death signaling pathway. Overexpressed FADD becomes multimerized and produces filaments throughout the cell. E1B 19K disrupts the FADD filaments causing FADD to relocalize with regions normally associated with 19K and inhibits FADD-dependent apoptosis. Here, we show that the Bcl-2 family members also sequester a nuclear transcription factor and that this may also play a role in apoptosis. The minimal region for E1B 19K required for interaction with Btf at the amino terminus (amino acids 1–36) appears to be distinct from the interaction regions involved in binding to other pro-apoptotic proteins (Bax, Ced-4, Nbk/Bik). This amino terminal region of E1B 19K may correspond to BH4 of Bcl-2 and Bcl-X$_L$, although this remains to be tested directly. Together these studies suggest that E1B 19K and possibly other Bcl-2 family members, act as binding proteins for a number of apoptosis regulators which could contribute to their widespread role as apoptosis inhibitors.

Transcriptional regulation often plays a critical role during apoptosis by either activating or repressing genes encoding basic apoptotic components. Indeed, inhibition of RNA and protein synthesis block apoptosis induced by a number of circumstances, including growth factor deprivation and following treatment with some chemotherapeutic drugs. In contrast, others have shown that these inhibitors can actually promote cell death, suggesting that loss of a short-lived survival factor can also lead to apoptosis. A number of transcription factors have been identified that may serve as positive or negative regulators of apoptosis. For example, the NF-κB transcription factor plays an important role in blocking apoptosis triggered by TNF-α although the target genes for NF-KB are not yet known. However, in other situations, NF-KB activation has been associated with induction of apoptosis. Furthermore, Bcl-2 and E1B 19K represses NF-KB activity providing another mechanism for Bcl-2 family members to control apoptosis.

Another transcription factor that may be regulated by the Bcl-2 family during apoptosis is p53. The p53 tumor suppressor protein is required for apoptosis during ionizing radiation and chemotherapeutic drugs, as well as transforming oncogenes such as c-myc and E1A. While p53 may have multiple functions, the transcriptional activity of p53 is clearly critical for the regulation of cell death in some situations but not all. However, it is still unclear whether p53-mediated apoptosis requires its transcriptional activation or repression properties, or perhaps both. On the one hand, p53 trans-activates both bax and fas, both of which are bonafide inducers of apoptosis. In contrast, several p53-repressible genes have been identified which may potentially contribute toward apoptosis, including bcl-2, MAP4, interleukin-6, c-fos, and c-myc. Expression of Bcl-2 and E1B 19K alleviate the transcriptional repression activity of p53 providing a mechanism for Bcl-2 family regulation of apoptosis. Thus, Bcl-2 family members can influence apoptosis by modulating the transcriptional activity of both NF-B and p53. Inhibition of Btf$_S$-mediated transcriptional repression and apoptosis by the Bcl-2 family establishes another connection between these apoptosis regulators and modulation of transcription. It will certainly be interesting to determine whether Btf$_S$ can influence the activities of other transcription factors related to apoptosis, such as NF-KB and p53.

We would predict that Btf$_S$ may repress the transcription of survival genes. Based on previous observations of regulation of gene expression by E1B 19K, one possible target may be the p53 inhibitor, Mdm-2. We have previously observed that stable expression of E1B 19K or Bcl-2 leads to an increase in Mdm-2 mRNA and protein levels. Such a mechanism could also account for the ability of E1B 19K to derepress the transcriptional repression mediated by p53 and E1A. While it will be worthwhile to determine whether Btf$_S$ could affect p53 modulation of these targets, the fact that Btf$_S$ was capable of inhibiting transformation by p53DD suggests that another target also exists that is independent of p53. We also have not been able to detect binding between Btf$_S$ and p53 (data not shown), although it is still plausible that Btf$_S$ associates with p53-dependent co-activators such as p300. Since the putative DNA-binding sites within Btf$_S$ contains homology to bZIP and Myb, it is conceivable that they share similar targets. Interestingly, correlations exist between both of these transcription factor families with apoptotic regulation. For example, application of functional blocking antibodies against the AP-1 proteins, Fos and Jun, or transfection with dominant-interfering Jun, inhibits apoptosis in neuronal cells following growth factor withdrawal. However, relevant target genes that contribute toward AP-1-mediated apoptosis have yet to be identified. The Myb family of transcriptional regulators inhibit apoptosis, and regulate the transcriptional activation of bcl-2. This may therefore provide a feedback loop between Btf$_S$ and Bcl-2. Future studies will be performed to determine whether Btf$_S$ regulates bcl-2, or other genes involved in apoptosis. The link between Btf$_S$ and the Bcl-2 family may provide an alternative mechanism by which the Bcl-2 family is able to regulate cell survival.

References

Abraham, S. E., S. Lobo, P. Yaciuk, H. G. Wang, and E. Moran. 1993. p300, and p300-associated proteins, are components of TATA-binding protein (TBP) complexes. *Oncogene* 8: 1639–47.

Arany, Z., W. Sellers, D. Livingston, and R. Eckner. 1994. E1A-associated p300 and CREB-associated CBP belong to a conserved family of coactivators. *Cell* 77: 799–800.

Avantaggiati, M. L., V. Ogryzko, K. Gardner, A. Giordano, A. S. Levine, and K. Kelly. 1997. Recruitment of p300-CBP in p53-dependent signal pathways. *Cell* 89: 1175–1184.

Bannister, A. J., and T. Kouzarides. 19915. CBP-induced stimulation of c-Fos activity is abrogated by E1A. *EMBO J.* 14: 4758–4762.

Bannister, A. J., and T. Kouzarides. 1996. The CBP coactivator is a histone acetyltransferase. *Nature (London)* 384: 641–643.

Barak, Y., T. Juven, R. Haffner, and M. Oren. 1993. mdm2 expression is induced by wild type p53 activity. *EMBO J.* 12; 461–468.

Buckbinder, L., R. Talbott, S. Velasco-Miguel, I. Takenaka, B. Faha, B. R. Seizinger, and N. Kley. 1995. Induction of the growth inhibitor IGF-binding protein 3 by p53. *Nature (London)* 377: 646–649.

Chen, J., X. Wu, J. Lin, and A. J. Levine. 1996. mdm-2 inhibits the G1 arrest and apoptosis functions of the p53 tumor suppressor protein. *Mol. Cell. Biol.* 16(Çls, functional domains, and DNA damage determine the extent of the apoptotic response of tumor cells. *Genes Dev.* 10: 2438–2451.

Chiou, S.-K., L. Rao, and E. White. 1994. Bcl-2 blocks p53-dependent apoptosis. *Mol. Cell. Biol.* 14: 2556–2563.

Chiou, S.-K., C. C. Tseng, L. Rao, and E. White. 1994. Functional complementation of the adenovirus E1B 19K protein with Bcl-2 in the inhibition of apoptosis in infected cells. *J. Virol.* 68: 6553–6566.

Chiou, S.-K., and E. White. 1997. p300 binding by E1A cosegregates with p53 induction but is dispensable for apoptosis. *J. Virol.* 71: 3515–3525.

Chrivia, J. C., R. P. Kwok, N. Lamb, M. Hagiwara, M. R. MontÇÆein CBP. *Nature (London)* 365: 855–859.

Dai, P., H. Akimaru, Y. Tanaka, D. X. Hou, T. Yasukawa, C. Kanei-Ishii, T. Takahashi, and S. Ishii. 1996. CBP as a transcriptional coactivator of c-Myb. *Genes Dev* 10: 528–40.

Debbas, M., and E. White. 1993. Wild-type p53 mediates apoptosis by E1A which is inhibited by E1B. *Genes Dev.* 7: 546–554.

Donehower, L. A., M. Harvey, B. L. Slagle, M. J. McArthur, C. A. Montgomery, J. S. Butel, and A. Bradley. 1992. Mice deficient for p53 are developmentally normal but susceptible to spontaneous tumors. *Nature (London)* 356: 215–221.

Dyson, N., and E. Harlow. 1992. Adenovirus E1A targets key regulators of cell proliferation. *Cancer Surv.* 12: 161–195.

Eckner, R., M. E. Ewen, D. Newsome, M. Gerdes, J. A. DeCaprio, J. B. Lawrence, and D. M. Livingston. 1994. Molecular cloning and functional analysis of the adenovirus E1A-associated 300-kD protein (p300) reveals a protein with properties of a transcription adaptor. *Genes Dev.* 8: 869–884.

El-Deiry, W. S., S. E. Kern, J. A. Pietenpol, K. W. Kinzler, and B. Vogelstein. 1992. Definition of a consensus binding site for p53. NatÇokino, V. E. Velculescu, D. B. Levy, R. Parsons, J. M. Trent, D. Lin, E. Mercer, K. W. Kinzler, and B. Vogelstein. 1993. WAF1, a potential mediator of p53 tumor suppression. *Cell* 75: 817–825.

Fakharzadeh, S. S., S. P. Trusko, and D. L. George. 1991. Tumorigenic potential associated with enhanced expression of a gene that is amplified in a mouse tumor cell line. *EMBO J.* 10: 1565–1569.

Funk, W. D., D. T. Pak, R. H. Karas, W. E. Wright, and J. W. Shay. 1992. A transcriptionally active DNA-binding site for human p53 protein complexes. *Mol. Cell. Biol.* 12: 2866–2871.

Gu, W., and R. G. Roeder. 1997. Activation of p53 sequence-specific DNA binding by acetylation of the p53 C-terminal domain. *Cell* 90: 595–606.

Gu, W., X.-L. Shi, and R. G. Roeder. 1997. Synergistic activation of transcription by CBP and p53. *Nature (London)* 387: 819–823.

Han, J., P. Sabbatini, D. Perez, L. Rao, D. Modha, and E. White. 1996. The E1B 19K protein blocks apoptosis by interacting with and inhibiting the p53-inducible and death-promoting Bax protein. *Genes Dev.* 10: 461–477.

Haupt, Y., Y. Barak, and M. Oren. 1996. Cell type-specific inhibition of p53-mediated apoptosis by mdm2. *EMBO J.* 15(Çthe rapid degradation of p53. *Nature (London)* 387: 296–299.

Hollstein, M., D. Sidransky, B. Vogelstein, and C. Harris. 1991. p53 mutations in human cancers. *Science* 253: 49–53.

Kastan, M. B., Q. Zhan, W. S. El-Deiry, F. Carrier, T. Jacks, W. V. Walsh, B. S. Plunkett, B. Vogelstein, and A. J. Fornace. 1992. A mammalian cell cycle checkpoint pathway utilizing p53 and GADD45 is defective in ataxia-telangiectasia. *Cell* 13: 587–597.

Ko, L. J., and C. Prives. 1996. p53: puzzle and paradigm. *Genes Dev.* 10: 1054–1072.

Kubbutat, M. H. G., S. N. Jones, and K. H. Vousden. 1997. Regulation of p53 stability by mdm2. *Nature (London)* 387: 299–303.

Kwok, R. P., J. R. Lundblad, J. C. Chrivia, J. P. Richards, H. P. Bachinger, R. G. Brennan, S. G. Roberts, M. R. Green, and R. H. Goodman. 1994. Nuclear protein CBP is a coactivator for the transcription factor CREB. *Nature (London)* 370: 223–226.

Lee, J. S., K. M. Galvin, R. H. See, R. Eckner, D. Livingston, E. Moran, and Y. Shi. 1995. Relief of YY1 transcriptional repression by adenovirus E1A is mediated by E1A-associated protein p300. *Genes Dev.* 9: 1188–98.

Levine, A. J. 1997. p53, the cellular gatekeeper for growth and division. *Cell* 88: 323–331.

Lill, N. L., S. R. Grossman, D. Ginsberg, J. DeCaprio and D. M. Livingston. 1997. Binding and modulation of p53 by p300/CBP coactivators. *Nature (London)* 387: 823–827.

Lowe, S., and H. E. Ruley. 1993. Stabilization of the p53 tumor suppressor is induced by adenovirus-5 E1A and accompanies apoptosis. *Genes Dev.* 7: 535–545.

Miyashita, T., and J. C. Reed. 1995. Tumor suppressor p53 is a direct transcriptional activator of the human bax gene. *Cell* 80: 293–299.

Momand, J., G. P. Çduct forms a complex with the p53 protein and inhibits p53-mediated transactivation. *Cell* 69: 1237–1245.

Montes de Oca Luna, R., D. S. Wagner, and G. Lozano. 1995. Rescue of early embryonic lethality in mdm2-deficient mice by deletion of p53. *Nature (London)* 378: 203–206.

Moran, E. 1993. DNA tumor virus transforming proteins and the cell cycle. *Curr. Opin. Genet. Dev.* 3: 63–70.

Muraoka, M., M. Konishi, R. Yanoshita, K. Tanaka, N. Shitara, J. M. Chong, T. Iwama, and M. Miyaki. 1996. p300 gene alterations in colorectal and gastric carcinomas. *Oncogene* 12: 1565–1569.

Murphy, M., A. Hinman, and A. J. Levine. 1996. Wild-type p53 negatively regulates the expression of a microtubule-associated protein. Genes Çssanova, B. H. Howard, and Y. Nakatani. 1996. The transcriptional coactivators p300 and CBP are histone acetyltransferases. *Cell* 87: 953–959.

Okamoto, K., and D. Beach. 1994. Cyclin G is a transcriptional target of the p53 tumor suppressor protein. *EMBO J.* 13: 4816–4822.

Oliner, J. D., J. Pietenpol, S. Thiagalingam, J. Gyuris, K. W. Kinzler, and B. Vogelstein. 1993. Oncoprotein MDM2 conceals the activation domain of tumor suppressor p53. *Nature (London)* 362: 857–860.

Pietenpol, J. A., T. Tokino, S. Thiagalingam, W. S. El-Deiry, K. W. Kinzler, and B. Vogelstein. 1994. Sequence-specific transcriptional activation is essential for growth suppression by p53. *Proc. Natl. Acad. Sci. USA* 91: 1998–2002.

Querido, E. J., J. G. Teoddro, and P. E. Branton. 1997. Accumulation of p53 induced by the adenovirus E1A protein requires regions involved in the stimulation of DNA synthesis. *J. Virol.* 71: 3526–3533.

Rao, L., D. Perez, and E. White. 1996. Lamin proteolysis facilitates nuclear events during apoptosis. *J. Cell. Biol.* 135: 1441–1455.

Rao, L., and E. White. 1997. Bcl-2 and ICE family of apoptotic regulators: Making a connection. *Curr. Opin. Genet. Dev.* 7: 52–58.

Sabbatini, P., S.-K. Chiou, L. Rao, and E. White. 1995. Modulation of p53-mediated transcription and apoptosis by the adenovirus E1B 19K protein. *Mol. Cell. Biol.* 15: 1060–1070.

Sabbatini, P., J. H. Han, S.-K. Chiou, D. Nicholson and E. White. 1997. Interleukin 1β converting enzyme-like proteases are essential for p53-mediated transcriptionally dependent apoptosis. Cell Growth Ç 1995. Essential role for p53-mediated transcription in apoptosis but not growth suppression. *Genes Dev.* 9: 2184–2192.

Sakamuro, D., V. Eviner, K. J. Elliot, L. Showe, E. White, and G. C. Prendergast. 1995. c-Myc induces apoptosis in epithelial cells by both p53-dependent and p53-independent mechanisms. *Oncogene* 11: 2411–2418.

Sanchez-Prieto, R., M. Lleonart, and S. Cajal. 1995. Lack of correlation between p53 protein level and sensitivity to DNA-damaging agents in keratinocytes carrying adenovirus E1A mutants. *Oncogene* 11: 675–682.

Scolnick, D. M., N. H. Chehab, E. S. Stavridi, M. C. Lien, L. Caruso, E. Moran, S. L. Berger, and T. D. Halazonetis. 1997. CREB-binding protein and p300-CBP-associated factor are transcriptional coactivators of the p53-tumor suppressor protein. *Cancer Res.* 57: 3693–6.

Shen, Y., and T. Shenk. 1994. Relief of p53 mediated transcriptional repression by the adenovirus E1B 19-kDa protein or the cellular Bcl-2 protein. *Proc. Natl. Acad. Sci. USA* 91: 8940–8944.

Steegenga, W. T., T. van Laar, N. Riteco, A. Mandarino, A. Shvarts, A. J. van der Eb, and A. G. Jochemsen. 1996. Adenovirus E1A proteins inhibit activation of transcription by p53. *Mol. Cell Biol.* 16: 2101–9.

Stein, R. W., M. Corrigan, P. Yaciuk, J. Whelan, and E. Moran. 1991. Analysis of E1A-mediated growth regulation functions: binding of the 300-kilodalton cellular product correlates with E1A repression function and DNA synthesis-inducing activity. *J. Virol.* 64: 4421–4427.

Thut, C. J., J.-L. Chen, R. Klemm, and R. Tjian. 1995. p53 transcriptional activation mediated by coactivators TAFII400 and TAFII60. *Science* 267: 100–104.

Vogelstein, B., and K. W. Kinzler. 1992. p53 Function and dysfunction. *Cell* 70: 523–526.

Wang, H.-G. H., Y. Rikitake, M. C. Carter, P. Yaciuk, S. E. Abraham, B. Zerler, and E. Moran. 1992. Identification of specific adenovirus E1A N-terminal residues critical to the binding of cellular proteins and the control of cell growth. *J. Virol.* 67: 476–488.

White, E., 1993. Regulation of apoptosis by the transforming genes of the DNA tumor virus adenovirusÇth, and the pursuit of apoptosisÇtini, and A. Denton. 1991. The adenovirus E1B 19-Kilodalton protein overcomes the cytotoxicity of E1A proteins. *J. Virol.* 65: 2968–2978.

White, E., and L. R. Gooding (1994). Regulation of apoptosis by human adenoviruses, *in Apoptosis: The Molecular Basis for Cell Death II.* D. T. a. F. Cope. New York, Cold Spring Harbor Laboratory Press: pp. 111–141.

Whyte, P., K. Ç proteins bind to the retinoblastoma gene productÇd A. J. Levine. 1993. The p53-mdm-2 autoregulatory feedback loop. Genes Çward, and Y. A. Nakatani. 1996. p300/CBP-associated factor that competes with the adenoviral oncoprotein E1a. *Nature (London)* 382: 319–324.

Yoshida, K., L. ÇT antigen has an enhancer dependent trans-activation function and relieves enchancer repression mediated by viral and cellular genes. *Genes Dev.* 1: 645–658.

Antonsson, B., F. Conti, A. Ciavatta, S. Montessuit, S. Lewis, I. Martinou, L. Bernasconi, A. Bernard, J.-J. Mermod, G. Mazzei, K. Maundrell, F. Gambale, R. Sadoul, and J.-C. Martinou. 1997. Inhibition of Bax channel-forming activity by Bcl-2. *Science* 277:370–372.

Barry, M. A., C. A. Behnke, and A. Eastman. 1990. Activation of programmed cell death (apoptosis) by cisplatin, other anticancer drugs, toxins and hyperthermia. *Biochem. Pharmacol.* 40:2353–62.

Bazer, S. B., and H. J. Deeg. 1992. Ultraviolet β-induced DNA fragmentation (apoptosis) in activated T-lymphocytes and Jurkat cells is augmented by inhibition of RNA and protein synthesis. *Exp. Hematol.* 20:80–86.

Beg, A. A., and D. Baltimore. 1996. An essential role for NF-κB in preventing TNF-α-induced cell death. *Science* 274:782–784.

Boise, L. H., M. Gonzalez-Garcia, C. E. Postema, L. Ding, T. Lindsten, L. A. Turka, X. Mao, G. Nuñez, and C. Thompson. 1993. bcl-x, a bcl-2-related gene that functions as a dominant regulator of apoptotic death. Cell 74:597–608.

Borner, C. 1996. Diminished cell proliferation associated with the death-protective activity of Bcl-2. J. Biol. Chem. 271:12695–12698.

Boyd, J., S. Malstrom, T. Subramanian, L. Venkatesh, U. Schaeper, B. E1Angovan, C. D'Sa-Eipper, and G. Chinnadurai. 1994. Adenovirus E1B 19 kDa and bcl-2 proteins interact with a common set of cellular proteins. Cell 79:341–351.

Boyd, J. M., G. J. Gallo, B. Elangovan, A. B. Houghton, S. Malstrom, B. J. Avery, R. G. Ebb, T. Subramanian, T. Chittenden, R. J. Lutz, and G. Chinnadurai. 1995. Bik1, a novel death-inducing protein shares a distinct sequence motif with Bcl-2 family proteins and interacts with viral and cellular survival-promoting proteins. Oncogene 11:1921–1928.

Caelles, C., A. Helmberg, and M. Karin. 1994. p53-dependent apoptosis in the absence of transcriptional activation of p53-target genes. Nature (London) 370:220–223.

Catron, K. M., H. Wang, G. Hu, M. M. Shen; and C. Abate-Shen. 1996. Comparison of MSX-1 and MSX-2 suggests a molecular basis for functional redundancy. Mech. of Dev. 55:185–199.

Catron, K. M., H. Zhang, S. C. Marshall, J. A. Inostroza, J. M. Wilson, and C. Abate. 1995. Transcriptional repression by Msx-1 does not require homeodomain DNA-binding sites. Mol. Cell Biol. 15:861–871.

Chinnaiyan, A. M., K. O'Rourke, B. R. Lane, and V. M. Dixit. 1997. Interaction of CED-4 with CEb-3 and CED-9: a molecular framework for cell death. Science 275:1122–1126.

Chittenden, T., C. Flemmington, A. B. Houghton, R. G. Ebb, G. J. Gallo, B. Elangovan, G. Chinnadurai, and R. J. Lutz. 1995. A conserved domain in Bak, distinct from BH1 and BH2, mediates cell death and protein binding functions. EMBO J. 14:5589–5596.

Clarke, A. R., C. A. Purdie, D. J. Harrison, R. G. Morris, C. C. Bird, M. L. Hooper, and A. H. Wyllie. 1993. Thymocyte apoptosis induced by p53-dependent and independent pathways. Nature (London) 362:849–852.

Estus, S., W. J. Zaks, R. S. Freeman, M. Gruda, R. Bravo, and E. M. Johnson, Jr. 1994. Altered gene expression in neurons during programmed cell death: identification of c-jun as necessary for neuronal apoptosis. J. Cell. Biol. 127:1717–1727.

Farrow, S. N., J. H. M. White, I. Martinou, T. Raven, K.-T. Pun, C. J. Grinham, J.-C. Martinou, and R. Brown. 1995. Cloning of a bcl-2 homologue by interaction with adenovirus E1B 19K. Nature (London) 374:731–733.

Fernandez-Sarabia, M. J., and J. R. Bischoff. 1994. Bcl-2 associates with the ras-related protein R-ras p23. Nature (London) 366:274–275.

Frampton, J., T. Ramqvist, and T. Graf. 1996. v-Myb of E26 leukemia virus up-regulates bcl-2 and: suppresses apoptosis in myeloid cells. Genes Dev. 10:2720–2731.

Gonzalez-Garcia, M., R. Perez-Ballestero, L. Ding, L. Duan, L. H. Boise, C. B. Thompson, and G. Nuñez. 1994. bcl-XL is the major bcl-x mRNA form expressed during murine development and its product localizes to mitochondria. Development 120:3033–42.

Grimm, S., M. K. A. Bauer, P. A. Baeuerle, and K. Schulze-Osthoff. 1996. Bcl-2 down-regulates the activity of transcription factor NF-kB induced upon apoptosis. J. Cell Biol. 134:13–23.

Ham, J., C. Babij, J. Whitfield, C. M. Pfarr, D. Lallemand, M. Yaniv, and L. L. Rubin. 1995. A c-Jun dominant negative mutant protects sympathetic neurons against programmed cell death. Neuron 14:927–39.

Han, J., D. Modha, and E. White. 1998. Interaction of E1B 19K with Bax is required to block Bax-induced loss of mitochondrial membrane potential and apoptosis. Oncogene, in press.

Han, J., P. Sabbatini, and E. White. 1996. Induction of apoptosis by human Nbk/Bik, a BH3 containing E1B 19K interacting protein. Mol. Cell. Biol. 16:5857–5864.

Han, J., H. D. Wallen, G. Nuñez, and E. White. 1998. E1B 19,000-molecular-weight protein interacts with and inhibits Ced-4-dependent, FLICE-mediated apoptosis. Mol. Cell. Biol. 18:6052–6062.

Haupt, Y., S. Rowan, E. Shaulian, K. Vousden, and M. Oren. 1995. Induction of apoptosis in HeLa cells by transactivation-deficient p53. Genes Dev. 9:2170–2183.

Hermeking, H., and D. Eick. 1994. Mediation of c-Myc-induced apoptosis by p53. Science 265:2091–2093.

Hockenbery, D., G. Nuñez, C. Milliman, R. D. Schreiber, and S. Korsmeyer. 1990. Bcl-2 is an inner mitochondrial membrane protein that blocks programmed cell death. Nature (London) 348:334–336.

Hu, Y., M. A. Benedict, D. Wu, N. Inohara, and G. Nuñez. 1998. Bcl-$X_L$ interacts with Apaf-1 and inhibits Apaf-1-dependent caspase-9 activation. Proc. Natl. Acad. Sci. USA 95:4386–4391.

Huang, D. C., L. A. O'Reilly, A. Strasser, and S. Cory. 1997. The anti-apoptosis function of Bcl-2 can be genetically separated from its inhibitory effect on cell cycle entry. EMBO J. 16:4628–4638.

Ivanov, V. N., G. Deng, E. R. Podack, and T. R. Malek. 1995. Pleiotropic effects of Bcl-2 on transcription factors in T cells: potential role of NF-kappa B p50-p50 for the anti-apoptotic function of Bcl-2. Int. Immunol. 7:1709–1720.

Jacobson, M. D., M. Weil, and M. C. Raff. 1997. Programmed cell death in animal development. Cell 88:347–354.

Karin, M., L. Zg, and E. Zandi. 1997. AP-1 function and regulation. Curr. Opin. Cell Biol. 9:240–246.

Kley, N., R. Y. Chung, S. Fay, J. P. Loeffler, and B. R. Seizinger. 1992. Repression of the basal c-fos promoter by wild-type p53. Nucleic Acids Res. 20:4083–7.

Linette, G. P., Y. Li, K. Roth, and S. J. Korsmeyer. 1996. Cross talk between cell death and cell cycle progression: BCL-2 regulates NFAT-mediated activation. Proc. Natl. Acad. Sci. USA 93:9545–9552.

Lowe, S. W., E. M. Schmitt, S. W. Smith, B. A. Osborne, and T. Jacks. 1993. p53 is required for radiation-induced apoptosis in mouse thymocytes. Nature (London) 362:847–849.

Madden, S. L., D. M. Cook, and F. J. D. Rauscher. 1993. A structure-function analysis of transcriptional repression mediated by the WT1, Wilm's tumor suppressor protein. Oncogene 8:1713–1720.

Martin, D. P., R. E. Schmidt, P. S. DiStefano, 0. H. Lowry, J. G. Carter, and E. M. Johnson, Jr. 1988. Inhibitors of protein synthesis and RNA synthesis prevent neuronal death caused by nerve growth factor deprivation. J. Cell. Biol. 106:829–844.

Martin, S. J., S. V. Lennon, A. M. Bonham, and T. C. Cotter. 1990. Induction of apoptosis (programmed cell death) in human HL-60 cells by inhibition of RNA or protein synthesis. J. Immunol. 145:1859–1867.

Mazel, S., D. Burtrum, and H. T. Petrie. 1996. Regulation of cell division cycle progression by bcl-2 expression: a potential mechanism for inhibition of programmed cell death. J. Exp. Med. 183:2219–2226.

Merino, R., D. A. Grillot, P. L. Simonian, S. Muthukkumar, W. C. Fanslow, S. Bondada, and G. Nuñez. 1995. Modulation of anti-IgM-induced B cell apoptosis by Bcl-xL and CD40 in WEHI-231 cells. Dissociation from cell cycle arrest and dependence on the avidity of the antibody-IgM receptor interaction. J Immunol 155:3830–3838.

Minn, A. J., P. Vélez, S. L. Schendel, H. Liang, S. W. Muchmore, S. W. Fesik, M. Fill, and C. B. Thompson. 1997. Bcl-$X_L$ forms an ion channel in synthetic lipid membranes. Nature (London) 385:353–357.

Mitelman, F. 1995. Catalog of Chromosome Aberrations in Cancer. New York, Wiley: Liss.

Miyashita, T., S. Krajewski, M. Krajewska, H. G. Wang, H. K. Lin, D. A. Liebermann, B. Hoffman, and J. C. Reed. 1994. Tumor suppressor p53 is a regulator of bcl-2 and bax gene expression in vitro and in vivo. Oncogene 9:1799–1805.

Miyashita, T., M. U, T. Inoue, J. C. Reed, and M. Yamada. 1997. Bcl-2 relieves the trans-repressive function of the glucocorticoid receptor and inhibits the activation of CPP32-like cysteine proteases. Biochem. Biophys. Res. Commun. 233:781–787.

Mizumoto, K., R. J. Rothman, and J. L. Farber. 1994. Programmed cell death (apoptosis) of mouse fibroblasts is induced by the topoisomerase II inhibitor etoposide. Mol. Pharmacol. 46:890–5.

Moberg, K. H., W. A. Tyndall, and D. J. Hall. 1992. Wild-type murine p53 represses transcription from the murine c-myc promoter in a human glial cell line. J. Cell Biochem. 49:208–15.

Momand, J., G. P. Zambetti, D. C. Olson, D. George, and A. J. Levine. 1992. The mdm-2 oncogene product forms a complex with the p53 protein and inhibits: p53-mediated transactivation. Cell 69:1237–1245.

Monagan, P., D. Robertson, T. A. Amos, M. J. Dyer, D. Y. Mason, and M. F. Greaves. 1992. Ultrastructural localization of Bcl-2 protein. J. Histochem. Cytochem. 40:1819–1825.

Muchmore, S. W., M. Sattler, H. Liang, R. P. Meadows, J. E. Harlan, H. S. Yoon, D. Nettesheim, B. S. Chang, C. B. Thompson, S.-L. Wong, S.-C. Ng, and S. W. Fesik. 1996. X-ray and NMR structure of human Bcl-XL, an inhibitor of programmed cell death. Nature (London) 381:335–341.

Ng, F. W. H., M. Nguyen, T. Kwan, P. E. Branton, D. W. Nicholson, J. A. Cromlish, and G. C. Shore. 1997. p28 Bap31, a Bcl-2/Bcl-$X_L$- and procaspase-8-associated protein in the endoplasmic reticulum. J. Cell Biol. 139:327–338.

Oltvai, Z. N., C. L. Millman, and S. J. Korsmeyer. 1993. Bcl-2 heterodimerizes in vivo with a conserved homolog, Bax, that accelerates programmed cell death. Cell 74:609–619.

Osada, S., T. Ikeda, M. Xu, T. Nishihara, and M. Imagawa. 1997. Identification of the transcriptional repression domain of nuclear factor 1-A. Biochem. Biophys. Res. Commun. 283:744–747.

Owen-Schaub, L., W. Zhang, J. C. Cusack, L. S. Angelo, S. M. Santee, T. Fujiwara, J. A. Roth, A. B. Deisseroth, W.-W. Zhang, E. Kruzel, and R. Radinsky. 1995. Wild-type human p53 and a temerature-sensitive mutant induce Fas/Apo-1 expression. Mol. Cell. Biol. 15:3032–3040.

Pan, G., K. O'Rourke, and V. M. Dixit. 1998. Caspase-9, Bcl-XL, and Apaf-1 form a ternary complex. J. Biol. Chem. 273:5841–5845.

Parsa, N. Z., G. Gaidano, A. B. Mukherjee, R. S. Hauptschein, G. Lenoir, R. Dalla-Favera, and R. S. Chaganti. 1994. Cytogenetic and molecular analysis of 6q deletions in Burkitt's lymphoma cell lines. Genes Chromosom. Cancer 9:13–8.

Perez, D., and E. White. 1998. E1B 19K inhibits Fas-mediated apoptosis through PADD-dependent sequestration of FLICE. J. Cell Biol. 141:1255–1266.

Rao, L., M. Debbas, P. Sabbatini, D. Hockenberry, S. Korsmeyer, and E. White. 1992. The adenovirus E1A proteins induce apoptosis which is inhibited by the E1B 19K and Bcl-2 proteins. Proc. Natl. Acad. Sci. USA 89:7742–7746.

Rao, L., D. Modha, and E. White. 1997. The E1B 19K protein associates with lamins in vivo and its proper localization is required for inhibition of apoptosis. Oncogene 15:1587–1597.

Sabbatini, P., J. Lin, A. J. Levine, and E. White. 1995. Essential role for p53-mediated transcription in E1A-induced apoptosis but not growth suppression. Genes Dev. 9:2184–2192.

Santhanam, U., A. Ray, and P. B. Sehgal. 1991. Repression of the interleukin 6 gene promoter by p53 and the retinoblastoma susceptibility gene product. Proc. Natl. Acad. Sci. USA B8:7605–9.

Sattler, M., H. Liang, D. Nettesheim, R. P. Meadows, J. E. Harlan, M. Eberstadt, H. S. yoon, S. B., Shuker, B. S. Chang, A. J. Minn, C. B. Thompson, and S. W. Fesik. 1997. Structure of Bcl-XL-Bak peptide complex: recognition between regulators of apoptosis. Science 275:983–986.

Schendel, S. L., Z. Xie, M. O. Montal, S. Matsuyama, and M. Montal. 1997. Channel formation by antiapoptotic protein Bcl-2. Proc. Natl. Acad. Sci. USA 94:5113–5118.

Schmitz, M. L., A. indorf, F. P. Limbourg, H. Stadtler, E. B. Traenckner, and P. A. Baeuerle. 1996. The dual effect of adenovirus type 5 E1A 13S protein on NF-kappaB activation is antagonized by E1B 19K. Mol. Cell. Biol. 16:4052–4063.

Scott, S. A., and A. M. Davies. 1990. Inhibition of protein synthesis prevents cell death in sensory and parasympathetic neurons deprived of neurotrophic in vitro. J. Neurobiol. 21:630–638.

See, R. H., and Y. Shi. 1998. Adenovirus E1B 19,000-molecular-weight protein activates c-Jun N-terminal kinase and c-Jun-mediated transcription. Mol. Cell Biol. 18:4012–4022.

Shaulian, E., A. Zauberman, D. Ginsberg, and M. Oren. 1992. Identification of a minimal transforming domain of p53: negative dominance through abrogation of sequence-specific DNA binding. Mol. Cell. Biol. 12:5581–5592.

Shen, Y., and T. Shenk. 1994. Relief of p53 mediated transcriptional repression by the adenovirus E1B 19-kDa protein or the cellular Bcl-2 protein. Proc. Natl. Acad. Sci. USA 91:8940–8944.

Shibasaki, F., E. Kondo, T. Akagl, and F., McKeon. 1997. Suppression of signalling through transcription factor NF-AT by interactions between calcineurin and Bcl-2. Nature (London) 3B6:728–731.

Siegel, R. M., D. A. Martin, L. Zheng, S. Y. Ng, J. Bertin, J. Cohen, and M. J. Lenardo. 1998. Death-effector filaments: novel cytoplasmic structures that recruit caspases and trigger apoptosis. J. Cell Biol. 141:1243–1253.

Spector, M. S., S. Desnoyers, D. J. Hoeppner, and M. O. Hengartner. 1997. Interaction between the C. elegans cell-death regulators CED-9 and CED-4. Nature (London) 385:653–656.

Takayama, S., T. Sato, S. Krajewski, K. Kochel, S. Irie, J. A. Millan, and J. C. Reed. 1995. Cloning and functional analysis of Bag-1: a novel Bcl-2-binding protein with anti-cell death activity. Cell 80:279–284.

Taylor, D., P. Badiani, and K. Weston. 1996. A dominant interfering Myb mutant causes apoptosis in T cells. Genes Dev. 10:2732–2744.

Thomas, A., and E. White. 1998. Suppression of the p300-dependent mdm2 negative-feedback loop induces the p53 apoptotic function. Genes Dev. 12:1975–1985.

Vairo, G., K. M. Innes, and J. M. Adams. 1996. Bcl-2 has a cell cycle inhibitory function separable from its enhancement of cell survival. Oncogene 13:1511–1519.

Van Antwerp, D. J., S. J. Martin, T. Kafri, D. R. Green, and I. M. Verma. 1996. Suppression of TNF-α-induced apoptosis by NF-κB. Science 274:787–789.

Vaux, D. L., and I. L. Weissman. 1993. Neither macromolecular synthesis nor myc is required for cell death via the mechanism that can be controlled by Bcl-2. Mol. Cell Biol. 13:7000–5.

Walker, P. R., C. Smith, T. Youdale, J. Leblanc, J. F. Whitfield, and M. Sikorska. 1991. Topoisomerase II-reactive chemotherapeutic drugs induce apoptosis in thymocytes. Cancer Res. 51:1078–85.

Wang, C.-Y., M. W. Mayo, and A. S. Baldwin, Jr. 1996. TNF- and cancer therapy-induced apoptosis: potentiation by inhibition of NF-κB. Science 274:784–787.

Wang, H. G., U. R. Rapp, and J. C. Reed. 1996. Bcl-2 targets the protein kinase Raf-1 to mitochondria. Cell 87:629–38.

Weston, K. 1998. Myb proteins in life, death and differentiation. Curr. Opin. Genet. Dev. 8:76–81.

White, E. 1996. Life, death, and the pursuit of apoptosis. Genes Dev. 10:1–15.

White, E., R. Cipriani, P. Sabbatini, and A. Denton. 1991. The adenovirus ElS 19-Kilodalton protein overcomes the cytotoxicity of E1A proteins. J. Virol. 65:2968–2978.

White, E., A. Denton, and B. Stillman. 1988. Role of the adenovirus E1B 19,000-dalton tumor antigen in regulating early gene expression. J. Virol. 62:3445–3454.

White, E., S. H. Blose, and B. Stillman. 1984. Nuclear envelope localization of an adenovirus tumor antigen maintains the integrity of cellular DNA. Mol. Cell. Biol. 4:2865–2875.

White, E., and R. Cipriani. 1989. Specific disruption of intermediate filaments and the nuclear lamina by the 19 kDa product of the adenovirus E1 B oncogene. Proc. Natl. Acad. Sci. USA 86:9886–9890.

White, E., B. Faha, and B. Stillman. 1986. Regulation of adenovirus gene expression in human W138 cells by an E1B-encoded tumor antigen. Mol. Cell. Biol. 6:3763–3773.

White, E., P. Sabbatini, M. Debbas, W. S. M. Wold, D. I. Kusher, and L. Gooding. 1992. The 19-kilodalton adenovirus E1B transforming protein inhibits programmed cell death and prevents cytolysis by tumor necrosis factor α. Mol. Cell. Biol. 12:2570–2580.

Wolter, K. G., Y.-T. Hsu, C. L. Smith, A. Nechushtan, and X.-G. Xi. 1997. Movement of Bax from the cytosol to mitochondria during apoptosis. J. Cell. Biol. 139:1281–1292.

Wu, D., H. D. Wallen, N. Inohara, and G. Nunez. 1997. Interaction and regulation of the Caenorhabditis elegans death protease CED-3 by CED-4 and CED-9. J. Biol. Chem. 272:21449–21454.

Wu, D., H. D. Wallen, and G. Nunez. 1997. Interaction and regulation of subcellular localization of CED-4 by CED-9. Science 275:1126–1128.

Wyllie, A. H. 1980. Cell death: The significance of apoptosis. Int. Rev. Cytol. 68;251–306.

Yang, W. M., C. Inouye, Y. Zeng, D. Bearss, and E. Seto. 1996. Transcriptional repression by YY1 is mediated by interaction with a mammalian homolog of the yeast global regulator RPD3. Proc. Natl. Acad. Sci. USA 93:12845–12850.

Yin, X.-M., Z. Oltvai, and S. Korsmeyer. 1994. BH1 and BH2 domains of Bcl-2 are required for inhibition of apoptosis and heterodimerization with Bax. Nature (London) 369:321–323.

Yoshida, K., L. Venkatesh, M. Kuppuswamy, and G. Chinnadurai. 1987. Adenovirus transforming 19-kD T antigen has an enhancer dependent trans-activation function and relieves enchancer repression mediated by viral and cellular genes. Genes Dev. 1:645–658.

Zou, H., W. J. Henzel, X. Liu, A. Lutschg, and X. Wang. 1997. Apaf-1, a human protein homologous to C. elegans CED-4, participates in cytochrome c-dependent activation of caspase-3. Cell 90:405–413.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A recombinant cell line for assessing therapeutic agents that regulate apoptosis, said recombinant cell line being stably transfected with:
   a) a first plasmid expressing a p300/CBP responsive promoter operably linked to a first reporter gene;
   b) a second plasmid expressing a non p300/CBP responsive promoter operably linked to a second reporter gene; and optionally
   c) a third plasmid expressing a selectable marker gene.

2. The cell line of claim 1, said cell line being further stably transfected with an additional plasmid encoding wild-type p300/CBP to augment endogenously expressed p300/CBP protein levels.

3. A screening method for determining if a therapeutic agent inhibits p300/CBP activity thereby inducing apoptosis, comprising:

a) contacting recombinant cells with said therapeutic agent, said recombinant cells being stably transfected with:
   i) a first plasmid expressing a p30/CBP responsive promoter operably linked to a first reporter gene;
   ii) a second plasmid expressing a, non p300/CBP responsive promoter operably linked to a second reporter gene; and optionally
   iii) a third plasmid expressing a selectable marker gene;
b) assessing said recombinant cells for repression of the first reporter gene by said therapeutic agent; and
c) assessing said recombinant cells for repression of the second reporter gene by said therapeutic agent, repression in step b) and not step c) indicating that the therapeutic agent inhibits p300/CBP activity and thereby induces apoptosis.

* * * * *